US007173130B2

(12) United States Patent
Tsien et al.

(10) Patent No.: US 7,173,130 B2
(45) Date of Patent: Feb. 6, 2007

(54) DETECTION OF TRANSMEMBRANE POTENTIALS BY OPTICAL METHODS

(75) Inventors: Roger Y. Tsien, La Jolla, CA (US); Jesus E. Gonzalez, III, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 128 days.

(21) Appl. No.: 09/967,772

(22) Filed: Sep. 28, 2001

(65) Prior Publication Data

US 2002/0164577 A1 Nov. 7, 2002

Related U.S. Application Data

(63) Continuation of application No. 09/459,956, filed on Dec. 13, 1999, now Pat. No. 6,342,379, which is a continuation-in-part of application No. 08/765,860, filed as application No. PCT/US96/09652 on Jun. 6, 1996, now Pat. No. 6,107,066, which is a continuation-in-part of application No. 08/481,977, filed on Jun. 6, 1995, now Pat. No. 5,661,035.

(51) Int. Cl.
  *C07D 403/06* (2006.01)
(52) U.S. Cl. .................................... 544/296
(58) Field of Classification Search ................ 544/296
  See application file for complete search history.

(56) References Cited

U.S. PATENT DOCUMENTS

| | | | |
|---|---|---|---|
| 3,480,436 A * | 11/1969 | Wilson | 430/522 |
| 4,560,665 A | 12/1985 | Nakae et al. | |
| 4,861,727 A | 8/1989 | Hauenstein et al. | |
| 4,900,934 A | 2/1990 | Peeters et al. | |
| 5,244,813 A | 9/1993 | Walt et al. | |
| 5,661,035 A | 8/1997 | Tsien et al. | |
| 5,763,167 A | 6/1998 | Conrad | |
| 6,107,066 A | 8/2000 | Tsien et al. | |

FOREIGN PATENT DOCUMENTS

| | | |
|---|---|---|
| DE | 43619 * | 12/1965 |
| EP | 0137515 A2 | 4/1985 |
| EP | 0397641 A2 | 11/1990 |
| EP | 0429907 A2 | 6/1991 |
| EP | 0520262 A1 | 12/1992 |
| EP | 0552107 A1 | 7/1993 |
| WO | WO95/08637 A1 | 3/1995 |
| WO | WO95/27204 A1 | 10/1995 |
| WO | WO96/41166 A2 | 12/1996 |
| WO | WO98/30715 A1 | 7/1998 |

OTHER PUBLICATIONS

J. Gonzalez et al, HCAPLUS abstract accession No. 1997: 353686 (1997).*

J. Gonzalez et al, HCAPLUS abstract accession No. 1995: 827962 (1995).*
J. Fabian et al, HCAPLUS abstract accession No. 1974: 16415 (1974).*
A. Benniston et al, HCAPLUS abstract accession No. 1994: 680062 (1994).*
Kodak, HCAPLUS abstract accession No. 1960: 853 (1960).*
J. Russell et al, The Journal of Biological Chamistry, vol. 254, No. 6, pp. 2047-2052 (1979).*
J. Kohn et al, Analytical Chemistry, vol. 58, pp. 3184-3188 (1986).*
S. Alper et al, Biochemistry and Cell Biology, vol. 76, No. 5, pp. 799-806 (1998).*
Niles et al., "Resonance Energy Transfer Imaging of Phospholipid Vesicle Interaction with a Planar Phospholipid Membrane," *J. Gen Physiol*. The Rockefeller University Press vol. 107 Mar. 1996 (pp. 329-351).
Wilson et al., "Lymphocyte Membrane Potential and $Ca^{2+}$—Sensitive Potassium Channels Described by Oxonol Dye Fluorescence Measurements," *Journal of Cellular Physiology* 125:72-81 (1985).

(Continued)

*Primary Examiner*—Mary E. Ceperley
(74) *Attorney, Agent, or Firm*—Townsend and Townsend and Crew LLP

(57) ABSTRACT

Methods and compositions are provided for detecting changes in membrane potential in membranes biological systems. In one aspect, the method comprises;
  a) providing a living cell with a first reagent comprising a charged hydrophobic molecule which is typically a fluorescence resonance energy transfer (FRET) acceptor or donor, or is a quencher and is capable of redistributing within the membrane of a biological membrane in response to changes in the potential across the membrane;
  b) providing the cell with a second reagent that can label the first face or the second face of a biological membrane within the cell;
  c) detecting light emission from the first reagent or the second reagent.

One aspect of this method involves monitoring membrane potential changes in subcellular organelle membranes in a living cells.

Another aspect of the invention is the use of certain embodiments of the method for the screening of test chemicals for activity to modulate the activity of a target ion channel.

Another aspect of the present invention is a transgenic organism comprising a first reagent that comprises a charged hydrophobic fluorescent molecule, and a second reagent comprising a bioluminescent or naturally fluorescent protein.

8 Claims, 27 Drawing Sheets

OTHER PUBLICATIONS

Wilson et al., "Voltage-Sensitive Cyanine Dye Fluorescence Signals in Lymphocytes: Plasma Membrane and Mitochondrial Components," *Journal of Cellular Physiology* 125:61-71 (1985).

Cacciatore, Timothy W., et al. "Identification of Neural Circuits by Imaging Coherent Electrical Activity With FRET-Based Dyes", *Neuron* (1999) 23:449-459.

González, Jesús E., et al. "Voltage Sensing by Fluorescence Resonance Energy Transfer in Single Cells", *Biophysical Journal* (1995) 69:1272-1280.

González, Jesús E., et al. "Improved indicators of cell membrane potential that use fluorescence resonance energy transfer", *Chemistry & Biology* (1997) 4:269-277.

González, Jesús E., et al. "Intracellular detection assays for high-throughput screening", *Current Opinion in Biotechnology* (1998) 9:624-631.

Gutièrrez-Merino C., et al. "Preferential Distribution of the Fluorescent Phospholipid Probes NBD-Phosphatidylcholine and Rhodamine-Phosphatidylethanolamine in the Exofacial Leaflet of Acetylcholine Receptor-Rich Membranes from *Torpedo marmorata*", *Biochemistry* (1995) 34:4846-4855.

Rink, T.J., et al. "Lymphocyte Membrane Potential Assessed With Fluorescent Probes", *Biochimica et Biophysica Acta* (1980) 595:15-30.

Gonález, Jesús E., et al., "Cell-based assays and instrumentation for screening ion-channel targets", *Drug Discovery Today* (1999) 4:431-439.

Silvius, John R., et al. "Novel Fluorescent Phospholipids for Assays of Lipid Mixing Between Membranes", *Biochemistry* (1987) 26:4279-4287.

Kraayenhof, Ruud, et al. "Probing Biomembrane Interfacial Potential and pH Profiles with a New Type of Float-like Fluorophores Positioned at Varying Distance from the Membrane Surface", *Biochemistry* (1993) 32:10057-10066.

Leventis, Rania, et al. "Intermembrane Lipid-Mixing Assays Using Acyl Chain-Labeled Coumarinyl Phospholipids", *Methods in Enzymology* (1993) 220:32-42.

Gutierrez-Merino, C., et al. "Preferential Distribution of the Fluorescent Phospholipid Probes NBD-Phosphatidylcholine and Rhodamine-Phosphatidylethanolamine in the Exofacial Leaflet of Acetylcholine Receptor-Rich Membranes from *Torpedo marmorata*", *Biochemistry* (1995) 34:4846-4855.

Witzak, Dorett "Oxonol luminophores containing functionalized side chains" (dissertation) carried out at the Heinrich Heine University of Düsseldorf, Germany, (Oct. 1993-Jun. 1994) pp. 1-43.

Bechtel, Sandra "Synthesis of styryl dyes containing reactive groups" (dissertation) carried out at the Heinrich Heine University of Düsseldorf, Germany, (Sep. 1993-Apr. 1994) pp. 1-32.

\* cited by examiner

Fluorescent Phosphatidylethanolamine Conjugates That Function
as FRET Partners to Voltage-Sensitive Oxonols

SEQUENCE LISTING

<160> NUMBER OF SEQ ID NOS: 22

<210> SEQ ID NO 1
<211> LENGTH: 720
<212> TYPE: DNA
<213> ORGANISM: Green Fluorescent Protein

<400> SEQUENCE: 1

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttctccta cggcgtgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aacctggagt acaacttcaa cagccacaac gtctatatca tggccgacaa gcagaagaac     480
ggcatcaagg tgaacttcaa gatcgccac aacatcgagg acggcagcgt gcagctcgcc     540
gaccactacc agcagaacac ccccatcggc gacggccccg tgctgctgcc cgacaaccac     600
```

```
tacctgagca tccagtccgc cctgagcaaa gaccccaacg agaagcgcga tcacatggtc    660
ctgctggagt tcgtgaccgc cgccgggatc actctcggca tggacgagct gtacaagtaa    720

<210> SEQ ID NO 2
<211> LENGTH: 690
<212> TYPE: DNA
<213> ORGANISM: Anemonia majano

<400> SEQUENCE: 2
atggctcttt caaacaagtt tatcggagat gacatgaaaa tgacctacca tatggatggc     60
tgtgtcaatg ggcattactt taccgtcaaa ggtgaaggca acgggaagcc atacgaaggg    120
acgcagactt cgacttttaa agtcaccatg gccaacggtg gcccttgc attctccttt      180 gacatactat ctacagtgtt caaatatgga atcgatgct ttactgcgta tcctaccagt    240
atgcccgact atttcaaaca agcatttcct gacggaatgt catatgaaag gactttacc    300 tatgaagatg gaggagttgc tacagccagt tgggaaataa gccttaaagg caactgcttt   360
gagcacaaat ccacgtttca tggagtgaac tttcctgctg atggacctgt gatggcgaag   420
aagacaactg gttgggaccc atcttttgag aaaatgactg tctgcgatgg aatattgaag   480
ggtgatgtca ccgcgttcct catgctgcaa ggaggtggca attacagatg ccaattccac   540
acttcttaca agacaaaaaa accggtgacg atgccaccaa accatgtggt ggaacatcgc   600
attgcgagga ccgaccttga caaggtggc aacagtgttc agctgacgga gcacgctgtt    660
gcacatataa cctctgttgt ccctttctga                                     690

<210> SEQ ID NO 3
<211> LENGTH: 696
<212> TYPE: DNA
<213> ORGANISM: Zoanthus sp

<400> SEQUENCE: 3
atggctcagt caaagcacgg tctaacaaaa gaaatgacaa tgaaataccg tatggaaggg     60
tgcgtcgatg gacataaatt tgtgatcacg ggagagggca ttggatatcc gttcaaaggg   120
aaacaggcta ttaatctgtg tgtggtcgaa ggtggaccat tgccatttgc cgaagacata   180
ttgtcagctg cctttaacta cggaaacagg gttttcactg aatatcctca agacatagtt   240
gactatttca gaactcgtgt cctgctggaa tatcatgggg acaggtctt tctctttgag    300 gatgaagcag tttgcatatg taatgcagat ataacagtga gtgttgaaga aaactgcatg   360
tatcatgagt ccaaattta tggagtgaat tttcctgctg atggacctgt gatgaaaaag   420
atgacagata actgggagcc atcctgcgag aagatcatac cagtacctaa gcagggata    480 ttgaaagggg atgtctccat gtacctcctt ctgaaggatg gtgggcgttt acggtgccaa   540 tcgacacag tttacaaagc aaagtctgtg ccaagaaaga tgccggactg gcacttcatc    600
cagcataagc tcacccgtga agaccgcagc gatgctaaga atcagaaatg gcatctgaca   660
gaacatgcta ttgcatccgg atctgcattg ccctga                              696

<210> SEQ ID NO 4
<211> LENGTH: 696
<212> TYPE: DNA
<213> ORGANISM: Zoanthus sp

<400> SEQUENCE: 4
atggctcatt caaagcacgg tctaaaagaa gaaatgacaa tgaaatacca catggaaggg     60
```

-continued

```
tgcgtcaacg gacataaatt tgtgatcacg ggcgaaggca ttggatatcc gttcaaaggg    120
aaacagacta ttaatctgtg tgtgatcgaa ggggacccat tgccatttc cgaagacata    180 ttgtcagctg gctttaagta cggagacagg attttcactg aatatcctca agacatagta    240
gactatttca agaactcgtg tcctgctgga tatacatggg gcaggtcttt tctctttgag    300
gatggagcag tctgcatatg caatgtagat ataacagtga gtgtcaaaga aaactgcatt    360
tatcataaga gcatatttaa tggaatgaat tttcctgctg atggacctgt gatgaaaaag    420
atgacaacta actgggaagc atcctgcgag aagatcatgc cagtacctaa gcagggata    480 ctgaaagggg atgtctccat gtacctcctt ctgaaggatg tgggcgtta ccggtgccag    540 ttcgacacag tttacaaagc aaagtctgtg ccaagtaaga tgccggagtg gcacttcatc    600
cagcataagc tcctccgtga agaccgcagc gatgctaaga atcagaagtg gcagctgaca    660
gagcatgcta ttgcattccc ttctgccttg gcctga                             696

<210> SEQ ID NO 5
<211> LENGTH: 699
<212> TYPE: DNA
<213> ORGANISM: Discosoma striata

<400> SEQUENCE: 5
atgagttgtt ccaagagtgt gatcaaggaa gaaatgttga tcgatcttca tctggaagga     60
acgttcaatg ggcactactt tgaaataaaa ggcaaggaa aaggacagcc taatgaaggc    120
accaataccg tcacgctcga ggttaccaag ggtggacctc tgccatttgg ttggcatatt    180
ttgtgcccac aatttcagta tggaaacaag gcatttgtcc accacctga caacatacat    240 gattatctaa agctgtcatt tccggaggga tatacatggg aacggtccat gcactttgaa    300
gacggtggct tgtgttgtat caccaatgat atcagtttga caggcaactg tttctactac    360
gacatcaagt tcactggctt gaactttcct ccaaatggac ccgttgtgca gaagaagaca    420
actggctggg aaccgagcac tgagcgtttg tatcctcgtg atggtgtgtt gataggagac    480
atccatcatg ctctgacagt tgaaggaggt ggtcattacg catgtgacat taaaactgtt    540
tacagggcca agaaggccgc cttgaagatg ccagggtatc actatgttga caccaaactg    600
gttatatgga acaacgacaa agaattcatg aaagttgagg agcatgaaat cgccgttgca    660
cgccaccatc cgttctatga gccaaagaag gataagtaa                          699

<210> SEQ ID NO 6
<211> LENGTH: 678
<212> TYPE: DNA
<213> ORGANISM: Discosoma sp "red"

<400> SEQUENCE: 6
atgaggtctt ccaagaatgt tatcaaggag ttcatgaggt ttaaggttcg catggaagga     60
acggtcaatg gcacgagtt tgaaatagaa ggcgaaggag aggggaggcc atacgaaggc    120
cacaataccg taaagcttaa ggtaaccaag ggggaccttt gccatttgc ttgggatatt    180 ttgtcaccac aatttcagta tggaagcaag gtatatgtca agcaccctgc cgacatacca    240
gactataaaa agctgtcatt tcctgaagga tttaaatggg aaagggtcat gaactttgaa    300
gacggtggcg tcgttactgt aacccaggat tccagtttgc aggatggctg tttcatctac    360
aaggtcaagt tcattggcgt gaactttcct tccgatggac ctgttatgca aagaagaca    420 atgggctggg aagccagcac tgagcgtttg tatcctcgtg atggcgtgtt gaaggagag    480 attcataagg ctctgaagct gaaagacggt ggtcattacc tagttgaatt caaaagtatt    540
```

```
tacatggcaa agaagcctgt gcagctacca gggtactact atgttgactc caaactggat    600
ataacaagcc acaacgaaga ctatacaatc gttgagcagt atgaaagaac cgagggacgc    660
caccatctgt tcctttaa                                                  678
```

<210> SEQ ID NO 7
<211> LENGTH: 801
<212> TYPE: DNA
<213> ORGANISM: Clavularia sp

<400> SEQUENCE: 7

```
atgaagtgta aatttgtgtt ctgcctgtcc ttcttggtcc tcgccatcac aaacgcgaac     60 attttttga gaaacgaggc tgacttagaa gagaagacat tgagaatacc aaaagctcta    120
accaccatgg gtgtgattaa accagacatg aagattaagc tgaagatgga aggaaatgta    180
aacgggcatg cttttgtgat cgaaggagaa ggagaaggaa agccttacga tgggacacac    240
actttaaacc tggaagtgaa ggaaggtgcg cctctgcctt tttcttacga tatcttgtca    300
aacgcgttcc agtacggaaa cagagcattg acaaaatacc agacgatat agcagactat    360 ttcaagcagt cgtttcccga gggatattcc tgggaaagaa ccatgacttt tgaagacaaa    420
ggcattgtca aagtgaaaag tgacataagc atggaggaag actcctttat ctatgaaatt    480
cgttttgatg ggatgaactt tcctcccaat ggtccggtta tgcagaaaaa aactttgaag    540
tgggaaccat ccactgagat tatgtacgtg cgtgatggag tgctggtcgg agatattagc    600
cattctctgt tgctggaggg aggtggccat taccgatgtg acttcaaaag tatttacaaa    660
gcaaaaaaag ttgtcaaatt gccagactat cactttgtgg accatcgcat tgagatcttg    720
aaccatgaca aggattacaa caaagtaacg ctgtatgaga atgcagttgc tcgctattct    780
ttgctgccaa gtcaggccta g                                             801
```

<210> SEQ ID NO 8
<211> LENGTH: 8
<212> TYPE: PRT
<213> ORGANISM: Artificial sequence
<220> FEATURE:
<223> OTHER INFORMATION: Protein localization sequence

<400> SEQUENCE: 8

Pro Pro Lys Lys Lys Arg Lys Val
1               5

<210> SEQ ID NO 9
<211> LENGTH: 28
<212> TYPE: PRT
<213> ORGANISM: Artificial sequence
<220> FEATURE:
<223> OTHER INFORMATION: Protein localization sequence

<400> SEQUENCE: 9

Met Ser Phe Val Ser Leu Leu Leu Val Gly Ile Leu Phe Trp Ala Thr
1               5                   10                  15

Gly Ala Glu Asn Leu Thr Lys Cys Glu Val Phe Asn
            20                  25

<210> SEQ ID NO 10
<211> LENGTH: 4
<212> TYPE: PRT
<213> ORGANISM: Artificial sequence
<220> FEATURE:
<223> OTHER INFORMATION: Protein localization sequence

<400> SEQUENCE: 10

Lys Asp Glu Leu
1

<210> SEQ ID NO 11
<211> LENGTH: 4
<212> TYPE: PRT
<213> ORGANISM: Artificial sequence
<220> FEATURE:
<223> OTHER INFORMATION: Protein localization sequence

<400> SEQUENCE: 11

Lys Lys Ala Ala
1

<210> SEQ ID NO 12
<211> LENGTH: 3
<212> TYPE: PRT
<213> ORGANISM: Artificial sequence
<220> FEATURE:
<223> OTHER INFORMATION: Protein localization sequence

<400> SEQUENCE: 12

Ser Lys Leu
1

<210> SEQ ID NO 13
<211> LENGTH: 25
<212> TYPE: PRT
<213> ORGANISM: Artificial sequence
<220> FEATURE:
<223> OTHER INFORMATION: Protein localization sequence

<400> SEQUENCE: 13

Met Leu Ser Leu Arg Asn Ser Ile Arg Phe Phe Lys Pro Ala Thr Arg
1               5                   10                  15

Thr Leu Cys Ser Ser Arg Tyr Leu Leu
            20                  25

<210> SEQ ID NO 14
<211> LENGTH: 26
<212> TYPE: PRT
<213> ORGANISM: Artificial sequence
<220> FEATURE:
<223> OTHER INFORMATION: Protein localization sequence

<400> SEQUENCE: 14

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 15
<211> LENGTH: 21
<212> TYPE: PRT
<213> ORGANISM: Artificial sequence
<220> FEATURE:
<223> OTHER INFORMATION: Protein localization sequence

<400> SEQUENCE: 15

Met Gly Cys Ile Lys Ser Lys Arg Lys Asp Asn Leu Asn Asp Asp Gly
1               5                   10                  15

Val Asp Met Lys Thr
            20

```
<210> SEQ ID NO 16
<211> LENGTH: 15
<212> TYPE: PRT
<213> ORGANISM: Artificial sequence
<220> FEATURE:
<223> OTHER INFORMATION: Protein localization sequence

<400> SEQUENCE: 16

Lys Lys Lys Lys Lys Lys Lys Ser Lys Thr Lys Cys Val Ile Met
1               5                   10                  15

<210> SEQ ID NO 17
<211> LENGTH: 16
<212> TYPE: PRT
<213> ORGANISM: Artificial sequence
<220> FEATURE:
<223> OTHER INFORMATION: Protein targeting sequence

<400> SEQUENCE: 17

Met Gly Cys Ile Lys Ser Lys Arg Lys Asp Asn Leu Asn Asp Asp Thr
1               5                   10                  15

<210> SEQ ID NO 18
<211> LENGTH: 9
<212> TYPE: PRT
<213> ORGANISM: Artificial sequence
<220> FEATURE:
<223> OTHER INFORMATION: Protein targeting sequence

<400> SEQUENCE: 18

Met Gly Cys Ile Lys Ser Lys Arg Lys
1               5

<210> SEQ ID NO 19
<211> LENGTH: 19
<212> TYPE: PRT
<213> ORGANISM: Artificial sequence
<220> FEATURE:
<223> OTHER INFORMATION: Protein targeting sequence

<400> SEQUENCE: 19

Met Gly Cys Ile Lys Ser Lys Arg Lys Asp Asn Leu Asn Asp Asp Arg
1               5                   10                  15

Arg Arg Thr

<210> SEQ ID NO 20
<211> LENGTH: 75
<212> TYPE: DNA
<213> ORGANISM: Artificial sequence
<220> FEATURE:
<223> OTHER INFORMATION: Oligonucleotide for PCR

<400> SEQUENCE: 20
attcccaagc ttgcggccgc caccatgggc tgcatcaaga gcaagcgcaa ggacaacctg      60
aacgacgacg gcgtg                                                      75

<210> SEQ ID NO 21
<211> LENGTH: 33
<212> TYPE: DNA
<213> ORGANISM: Artificial sequence
<220> FEATURE:
<223> OTHER INFORMATION: Oligonucleotide for PCR

<400> SEQUENCE: 21
```

-continued

```
ccggaattct tacttgtaca gctcgtccat gcc                           33

<210> SEQ ID NO 22
<211> LENGTH: 60
<212> TYPE: DNA
<213> ORGANISM: Artificial sequence
<220> FEATURE:
<223> OTHER INFORMATION: Oligonucleotide for PCR

<400> SEQUENCE: 22
gacaacctga acgacgacgg cgtggacatg aagaccatgg tgagcaaggg cgaggagctg    60
```

DETECTION OF TRANSMEMBRANE POTENTIALS BY OPTICAL METHODS

This is a continuation of U.S. application Ser. No. 09/459,956 filed Dec. 13, 1999, now U.S. Pat. 6,342,379, which claims priority under 35 U.S.C. § 120 of U.S. Continuation-in-Part application Ser. No. 08/765,860, filed May 8, 1997, now issued as U.S. Pat. No. 6,107,066, which entered the national stage from international application PCT/US96/09652, filed Jun. 6, 1996, WHICH IS A CONTINUATION-IN-PART OF Ser. No. 08/481,977 FILED Jun. 7, 1995, NOW ISSUED AS U.S. Pat. No. 5,661,035, the disclosure of each is incorporated by reference in the disclosure of this application.

This invention was made with Government support under Grant No. R01 NS27177-07, awarded by the National Institutes of Health. The Government has certain rights in this invention.

FIELD OF THE INVENTION

The present invention relates generally to compositions and optical methods for determining transmembrane potentials across biological membranes of living cells.

BACKGROUND OF THE INVENTION

Fluorescence detection and imaging of cellular electrical activity is a technique of great importance and potential (Grinvald, A., Frostig, R. D., Lieke, E., and Hildesheim, R. 1988. Optical imaging of neuronal activity. *Physiol. Rev.* 68:1285–1366; Salzberg, B. M. 1983. Optical recording of electrical activity in neurons using molecular probes. In Current Methods in Cellular Neurobiology. J. L. Barker, editor. Wiley, New York. 139–187; Cohen, L. B. and S. Lesher. 1985. Optical monitoring of membrane potential: methods of multisite optical measurement. In Optical Methods in Cell Physiology. P. de Weer and B. M. Salzberg, editors. Wiley, New York. 71–99).

Mechanisms for optical sensing of membrane potential have traditionally been divided into two classes:

(1) sensitive but slow redistribution of permeant ions from the extracellular medium into the cell, and (2) fast but small perturbations of relatively impermeable dyes attached to one face of the plasma membrane. see, Loew, L. M., "How to choose a potentiometric membrane probe", In Spectroscopic Membrane Probes. L. M. Loew, ed., 139–151 (1988) (CRC Press, Boca Raton); Loew, L. M., "Potentiometric membrane dyes", In Fluorescent and Luminescent Probes for Biological Activity. W. T. Mason, ed., 150–160 (1993) (Academic Press, San Diego).

The permeant ions are sensitive because the ratio of their concentrations between the inside and outside of the cell can change by up to the Nernstian limit of 10-fold for a 60 mV change in transmembrane potential. However, their responses are slow because to establish new equilibria, ions must diffuse through unstirred layers in each aqueous phase and the low-dielectric-constant interior of the plasma membrane. Moreover, such dyes distribute into all available hydrophobic binding sites indiscriminately. Therefore, selectivity between cell types is difficult. Also, any additions of hydrophobic proteins or reagents to the external solution, or changes in exposure to hydrophobic surfaces, are prone to cause artifacts. These indicators also fail to give any shift in fluorescence wavelengths or ratiometric output. Such dual-wavelength readouts are useful in avoiding artifacts due to variations in dye concentration, path length, cell number, source brightness, and detection efficiency.

By contrast, the impermeable dyes can respond very quickly because they need little or no translocation. However, they are insensitive because they sense the electric field with only a part of a unit charge moving less than the length of the molecule, which in turn is only a small fraction of the distance across the membrane. Furthermore, a significant fraction of the total dye signal comes from molecules that sit on irrelevant membranes or cells and that dilute the signal from the few correctly placed molecules.

In view of the above drawbacks, methods and compositions are needed which are sensitive to small variations in transmembrane potentials and can respond both to rapid, preferably on a millisecond timescale, and sustained membrane potential changes. Also needed are methods and compositions that are less susceptible to the effects of changes in external solution composition, more capable of selectively monitoring membranes of specific cell types, and within intracellular organelles and providing a ratiometric fluorescence signal.

Such methods require effective methods of discriminating measurements from within defined cell populations, or subcellular structures. This invention fulfils this and related needs.

SUMMARY OF THE INVENTION

Methods and compositions are provided for detecting changes in membrane potential in biological systems. One aspect of the detection method comprises;

a) providing a living cell with a first reagent comprising a charged hydrophobic molecule. Typically the molecule is a fluorescence resonance energy transfer (FRET) acceptor or donor, or is a quencher and is capable of redistributing within the membrane of a biological membrane in response to changes in the potential across the membrane;

b) providing the cell with a second reagent that can label the first face or the second face of a biological membrane within the cell. In one aspect, the second reagent can redistribute from the membrane to other sites in response to changes in the potential of the membrane. Typically the second reagent comprises a luminescent or fluorescent component capable of undergoing energy transfer with the first reagent or quenching light emission of the first reagent;

c) detecting light emission from the first reagent or the second reagent.

In one aspect of this method, the cell is exposed to excitation light at appropriate wavelengths and the degree of energy transfer between the first and second reagents determined. In one contemplated version of this method the excitation light is used to confocally illuminate the cell, thereby providing enhanced spatial resolution. In another aspect this is achieved via the use of two photon excitation.

In another aspect of this method, the cell is exposed to a luminescent or bioluminescent substrate for the luminescent component resulting in light emission from the luminescent component. The degree of energy transfer between the first and second reagent may then be determined by measuring the emission ratios of the first and second reagents, without the need to provide external illumination.

In one aspect of this method, light emission of the first reagent or the second reagent is dependent on the membrane potential across the membrane.

In another aspect of this method, the efficiency of energy transfer from the first reagent to the second reagent is dependent on the voltage potential across the membrane.

In another aspect, the cell additionally comprises an ion channel, receptor, transporter or membrane pore-forming agent that acts to set the membrane potential to a specific value.

Another aspect of the invention involves a method of monitoring subcellular organelle membrane potentials in a living cell comprising;
1) providing a living cell with a first reagent, comprising a hydrophobic, charged fluorescent molecule, and
2) providing the living cell with a second reagent comprising a luminescent or fluorescent component, wherein the luminescent or fluorescent component is targetable to the subcellular membrane, and wherein the second reagent undergoes energy transfer with said first reagent or quenches light emission of the first reagent.

In one aspect of this method the second reagent is targetable to the subcellular membrane through fusion to a protein or peptide that contains a targeting or localization sequence(s). Preferred localization sequences provide for specific localization of the protein to the defined location, with minimal accumulation of the reagent in other biological membranes.

Another aspect of the present invention is a transgenic organism comprising a first reagent that comprises a charged hydrophobic fluorescent molecule, and a second reagent comprising a bioluminescent or naturally fluorescent protein. The bioluminescent or naturally fluorescent protein is typically expressed within the transgenic organism and targetable to a cellular membrane. A second reagent provided to the transgenic organism undergoes energy transfer with the first reagent or quenches light emission of said first reagent. Such transgenic organisms may be used in whole animal studies to monitor drug effects on neuronal activity in vivo or to understand disease states in appropriate model systems.

Another aspect of the invention is a method of screening test chemicals for activity to modulate a target ion channel, involving, providing a living cell comprising a target ion channel, and a membrane potential modulator wherein the membrane potential modulator sets the resting membrane potential to a predefined value between about −150 mV and +100 mV. After contact of the living cell with a test chemical, the membrane potential across the cellular membrane is detected.

These methods are particularly suited for measuring the effects of test chemicals on rapidly inactivated or voltage dependent ion channels. The invention works in one aspect by creating a cell with a defined membrane potential through the expression and regulation of the membrane potential modulator. By providing cells with defined membrane potentials the invention provides for stable assays for rapidly inactivating ion channels, and provides a simple and convenient method of activating voltage dependent ion channels by appropriate regulation of the activity of the membrane potential modulator.

BRIEF DESCRIPTION OF THE DRAWINGS

The invention may be better understood with reference to the accompanying drawings, in which.

DESCRIPTION OF THE PREFERRED EMBODIMENT

Figure 1A:
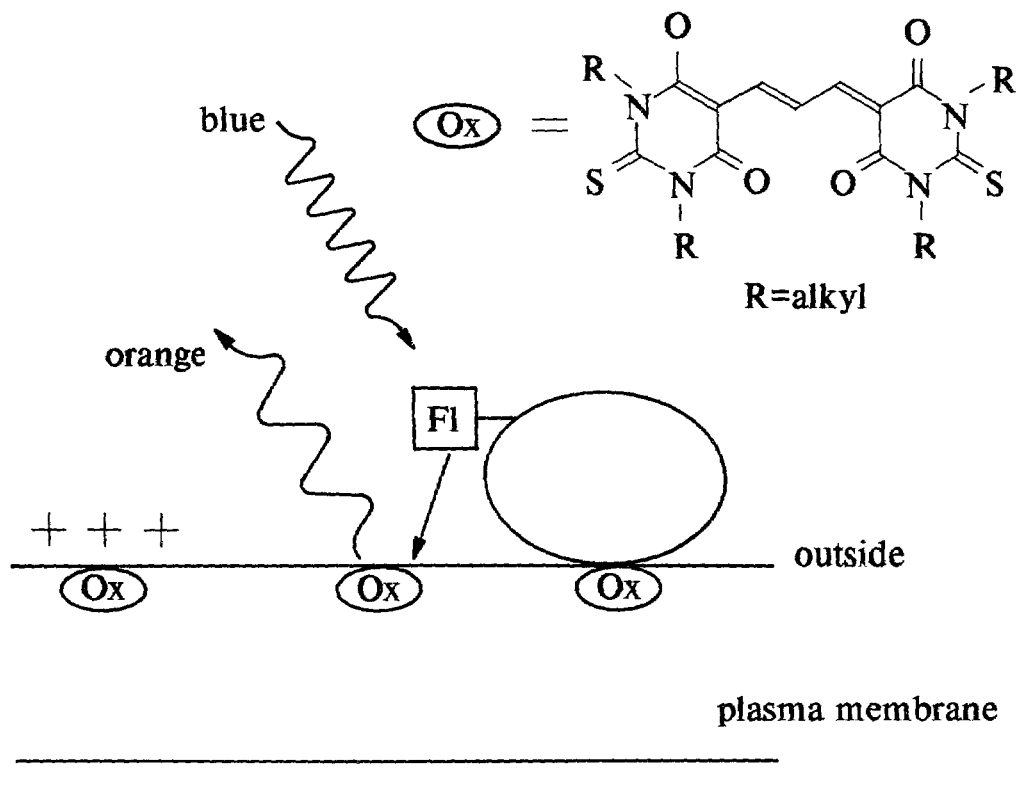
FIGS. 1A and 1B illustrate a scheme of the voltage-sensitive FRET mechanism.

The following definitions are set forth to illustrate and define the meaning and scope of the various terms used to describe the invention herein.

Generally, the nomenclature used herein and many of the fluorescence, computer, detection, chemistry and laboratory procedures described below are those well known and commonly employed in the art. Standard techniques are usually used for chemical synthesis, fluorescence, optics, molecular biology, computer software and integration. Generally, chemical reactions, cell assays and enzymatic reactions are performed according to the manufacturer's specifications where appropriate. The techniques and procedures are generally performed according to conventional methods in the art and various general references. (Lakowicz, J. R. *Topics in Fluorescence Spectroscopy*, (3 volumes) New York: Plenum Press (1991), and Lakowicz, J. R. *Emerging applications of fluorescence spectroscopy to cellular imaging: lifetime imaging, metal-ligand probes, multi-photon excitation and light quenching.* Scanning Microsc Suppl Vol. 10 (1996) pages 213–24, for fluorescence techniques; Sambrook et al. *Molecular Cloning: A Laboratory Manual*, 2$^{nd}$ ed. (1989) Cold Spring Harbor Laboratory Press, Cold Spring Harbor, N.Y., for molecular biology methods; *Cells: A Laboratory Manual*, 1$^{st}$ edition (1998) Cold Spring Harbor Laboratory Press, Cold Spring Harbor, N.Y., for cell biology methods; *Optics Guide* 5 Melles Griot® Irvine Calif., and *Optical Waveguide Theory*, Snyder & Love published by Chapman & Hall for general optical methods, which are incorporated herein by reference and which are provided throughout this document).

As employed throughout the disclosure, the following terms, unless otherwise indicated, shall be understood to have the following meanings:

The term "hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "alkyl" refers to a branched or straight chain acyclic, monovalent saturated hydrocarbon radical of one to twenty carbon atoms.

The term "alkenyl" refers to an unsaturated hydrocarbon radical which contains at least one carbon-carbon double bond and includes straight chain, branched chain and cyclic radicals.

The term "alkynyl" refers to an unsaturated hydrocarbon radical which contains at least one carbon-carbon triple bond and includes straight chain, branched chain and cyclic radicals.

The term "lower" referred to herein in connection with organic radicals or compounds respectively defines such with up to and including six, preferably up to and including four carbon atoms. Such groups may be straight chain or branched.

The term "heteroalkyl" refers to a branched or straight chain acyclic, monovalent saturated radical of two to forty atoms in the chain in which at least one of the atoms in the chain is a heteroatom, such as, for example, oxygen or sulfur.

The term "lower-alkyl" refers to an alkyl radical of one to six carbon atoms. This term is further exemplified by such radicals as methyl, ethyl, n-propyl, isopropyl, isobutyl, sec-butyl, n-butyl and tert-butyl, n-hexyl and 3-methylpentyl.

The term "cycloalkyl" refers to a monovalent saturated carbocyclic radical of three to twelve carbon atoms in the carbocycle.

The term "heterocycloalkyl" refers to a monovalent saturated cyclic radical of one to twelve atoms in the ring, having at least one heteroatom, such as oxygen or sulfur) within the ring.

The term "alkylene" refers to a fully saturated, cyclic or acyclic, divalent, branched or straight chain hydrocarbon radical of one to forty carbon atoms. This term is further exemplified by radicals such as methylene, ethylene, n-propylene, 1-ethylethylene, and n-heptylene.

The term "heteroalkylene" refers to an alkylene radical in which at least one of the atoms in the chain is a heteroatom.

The term "heterocyclo-diyl" refers to a divalent radical containing a heterocyclic ring. The free valences may both be on the heterocyclic ring or one or both may be on alkylene substituents appended onto the ring.

The term "lower-alkylene" refers to a fully saturated, acyclic, divalent, branched or straight chain hydrocarbon radical of one to six carbon atoms. This term is further exemplified by such radicals as methylene, ethylene, n-propylene, i-propylene, n-butylene, i-butylene (or 2-methylpropylene), isoamylene (or 3,3 dimethylpropylene), pentylene, and n-hexylene.

The term "cycloalkyl lower-alkyl" refers to a cycloalkyl group appended to a lower-alkyl radical. This term is exemplified by, but not limited to, groups such as cyclopropylmethyl, cyclopentylmethyl, cyclopentylethyl, and cyclopentylpropyl.

The term "substituted phenyl" refers to a phenyl group which is mono-, di-, tri-,or tetra-substituted, independently, with hydrocarbyl, alkyl, lower-alkyl, cycloalkyl or cycloalkyl-lower alkyl.

The term "aryl" refers to an aromatic monovalent carbocyclic radical having a single ring (e.g., phenyl) or multiple condensed rings (e.g., naphthyl, anthracenyl), which can optionally be mono-, di-, or tri-substituted, independently, with hydrocarbyl, alkyl, lower-alkyl, cycloalkyl or cycloalkyl lower alkyl.

The term "arylene" refers to an aromatic divalent carbocyclic radical. The open valence positions may be at any position on the ring(s). In the case of a divalent phenyl radical, they may be ortho, meta or para to each other.

The term "aralkyl" refers to an aryl group appended to a lower-alkyl radical. This term is exemplified by, but not limited to, groups such as benzyl, 2-phenylethyl and 2-(2-naphthylethyl).

The term "aralkenyl" refers to an aryl group appended to a fully conjugated alkenyl radical. This term is exemplified by styrenyl (cis and trans) and 1-phenyl butadienyl and 1-naphthyl butadienyl (including all possible combinations of the Z and E isomers about the double bonds).

The term "halo" refers to fluoro, bromo, chloro and iodo.

The term "lower-alkylthio" refers to the group R—S—, where R is lower-alkyl.

The term "leaving group" means a group capable of being displaced by a nucleophile in a chemical reaction, for example halo, alkyl sulfonates (e.g., methanesulfonate), aryl sulfonates, phosphates, sulfonic acid, sulfonic acid salts, imidazolides, N-hydroxy succinimides and the like.

The term "linker" refers to any chemically and biologically compatible covalent grouping of atoms which can serve to link together the first and second reagents of this invention. Generally, preferred linkers have from 20 to 40 bonds from end to end, preferably 25 to 30 bonds, and may be branched or straight chain or contain rings. The bonds may be carbon-carbon or carbon-heteroatom or heteroatom-heteroatom bonds. The linkage can be designed to be hydrophobic or hydrophilic. The linking group can contain single and/or double bonds, 0–10 heteroatoms (O, S preferred), and saturated or aromatic rings. The linking group may contain groupings such as ester, ether, sulfide, disulfide and the like.

The term "amphiphilic" refers to a molecule having both a hydrophilic and a hydrophobic portion.

The term "bioluminescent protein" refers to a protein capable of causing the emission of light through the catalysis of a chemical reaction. The term includes proteins that catalyze bioluminescent or chemiluminescent reactions, such as those causing the oxidation of luciferins. The term "bioluminescent protein" includes not only bioluminescent proteins that occur naturally, but also mutants that exhibit altered spectral or physical properties.

The term "fluorescent component" refers to a component capable of absorbing light and then re-emitting at least some fraction of that energy as light over time. The term includes discrete compounds, molecules, naturally fluorescent proteins and marco-molecular complexes or mixtures of fluorescent and non-fluorescent compounds or molecules. The term "fluorescent component" also includes components that exhibit long lived fluorescence decay such as lanthanide ions and lanthanide complexes with organic ligand sensitizers, that absorb light and then re-emit the energy over milliseconds.

The term "FRET" refers to fluorescence resonance energy transfer. For the purposes of this invention, FRET refers to energy transfer processes that occur between two fluorescent components, a fluorescent component and a non-fluorescent component, a luminescent component and a fluorescent component and a luminescent component with a non-fluorescent component.

The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination.

The term "heterologous" refers to a nucleic acid sequence that either originates from another species or is modified from either its original form or the form primarily expressed in the cell.

The term "homolog" refers to two sequences or parts thereof, that are greater than, or equal to 75% identical when optimally aligned using the ALIGN program. Homology or sequence identity refers to the following. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure,* 1972, volume 5, National Biomedical Research Foundation, pp. 101–110, and Supplement 2 to this volume, pp. 1–10.

The term "luminescent component" refers to a component capable of absorbing energy, such as electrical (e.g. Electroluminescence), chemical (e.g. chemi-luminescence) or acoustic energy and then emitting at least some fraction of that energy as light over time. The term "component" includes discrete compounds, molecules, bioluminescent proteins and marco-molecular complexes or mixtures of luminescent and non-luminescent compounds or molecules that act to cause the emission of light.

The term "membrane potential modulator" refers to components capable of altering the resting or stimulated membrane potential of a cellular or subcellular compartment. The term includes discrete compounds, ion channels, receptors, pore forming proteins or any combination of these components.

The term "naturally fluorescent protein" refers to a protein capable of forming a highly fluorescent, intrinsic chromophore either through the cyclization and oxidation of internal amino acids within the protein or via the enzymatic addition of a fluorescent co-factor. The term includes wild-type fluorescent proteins and engineered mutants that exhibit altered spectral or physical properties. The term does not include proteins that exhibit weak fluorescence by virtue only of the fluorescence contribution of non-modified tyrosine, tryptophan, histidine and phenylalanine groups within the protein.

The term "Naturally occurring" refers to a component produced by cells in the absence of artifical genetic or other modifications of those cells.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The term "targetable" refers to a component that has the ability to be localized to a specific location under certain conditions. For example, a protein that can exist at two or more locations that has the ability to translocate to a defined site under some condition(s) is targetable to that site. Common examples include the translocation of protein kinase C to the plasma membrane upon cellular activation, and the binding of SH2 domain containing proteins to phosphorylated tyrosine residues. The term includes components that are persistently associated with one specific location or site, under most conditions.

The term "test chemical" refers to a chemical to be tested by one or more screening method(s) of the invention as a putative modulator. A test chemical can be any chemical, such as an inorganic chemical, an organic chemical, a protein, a peptide, a carbohydrate, a lipid, or a combination thereof. Usually, various predetermined concentrations of test chemicals are used for screening, such as 0.01 micromolar, 1 micromolar and 10 micromolar. Test chemical controls can include the measurement of a signal in the absence of the test compound or comparison to a compound known to modulate the target.

The term "transformed" refers to a cell into which (or into an ancestor of which) has been introduced, by means of recombinant nucleic acid techniques, a heterologous nucleic acid molecule.

The term "transgenic" is used to describe an organism that includes exogenous genetic material within all of its cells. The term includes any organism whose genome has been altered by in vitro manipulation of the early embryo or fertilized egg or by any transgenic technology to induce a specific gene knockout.

The term "transgene" refers any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes of the invention include DNA sequences that encode the fluorescent or bioluminescent protein that may be expressed in a transgenic non-human animal.

The following terms are used to describe the sequence relationships between two or more polynucleotides: "reference sequence", "comparison window", "sequence identity", "percentage identical to a sequence", and "substantial identity". A "reference sequence" is a defined sequence used as a basis for a sequence comparison; a reference sequence may be a subset of a larger sequence, for example, as a segment of a full-length cDNA or gene sequence given in a sequence listing such as a SEQ. ID. NO: 1, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage identical to a sequence" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 30 percent sequence identity, preferably at least 50 to 60 percent sequence identity, more usually at least 60 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 30 percent sequence identity, preferably at least 40 percent sequence identity, more preferably at least 50 percent sequence identity, and most preferably at least 60 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise. For example, reference to a "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

Before the present sequences, variants, formulations and methods for making and using the invention are described, it is to be understood that the invention is not to be limited only to the particular sequences, variants, formulations or methods described. The sequences, variants, formulations and methodologies may vary, and the terminology used herein is for the purpose of describing particular embodiments. The terminology and definitions are not intended to be limiting since the scope of protection will ultimately depend upon the claims.

The compositions used in the methods of the invention typically comprise two reagents. The first reagent comprises a mobile hydrophobic molecule that rapidly redistributes within the biological membrane in response to changes in transmembrane potential. Typically the first reagent is charged and preferably positively charged under the physiological conditions within a living cell. This species is referred to as the mobile or hydrophobic molecule. The second reagent comprises a luminescent or fluorescent component that is capable of undergoing energy transfer with the first reagent, typically by donating excited state energy to the mobile fluorescent molecule. In the case where the second reagent is a fluorescent component, it may also be capable accepting excited state energy from the mobile fluorescent molecule.

The first and second reagents are spectroscopically complementary to each other, by which is meant that their spectral characteristics are such that excited state energy transfer can occur between them. Either reagent can function as the donor or the acceptor, in which case the other reagent is the corresponding complement, i.e., the acceptor or donor respectively. Both FRET and quenching are highly sensitive to the distance between the two species. For example, the nonradiative Forster-type quenching observed in FRET varies inversely with the sixth power of the distance between the donor and acceptor species. Therefore, when the membrane potential changes and the hydrophobic fluorescent molecule moves either further away from or closer to the second reagent, FRET between the two reagents is either reduced or enhanced significantly. Other mechanisms such as electron-transfer, Dexter exchange interaction, paramagnetic quenching, and promoted intersystem crossing are even shorter-range and require the two reagents to collide or at least come within 1 nm of each other.

The present invention includes voltage assays that derive at least some part of the measurable signal from non-FRET derived changes in light emission from either the first or second reagent. Such changes in light emission can occur as a direct or indirect effect of the transmembrane potential on the fluorescent or luminescent properties of first or second reagent. For example, translocation of a fluorescent dye into or out of the lipid bilayer can cause significant alterations in the molar extinction coefficient and quantum yield of the dye that can be exploited to significantly amplify a FRET signal.

Naturally fluorescent proteins have been successfully fused to a range of proteins and in some cases these have been demonstrated to provide conformation sensitive changes in the fluorescent properties of the fluorescent protein (for example see PCT publication WO 98/30715). Such changes in protein conformation can result in alterations in the optical properties of the fluorescent or bioluminescent protein that can be used to measure a membrane potential change. Significantly larger and more specific signal changes in response to a given transmembrane change may further be provided by combining the approach with the use of FRET to a second fluorophore.

Previously reported voltage-sensitive fluorescent indicators operating by potential-driven redistribution of the fluorophore across the membrane had response times of >100 ms, often as long as minutes. One aspect of the present invention provides highly fluorescent anionic dyes which translocate across the membrane at much faster rates, with exponential time constants typically less than about 10 ms, frequently less than 5 ms, most frequently from about 1 to 3 ms and most preferably less than 1 ms time scale (e.g., 0.1 to 1 ms). These translocation rates are independent of the presence of the second reagent on the extracellular surface of the membrane. Response times of <1 ms are necessary for accurate measurement of single action potentials in individual neurons and are obtained with some of the dyes described herein (e.g., hexyl-substituted pentamethineoxonol, diSBA-$C_6$-(5)). Other dyes described herein have response times in the 2–5 ms range, which are fast enough to monitor voltage changes in heart and smooth muscle, many synaptic potentials in single neurons, and the average firing activity in populations of neurons (for example, mapping the electrical responses of different regions of the central nervous system to sensory inputs).

The indicators of the present invention are able to follow both rapid and slower voltage changes over a time scale of seconds to minutes.

I. First Reagent—Mobile Hydrophobic Molecules

In the compositions and methods of the present invention, the first reagent comprises a hydrophobic ion (fluorescence donor, acceptor, or quencher) which serves as a voltage sensor and moves within the membrane in response to changes in the transmembrane potential. The distribution of hydrophobic ions between the two membrane-aqueous interfaces (the extracellular interface and the intracellular interface, in the case of the plasma membrane) is determined by the membrane potential. Cations will tend to congregate at the negatively charged membrane interface and correspondingly, anions will move to the positively charged interface. The inherent sensitivity of the invention is based on the large interfacial concentration changes of the mobile ion at physiologically relevant changes in membrane potentials. Potentially, a 60 mV change produces 10-fold change in the ratio of the anion concentrations at the respective interfaces. The methods of this invention couple this change in interfacial concentration to an efficient fluorescent readout thus providing a sensitive method of detecting changes in transmembrane potential. The speed of the fluorescence change is dependent on the membrane translocation rate of the hydrophobic ion.

Preferably, the mobile ions that translocate across the biological membrane are hydrophobic in order to bind strongly to the membrane and translocate rapidly across it in response to changes in transmembrane potential. Preferably, the ion will have a single charge which will be delocalized across a significant portion of the dye, preferably the entire dye. Delocalization of the charge reduces the Born charging energy (inversely proportional to anion radius) required to move a charged molecule from a hydrophilic to a hydrophobic environment and facilitates rapid translocation of ions (Benz, R. 1988. "Structural requirement for the rapid movement of charged molecules across membranes", *Biophys. J.* 54:25–33). Increasing hydrophobicity minimizes release of the bound dye from the plasma membrane and buries the ion deeper into the membrane, which decreases the electrostatic activation energy for translocation. Polar groups on the ion should be kept to a minimum and shielded as much as possible to disfavor solvation in the headgroup region of the bilayer. However, hydrophobicity cannot be increased without limit, because some aqueous solubility is required to permit cellular loading. If necessary, dyes may be loaded with the aid of amphiphilic solubilizing reagents such as beta-cyclodextrin, Pluronics such as Pluronic F-127, or polyethylene glycols such as PEG400, which help solubilize the hydrophobic ions in aqueous solution.

The term "hydrophobic" when used in the context of the hydrophobic ion refers to a species whose partition coefficient between a physiological saline solution (e.g. HBSS) and octanol is preferably at least about 50, and more preferably at least about 1000. Its adsorption coefficient to a phospholipid bilayer (such as for example a membrane derived from a human red blood cell is at least about 100 nm, preferably at least about 300 nm (where the membrane is 3 nm). Methods of determining partition coefficients and adsorption coefficients are known to those of skill in the art.

It is generally preferred that the hydrophobic dye be an anionic species. Ester groups of biological membranes generate a sizable dipole potential within the hydrocarbon core of the membrane. This potential aids anion translocation through the hydrophobic layer but hinders cations. Therefore, where membrane translocation is concerned, anions have a tremendous inherent speed advantage over cations. For example, it is known that for the isostructural ions tetraphenylphosphonium cation and tetraphenylborate anion, the anion is much more permeable than the cation (Flewelling, R. F. and Hubbell, W. L. 1986. "The membrane dipole potential in a total membrane potential model", *Biophys. J.* 49:541–552).

In one embodiment, the anions should be strongly fluorescent when adsorbed to the membrane, whereas they should have minimal fluorescence when free in aqueous solution. Preferably, the anionic fluorophores should be at least four times, and more preferably at least about eight times, brighter when adsorbed to the membrane. In the case of the thiobarbiturate oxonols described herein, their fluorescence is about 20 fold greater in the membrane than in water. In principle, if the dye bound extremely tightly to the membrane one would not need a high ratio of fluorescence when bound to the membrane to that when free in aqueous solution; however, because in reality the volume of the membrane is tiny relative to the aqueous solution and some water solubility is necessary for loading of the dye into cells and tissue, it is desirable for the first reagent to be at least about four times more strongly fluorescent in a membrane than in aqueous solution.

The anions also should not act as ionophores, especially protonophores, since such behavior may generate sustained leakage currents. Therefore, the protonation pKa of the anion is typically well below 7, preferably below 5, more preferably below 3. Red to infra-red wavelengths of excitation and emission are preferred to avoid tissue scattering and heme absorbances. Photodynamic damage should be kept as low as possible, probably best by minimizing triplet state formation and the resulting generation of singlet oxygen.

Fluorescent hydrophobic ions include polymethine oxonols, tetraaryl borates conjugated to fluorophores and fluorescent complexes of rare earth and transition metals.

A. Polymethine Oxonols

The term "polymethine oxonol" refers to molecules comprising two potentially acidic groups linked via a polymethine chain and possessing a single negative charge delocalized between the two acidic groups. The preferred acidic groups are barbiturates or thiobarbiturates. They may be symmetric or asymmetric, i.e., each of the two (thio)barbiturates may be the same or different. The symmetric (thio) barbiturate oxonols are described by the conventional shorthand DiBA-$C_n$-(x) and DiSBA-$C_n$-(x), where DiBA refers to the presence of two barbiturates, DiSBA refers to the presence of two thiobarbiturates, $C_n$ represents alkyl substituents having n carbon atoms on the nitrogen atoms of the (thio) barbiturates, and x denotes the number of carbon atoms in the polymethine chain linking the (thio)barbiturates. It has been unexpectedly found that oxonols with long chain alkyl substituents (e.g. $C_n$ greater than hexyl, especially decyl in the pentamethine oxonols) translocate surprisingly rapidly across plasma membranes.

An extremely useful property of these oxonols is that their fluorescence emission maximum at 560 nm is 20 times brighter when bound to membranes than in aqueous solution [Rink, T. J., Montecucco, C., Hesketh, T. R., and Tsien, R. Y. 1980. Lymphocyte membrane potential assessed with fluorescent probes. *Biochim Biophys. Acta* 595:15–30]. Furthermore, the negative charge is delocalized throughout the chromophore with the four equivalent oxygens containing the majority of the charge. The high electron affinity of the thiobarbiturate moieties discourages protonation, pKa <1, and resists photooxidative bleaching. The four N-alkyl groups and the thiocarbonyl give the molecule a necessary amount of hydrophobicity needed for tight membrane binding and rapid translocation.

Oxonol compounds used in this invention have a general structure of Formula I.

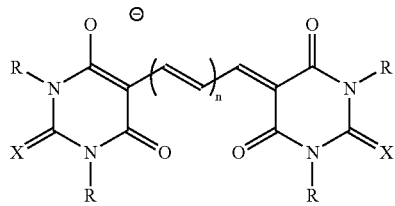

Formula 1 wherein:
R is independently selected from the group consisting of H, hydrocarbyl and heteroalkyl;
X is independently oxygen or sulfur; and
n is an integer from 1 to 3;
and salts thereof.

The oxonol anions are usually loaded as salts with the cation typically being $H^+$, alkali metal, substituted ammonium, or pyridinium.

Preferably X is sulfur, i.e., the hydrophobic anion is a bis-(1,3-dialkyl-2-thiobarbiturate)-polymethine oxonol or a derivative thereof.

When R is a hydrocarbyl group, it can be independently selected from the group consisting of alkyl, cycloalkyl and cycloalkyl lower-alkyl. Typically, these groups have from about 2 to about 40 carbon atoms, more preferably, about 5 to about 20 carbon atoms. R can be also an aryl or aralkyl group. Aryl groups can be substituted with hydrocarbyl, alkyl, lower alkyl, heteroalkyl and halogen groups. Oxonols in which the R groups on a particular (thio)barbiturate moiety are different from each other are specifically contemplated by this invention and can be prepared from unsymmetrical urea derivatives.

In some embodiments, R is a hydrocarbyl group of the formula:

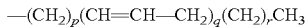

wherein:
p is an integer from 1 to about 20 (preferably about 1 to 2);
q is an integer from 1 to about 6, preferably about 1 to 2;
the stereochemistry of the double bonds may be cis or trans, cis being preferred;
r is an integer from 1 to about 20 (preferably about 1 to 3), and p+3q+r+1 is less than about 40, preferably from about 4 to 20, more preferably about 6 to 10.

In another embodiment of the polymethine oxonols, R is a heteroalkyl group of the formula:

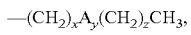

wherein:
A is oxygen or sulfur;
x is independently an integer from 1 to about 20 (preferably about from about 10 to 15);
y is independently 0 or 1;
z is independently an integer from 1 to about 20 (preferably about 5 to 10);
and x+y+z<40, preferably x+y+z=an integer from about 4 to 25, more preferably about 4 to 10.

In other embodiments, R is a phenyl group independently substituted with up to four substituents selected from the group consisting of hydrocarbyl, heteroalkyl, halogen and H.

In other embodiments, one of the four R groups incorporates a linker to the second reagent, as described below.

An oxonol's negative charge is distributed over the entire the chromophore. Bis(thiobarbiturate)trimethineoxonols absorb at 542 nm (ext. coefficient=200,000 $M^{-1}$ $cm^{-1}$), emit at 560 nm and have a quantum yield of 0.4 in octanol. An oxonol where R=n-hexyl, DiSBA-$C_6$-(3), translocates with a time constant ( ) <3 ms in voltage clamped mammalian cells. The corresponding decyl compound, DiSBA-$C_{10}$-(3), translocates with a time constant <2 ms. The molecular requirement for rapid translocation is nicely met with the symmetric oxonols. Bis(thiobarbiturate)pentamethineoxonols absorb at ~630 nm and emit at ~660 nm. The negative charge is further delocalized in such red-shifted oxonols. As expected, the translocation rates for the pentamethine oxonols are faster than for the trimethine oxonols. DiSBA-$C_4$-(5) crosses the membrane with <3 ms, six times faster than the corresponding trimethine oxonol. DiSBA-$C_6$-(5) translocates with ~0.4 ms at 20.

B. Tetraaryl Borate—Fluorophore Conjugates

Another useful class of fluorescent hydrophobic anions are tetraaryl borates having a general structure of Formula II.

Formula II wherein:
$Ar^1$ is an aryl group;
$Ar^2$ is a bifunctional arylene group;
B is boron;
Y is oxygen or sulfur; and
FLU is a neutral fluorophore.

Frequently $Ar^1$ is substituted with one or two electron withdrawing groups, such as but not limited to $CF_3$. In selected embodiments, $Ar^1$ and $Ar^2$ are optionally substituted phenyl groups as shown below for the structure of Formula III.

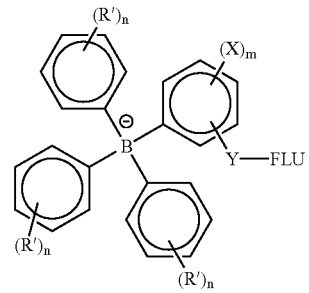

Formula III wherein:
each R' is independently H, hydrocarbyl, halogen, $CF_3$ or a linker group;
n is an integer from 0 to 5;
each X is independently H, halogen or $CF_3$;
m is an integer from 0 to 4;
Y is oxygen or sulfur; and
FLU is a neutral fluorophore.

When R' is hydrocarbyl, it is typically from 1 to about 40 carbon atoms, preferably 3 to about 20 carbon atoms, more preferably about 5 to 15 carbon atoms. Preferably, R' is a lower alkyl group, more preferably (for ease of synthesis) all the R's are H. When R' is not hydrocarbyl, it is frequently $CF_3$ and n=1. In selected embodiments X=F and m=4. X is typically electron-withdrawing to prevent photoinduced electron transfer from the tetraaryl borate to the fluorophore, which quenches the latter. X=F is most preferred.

1. Synthesis of Tetraaryl Borate—Fluorophore Conjugates

Figure 10:
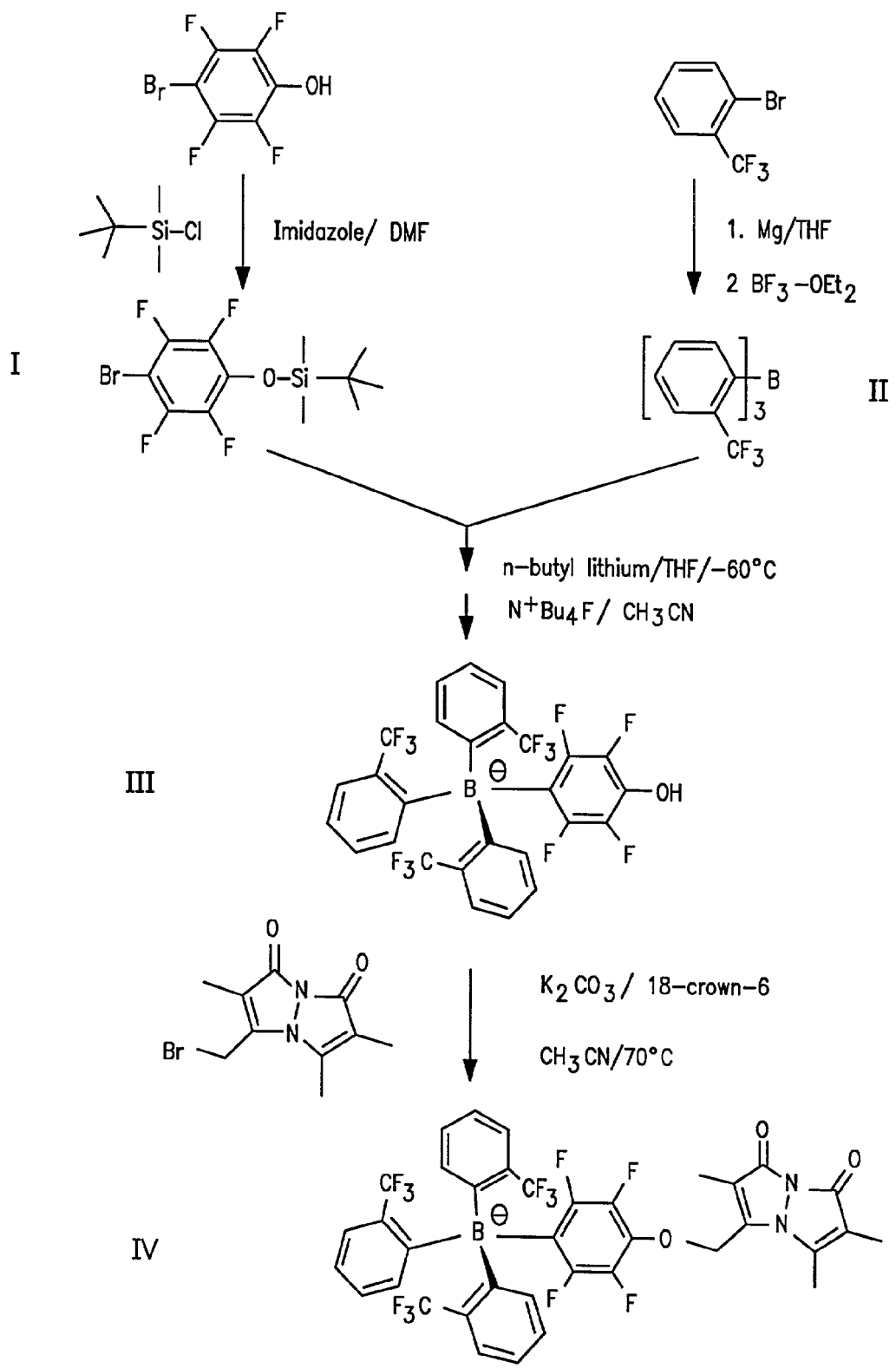
FIG. 10 shows the synthesis of a fluorescent tetraaryl borate.

A general synthesis of fluorescent tetraaryl borate anions has been developed and is shown in FIG. 10 for an exemplary fluorescent bimane tetraaryl borate conjugate (identified as Bormane, compound IV in FIG. 10).

In general terms, a triaryl borane is reacted with a protected phenoxy or thiophenoxy organometallic reagent, such as, for example, an organolithium derivative. The protecting group is subsequently removed and the unmasked phenol (or thiophenol) is reacted with a fluorophore bearing a leaving group. Nucleophilic displacement of the leaving group followed by conventional purification of the crude reaction product furnishes the tetraaryl borate anion conjugated to the fluorophore. Substituents R' and X are varied by appropriate choice of the starting triaryl borane and the phenoxy (or thiophenoxy) organometallic. Suitable starting materials can be obtained from Aldrich Chemical Co. (Milwaukee, Wis.) and other commercial suppliers known to those of skill in the art. Thus in these species, a fluorophore is conjugated to a functionalized borate core. This general synthetic method allows one to attach any fluorophore to the borate anion.

2. Neutral Fluorophores

As polar chromophores retard the membrane translocation rate, it is preferred that the fluorophore conjugated to the tetraaryl borate be a neutral species. For purposes of the present invention, a neutral fluorophore may be defined as a fluorescent molecule which does not contain charged functional groups. Representative fluorescent molecules bearing leaving groups and suitable for conjugation are available from Molecular Probes (Portland, Oreg.), Eastman Kodak (Huntington, Tenn.), Pierce Chemical Co. (Rockville, Md.) and other commercial suppliers known to those of skill in the art. Alternatively, leaving groups can be introduced into fluorescent molecules using methods known to those of skill in the art.

Particularly suitable classes of neutral fluorophores which can be conjugated to the tetraaryl borates for use in accordance with the present invention include, but are not limited to, the following bimanes; bodipys; and coumarins.

Bodipys (i.e., difluoroboradiazaindacenes) may be represented by a general structure of Formula IV.

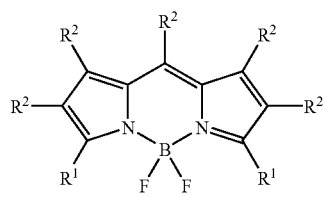

Formula IV wherein:

each $R^1$, which may be the same or different, is independently selected from the group consisting of H, lower alkyl, aryl, heteroaromatic, aralkenyl and an alkylene attachment point;

each $R^2$, which may be the same or different, is independently selected from the group consisting of H, lower alkyl, phenyl and an alkylene attachment point.

For the purposes of this disclosure, the term "alkylene attachment point" refers to the group $—(CH_2)_t—$ or $—(CH_2)_t—C(O)—$ wherein, t is an integer from 1 to 10, and one valence bond is attached to the fluorophore and the other valence bond is attached to the tetraaryl borate. Preferably, t=1, i.e. the alkylene attachment point is a methylene group. As will be apparent to one of skill in the art, all fluorophores will possess one attachment point at which they will be conjugated to the tetraaryl borate. Generally, the precursor molecule used to conjugate the fluorophore to the tetraaryl borate will carry a leaving group at the attachment point. Reaction of this precursor with an appropriate nucleophile on the tetraaryl borate (e.g., an amine, hydroxy or thiol), will provide a fluorophore-tetraaryl borate conjugate linked together at the attachment point. The term "attachment point" refers more broadly to a chemical grouping which is appropriate to react with either a fluorophore or a bifunctional linker to form the fluorescent conjugates and/or linked first and second reagents as disclosed herein. Frequently, these attachment points will carry leaving groups, e.g., alkyl tosylates, activated esters (anhydrides, N-hydroxysuccinimidyl esters and the like) which can react with a nucleophile on the species to be conjugated. One of skill will recognize that the relative positioning of leaving group and the nucleophile on the molecules being linked to each other can be reversed.

Coumarins and related fluorophores may be represented by structures of general Formulas V and VI

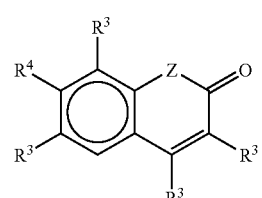

Formula V

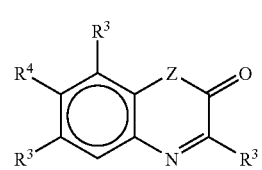

Formula VI wherein:

each $R^3$, which may be the same or different, is independently selected from the group consisting of H, halogen, lower alkyl, CN, $CF_3$, $COOR^5$, $CON(R^5)_2$, $OR^5$, and an attachment point;

$R_4$ is selected from the group consisting of $OR^5$ and $N(R^5)_2$;

Z is O, S or $NR^5$; and each $R^5$, which may be the same or different, is independently selected from the group consisting of H, lower alkyl and an alkylene attachment point.

Bimanes may be represented by a structure of general Formula VII.

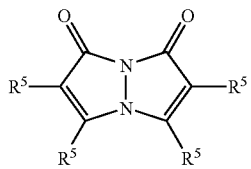

Formula VII wherein:

each $R^5$, which may be the same or different, is independently H, lower alkyl or an alkylene attachment point.

Fluorescent tetraaryl borates with coumarins and bimanes attached have been prepared. These fluorescent borates translocate with <3 ms in voltage clamped fibroblasts. Synthesis of an exemplary fluorescent tetraryl borate is described in Example V.

C. Fluorophore Complexes with Transition Metals

Lanthanide ions, such as, for example, $Tb^{3+}$ and $Eu^{3+}$, luminesce in the green and red regions of the visible spectrum with millisecond lifetimes. The emission is composed of several sharp bands that are indicative of the atomic origin of the excited states. Direct excitation of the ions can be accomplished using deep UV light. Excitation of the lanthanide ions at longer wavelengths is possible when the ions are chelated by absorbing ligands that can transfer excitation energy to the ions, which then can luminesce with their characteristic emission as if they had been excited directly. Lanthanide complexes of $Tb^{3+}$ and $Eu^{3+}$ with absorbing ligands that contribute 4 negative charges, resulting a net charge of −1, may function as mobile ions for the voltage-sensitive FRET mechanism. The lifetimes of $Tb^{3+}$ and $Eu^{3+}$ are still sufficiently fast to measure millisecond voltage changes.

This invention also provides such complexes which can function the fluorescent hydrophobic anion (as FRET donors) in the first reagent. Using the ligand bis-(salicylaldehyde)ethylenediamine $(Salen)^{2-}$, $[Tb(Salen)_2]^{-1}$ and $[Eu(Salen)^2]^{-1}$ have been made. These complexes absorb maximally at 350 nm with significant absorbance up to 380 nm and luminesce with the characteristic atomic emission, FIG. 10. The use of lanthanide complexes as donors offers several unique advantages. Scattering, cellular autofluorescence, and emission from directly excited acceptors have nanosecond or shorter lifetimes and may be rejected by time gating of the emission acquisition (See for example Marriott, G., Heidecker, M., Diamandis, E. P., Yan-Marriott, Y. 1994. Time-resolved delayed luminescence image microscopy using an europium ion chelate complex. *Biophys. J.* 67: 957–965). The elimination of the fast emission reduces the background and gives excellent signal to noise ratios. Another major advantage of using lanthanide chelates as donors is that the range of FRET is amplified by lateral diffusion in the membrane during the excited state lifetime (Thomas, D. D., Carlsen, W. F., Stryer, L. 1978. Fluorescence energy transfer in the rapid diffusion limit. *Proc. Natl. Acad. Sci. USA* 75: 5746–5750). This feature greatly reduces the need for high concentrations of acceptors to ensure efficient FRET. In addition to reducing the perturbation and stress to the cellular system from high dye concentrations, the diffusion enhanced FRET will lead to greater voltage sensitivity than is possible in a static case. Lanthanide chelates can also be used as asymmetrically labeled donors to mobile acceptors such as the tri and pentamethine oxonols, with the same advantages as discussed above.

Representative lanthanide complexes which may be used as a hydrophobic fluorescent anion are shown in Formulas XI and XII

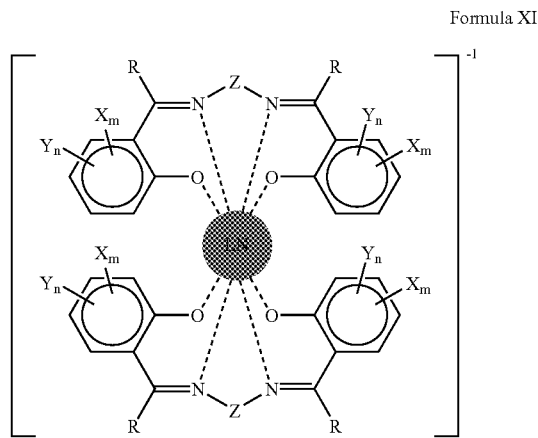

Formula XI wherein:

Ln=Tb, Eu, or Sm;

R is independently H, C1–C8 alkyl, C1–C8 cycloalkyl or C1–C4 perfluoroalkyl;

X and Y are independently H, F, Cl, Br, I, $NO_2$, $CF_3$, lower (C1–C4) alkyl, CN, Ph, O-(lower alkyl), or OPh; or X and Y together are —CH=CH—; and Z=1,2-ethanediyl, 1,3-propanediyl, 2,3-butanediyl, 1,2-cyclohexanediyl, 1,2-cyclopentanediyl, 1,2-cycloheptanediyl, 1,2-phenylenediyl, 3-oxa-1,5-pentanediyl, 3-aza-3-(lower alkyl)-1,5-pentanediyl, pyridine-2,6-bis(methylene) or tetrahydrofuran-2,5-bis(methylene).

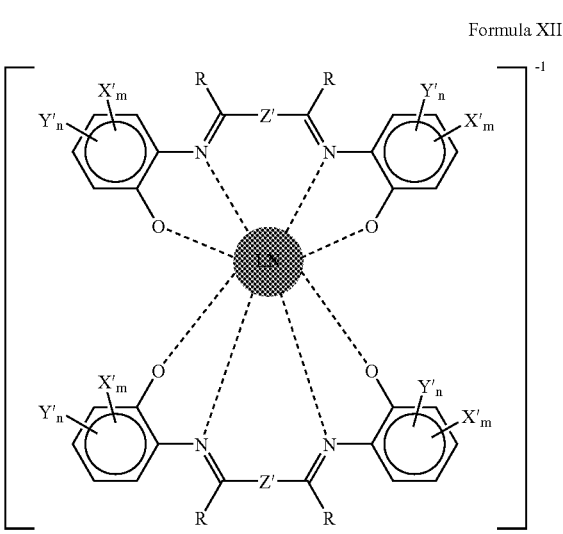

Formula XII wherein:

Ln=Tb, Eu, or Sm;

R is independently H, C1–C8 alkyl, C1–C8 cycloalkyl or C1–C4 perfluoroalkyl;

X' and Y' are independently H, F, Cl, Br, I, $NO_2$, $CF_3$, lower (C1–C4) alkyl, CN, Ph, O-(lower alkyl), or OPh; or X' and Y' together are —CH=CH—; and Z' is independently a valence bond, $CR_2$, pyridine-2-6-diyl or tetrahydofuran-2,5-diyl.

II. Targetable, Asymmetrically Bound Second Reagents

The second reagent is a luminescent or fluorescent donor, acceptor, or quencher, complementary to the first reagent, the hydrophobic molecule, and is targetable to either the extracellular or intracellular face of the biological membrane. Thus, the presence of the second reagent on one or the other face of the membrane desymmetrizes the membrane. As described earlier, energy transfer between the first and second reagent provides an optical readout read out which changes in response to movement of the hydrophobic within the biological membrane.

As would be immediately apparent to those skilled in the field, there are numerous molecular species that could function as the luminescent or fluorescent component and serve as the active desymmetrizing agent. The primary characteristics for this component are that it is located on one face of the biological membrane and function in a complementary manner (i.e., as a fluorescent donor, acceptor, or quencher) to the hydrophobic ion which shuttles back forth across the membrane as the transmembrane potential changes.

Exemplary fluorescent second reagents include fluorescent lectins, fluorescent lipids, fluorescent carbohydrates with hydrophobic substituents, naturally fluorescent proteins or homologs thereof, fluorescently labelled antibodies against surface membrane constituents, or xanthenes, cyanines and coumarins with hydrophobic and hydrophilic substituents to promote binding to membranes and to prevent permeation through membranes.

Exemplary luminescent second reagents include chemi-luminescent, electro-luminescent and bioluminescent compounds. Preferred bioluminescent compounds include bioluminescent proteins such as firefly, bacterial or click beetle luciferases, aequorins and other photoproteins, such as Cypridina luciferase.

A. Fluorescent Lectins

One class of second reagents are lectins carrying a fluorescent label. For purposes of the present invention, a lectin may be defined as a sugar binding protein which binds to glycoproteins and glycolipids on the extracellular face of the plasma membrane. See, Roth, J., "The Lectins: Molecular Probes in Cell Biology and Membrane Research," *Exp. Patholo.* (*Supp.* 3), (Gustav Fischer Verlag, Jena, 1978). Lectins include Concavalin A; various agglutinins (pea agglutinin, peanut agglutinin, wheat germ agglutinin, and the like); Ricin, A chain and the like. A variety of lectins are available from Sigma Chemical Co., St. Louis, Mo.

Suitable fluorescent labels for use in fluorescent lectins include, but are not limited to, the following: xanthenes (including fluoresceins, rhodamines and rhodols); bodipys, cyanines, and luminescent transition metal complexes. It will be recognized that the fluorescent labels described below can be used not merely with lectins but with the other second reagents described herein. To date, the best results with lectins have been obtained with fluorescein labeled wheat germ agglutinin (FL-WGA).

1. Xanthenes

One preferred class of fluorescent labels comprise xanthene chromophores having a structure of general Formula VIII or IX.

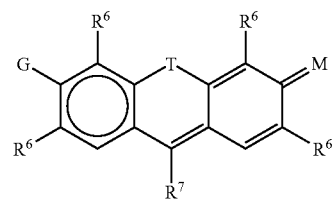

Formula VIII

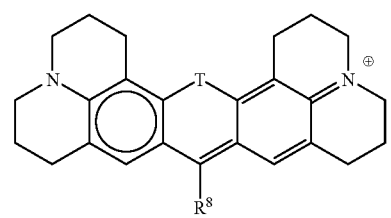

Formula IX wherein:

$R^6$ is independently selected from the group consisting of H, halogen, lower alkyl, $SO_3H$ and an alkylene attachment point;

$R^7$ is selected from the group consisting of H, lower alkyl, an alkylene attachment point, and $R^8$, wherein $R^8$ is selected from the group consisting of

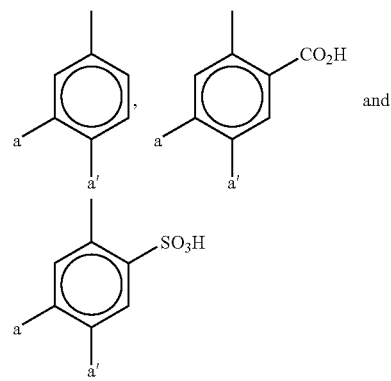

wherein:

each a and a' is independently selected from the group consisting of H and an alkylene attachment point;

G is selected from the group consisting of H, OH, $OR^9$, $NR^9R^9$ and an alkylene attachment point;

T is selected from the group consisting of O, S, $C(CH_3)_2$ and $NR^9$; and

M is selected from the group consisting of O and $NR^9R^9$;

wherein each $R^9$, which may be the same or different, is independently H or hydrocarbyl.

2. Cyanines

Another preferred class of fluorescent labels are cyanine dyes having a structure of general Formula X.

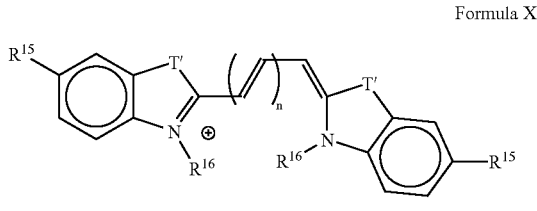

Formula X wherein:

$R^{15}$ is independently selected from the group consisting of H, halogen, lower alkyl, $SO_3H$, $PO_3H_2$, $OPO_3H_2$, COOH, and an alkylene attachment point;

$R^{16}$ is selected from the group consisting of H, lower alkyl, $(CH_2)_j COOH$, $(CH_2)_j SO_3H$, and an alkylene attachment point; where j is an integer from 1 to 10;

T' is selected from the group consisting of O, S, $C(CH_3)_2$, —CH=CH—, and $NR^{17}$, where $R^{17}$ is H or hydrocarbyl; and n is an integer from 1 to 6.

B. Fluorescent Lipids

Fluorescently labeled amphipathic lipids, in particular phospholipids, have also been successfully employed. For purposes of the present invention, an amphipathic lipid may be defined as a molecule with both hydrophobic and hydrophilic groups that bind to but do not readily cross the cell membrane. Fluorescently labelled phospholipids are of particular value as second reagent.

As defined herein, "phospholipids" include phosphatidic acid (PA), and phosphatidyl glycerols (PG), phosphatidylcholines (PC), phosphatidylethanolamines (PE), phospatidylinositols (PI), phosphatidylserines (PS), and phosphatidyl-choline, serine, inositol, ethanolamine lipid derivatives such as egg phosphatidylcholine (EPC), dilauroylphosphatidylethanolamine, dimyristoylphosphatidylethanolamine, dipalmitoyl-phosphatidylethanolamine, distearoylphosphatidylethanolamine, dioleoyl-phosphatidylethanolamine, distearoyl-phosphatidylserine, dilinoleoyl phosphatidylinositol, and mixtures thereof. They may be unsaturated lipids and may be naturally occurring or synthetic. The individual phosphatidic acid components may be symmtrical, i.e. both acyl residues are the same, or they may be unsymmetrical, i.e., the acyl residues may be different.

Fluorescent and luminescent lipids constitute an important class of molecules that function as immobile second reagents. They can serve as FRET donors, FRET acceptors, fluorescence quenchers and fluorophores that can be quenched by voltage-sensitive first reagents. Well characterized embodiments include their use as FRET donors to voltage-sensitive oxonols. Specific examples include coumarin labeled phospholipids, such as structures A (CC1-DMPE) and B (CC2-DMPE). A generic structure is shown in structure C. Other examples of fluorescent phospholipid that function as second reagents include: fluorescein labeled phosphatidylethanolamine (PE), NBD labeled PE, and AMCA-S labeled PE. Coumarin labeled single chain lipids that contain a permanent positive charge, including structure D1, have also been shown to be useful. The positively charged lipid may have electrostatic advantages with negatively charged second reagents. An electrostatic attraction between the two reagents may enable the probes to associate in the membrane and result in enhanced voltage-sensitive FRET. Furthermore, these probes have been found to allow longer recording of optical FRET signals in leech ganglia. A generic structure of fluorescently labeled quartenary ammonium lipid is shown in structure D2. The use of fluorescent lipids as FRET acceptors has also been demonstrated, for example using an oxonol donor and a Cy5-labeled PE acceptor.

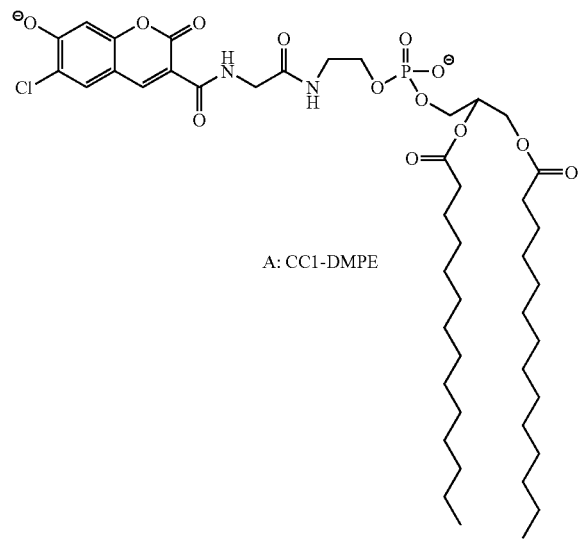

A: CC1-DMPE

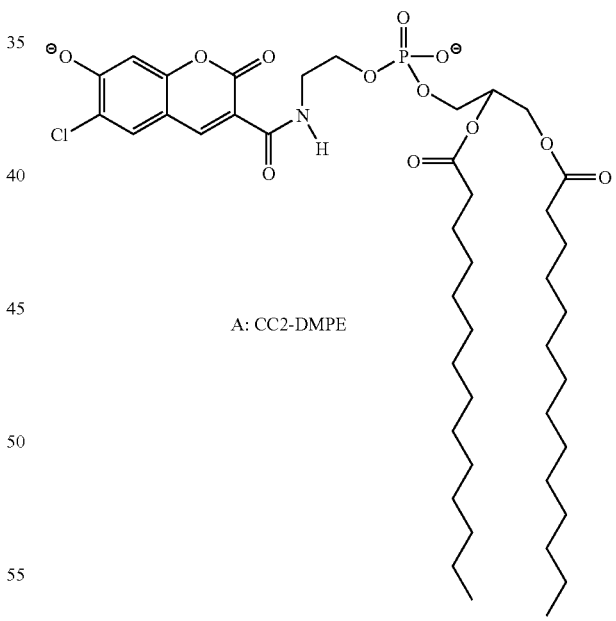

A: CC2-DMPE

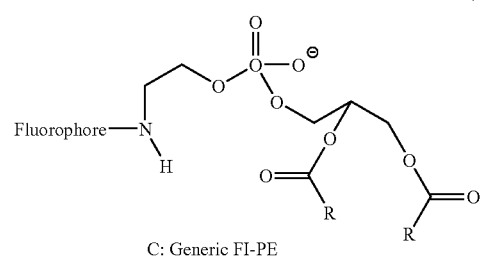

C: Generic Fl-PE

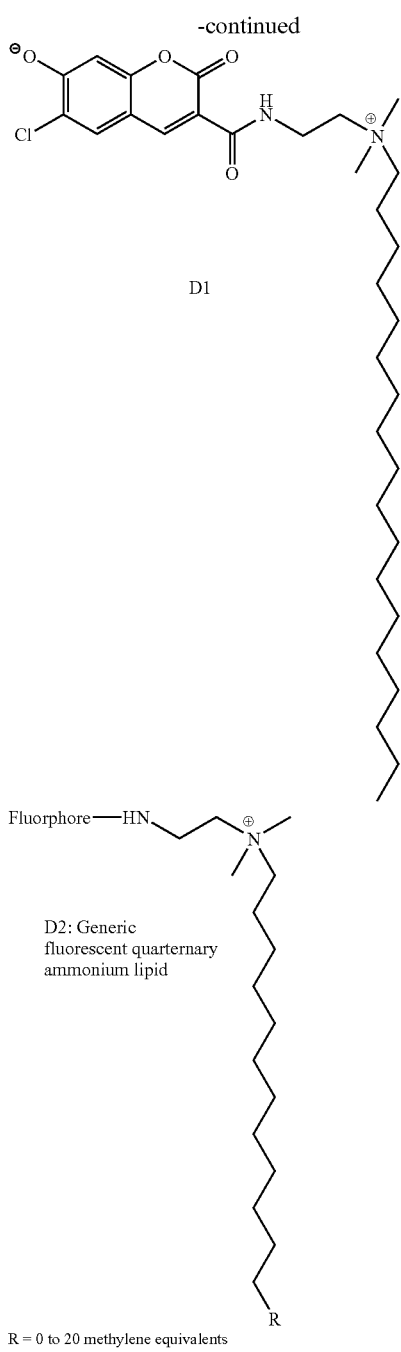

D1

D2: Generic fluorescent quarternary ammonium lipid

R = 0 to 20 methylene equivalents

The preferred lipid based second reagents comprise 1) a hydrophobic lipid anchor, 2) a charged, polar, or zwitterionic headgroup, and 3) a fluorescent component that is anchored to the membrane surface.

The hydrophobic lipid anchor should be sufficiently long to result in strong binding to the membrane (preferably 14–35 carbon or methylene units in length). Alternatively it can be composed of several proportionately (equivalent) smaller segments (i.e. one $C_{20}$ chain or two $C_{10}$ chains). This is desirable to minimize leakage of dye from the membrane location, which could effect the voltage-sensitivity and increase fluorescence background.

The headgroup should preferably comprise a permanently charged, polar, or zwitterionic group within the normal physiological pH range (pH 6.5 to 7.5) so that the molecule does not significantly translocate to the inner membrane leaflet on the timescale of about an hour. The charged headgroup prevents the fluorophore and whole molecule from diffusing across the low dielectric interior of the membrane. Significant membrane translocation will increase background fluorescence and decrease voltage-sensitivity due to the loss of asymmetry across the membrane. Preferred are charged and polar headgroups including phosphate, sulfates, quatennary ammonium groups, sugars and amines.

The fluorophore should be attached to the lipid headgroup and be located at the membrane-water interface region to maximize the distance changes between donor and acceptor when the mobile reagent I is on the intracellular leaflet. The fluorophore is preferably water-soluble. Preferred fluorophores include coumarins, fluoresceins, bodipys, carbocyanines, indocarbocyanines and styryl dyes.

One skilled in the art could meet these criteria in a variety of ways. First as has been demonstrated in the case of PE, one could use a lipid scaffold that contains the appropriate membrane anchoring hydrophobicity and charged headgroup, and then chemically attach various fluorescent groups to the headgroup. The phosphate group provides the permanent charge that inhibits membrane translocation. Since PE has a reactive amino group at the end of the headgroup, one could react any amino reactive fluorescent labeling reagent (e.g. any of those described in the Molecular Probes catalog) with PE to produce appropriate second reagents. Amino reactive reagents could also be prepared from chromophores not listed in the Molecular Probes catalog using standard synthetic chemical protocols. Similarly, one could execute the same procedure on any amino lipid as long at the headgroup contains a permanent charge at physiological pH. For example, the quaternary ammonium lipid in structure D could be prepared in such a manner to contain a terminal amino group that could then be reacted with the aforementioned amino reactive groups. A second approach to prepare appropriate lipids would be to synthesize a fluorescent charged headgroup that could then be reacted with a variety of hydrophobic anchors. The three components: fluorophore, headgroup, and lipid anchor can be assembled in any order to produce the same final product. In addition to amine reactive fluorescent labeling agents, reagents for fluorescently labeling thiol, alcohol, aldehyde, ketone, caboxylic acid functional groups are readily available and could be reacted with a lipid scaffold that meets the charge and membrane anchor criteria and also have these functional groups. Of course fluorophore modifications that maintain fluorescence of the chromophore would also produce molecules that can function as second reagents. The appropriate chromophore modification are known to those skilled in the art and have been described in part in for example in U.S. Pat. No. 5,741,657 issued Apr. 21, 1998 to Tsien et al.

Long-lived (>100 ns) light-emitting lipids can also function as the stationary second reagent. One example class includes lipids with a charged headgroup capable of chelating metal ions and undergoing photo-induced long-lived emission. These molecules may be enhanced with an organic sensitizer covalently attached. Example of metal ions that may be appropriate include: $Eu^{3+}$, $Tb^{3+}$, $Sm^{3+}$, $Dy^{3+}$, $Ru^{2+/3+}$, and $Rh^{2+}$.

Synthesis of Compound D1.

Synthesis of Coumarin Amine [N-(2-(dimethylamino)ethyl)(6-chloro-2-oxo-7-((phenylmethoxy)methoxy)(2H-chromen-3-yl))formamide]

241 mg 3-carboxy-6-chloro-7-hydroxy coumarin (1 mmol) dissolved in the mixture of 5 ml THF and 5 ml DMF was added 200 ul diisopropylethylamine (DIEA, 1.1 mmol) and 330 mg O-(N-succinium)-N,N,N',N'-tetramethyl uronium tetrafluoroborate (TSTU, 1.1 mmol). After stirring at room temperature for 20 minutes under nitrogen atmosphere, the reaction mixture was added 400 ul of DIEA and 460 ul benzyl chloromethyl ether (BOM-Cl) and stirred for another 2 hours at room temperature. The resulted mixture was then pulled high vacuum for 2 hours and 1 ml THF, 480 ul 2-dimethylaminoethylamine was added into the solution afterwards. After the reaction mixture was allowed to react at room temperature for 1 hour, the crude product was pulled high vacuum again overnight and purified on a silica gel column (chloroform: methanol=95:5 as eluent). 190 mg colorless solid was obtained as product, 44% yield. $^1$H NMR (CDCl$_3$, ppm): 2.32 (d, 6H), 2.56 (t, 2H), 2.16 (t, 2H), 4.76 (s, 2H), 5.46 (s, 2H), 7.33 (m, 7H), 7.68 (s, 1H), 8.76 (s, 1H). MS: $C_{22}H_{23}O_5N_2Cl$, 430.3 calculated; 431.2 (M+1) found.

Synthesis of C18-coumarin [N3-(2-(1,1-dimethyl-1-octadecylammonio)-6-chloro-7-hydroxy-2-oxo-2H-3-chromene-carboxamide]

43 mg coumarin amine (0.1 mmol) from last step synthesis dissolved in dichloromethane and 43 mg 1-iodooctadecane was added into the solution. After the reaction mixture was heated with stirring at 80° C. for 24 hours under nitrogen atmosphere, solvent was evaporated and the crude product was purified on a silica gel column (chloroform: methnol=8:2 as eluent). 30 mg yellow color solid was obtained as product, 53% yield. $^1$H NMR (CD$_3$OD, ppm): 0.90 (t, 3H), 1.28 (m, 35H), 3.17 (s, 6H), 3.56 (t, 2H), 3.90 (t, 2H), 6.73 (s, 1H), 7.78 (s, 1H), 8.69 (s, 1H). MS: $C_{32}H_{52}N_2O_4ClI$, 691.4 calculated; 563.5 (M–I$^-$) found.

C. Fluorescently Labelled Antibodies

Antibodies directed against surface antigens such as glycolipids or membrane proteins can also be fluorescently labeled and used as second reagents. For example, FTC-labeled antibodies against the glycolipid GD3 stain the outer surface of the melanoma cell line M21 and give ratio changes up to 10%/100 mV using DiSBA-C$_6$-(3) as the mobile fluorescent anion. Specificity for particular cell types is likely to be easier to achieve with antibodies than with lectins because antibodies can be raised against nearly any surface marker. Also, microinjected antibodies could label sites on the cytoplasmic face of the plasma membrane, where carbohydrate binding sites for lectins are absent.

D. Cytochromes

Cytochrome c used as a second reagent has also been found to function as a quencher that binds to the outer plasma membrane surface. Accordingly, another suitable class of second reagent comprises cytochrome c or apocytochrome c, with or without a fluorescent group as previously described in connection with other second reagents.

E. Fluorescent Carbohydrates

Yet another preferred class of embodiments of the second reagent includes fluorescently labeled, amphipathic carbohydrates, e.g., cyclodextrins that selectively and tightly bind to the extracellular plasma membrane surface. Typically, the carbohydrates are functionalized with a hydrophobic tail to facilitate intercalation into the membrane and tight membrane binding. The cyclic sugar imparts good water solubility for cellular loading and prohibits membrane translocation. Another added benefit is that the cyclodextrins aid the loading of the oxonol.

F. Fluorescent Peptides and Proteins

Yet another preferred class of embodiments of the second reagent includes fluorescently labeled, amphipathic peptides. Typically such peptides contain several basic residues such as lysines and arginines to bind electrostatically to negatively charged phospholipid head groups, plus several hydrophobic residues to anchor the peptide to the membrane. Optionally, long-chain alkyl substituents such as N-myristoyl, N-palmitoyl, S-palmitoyl, or C-terminal prenyl groups may provide hydrophobicity. The fluorescent label is typically attached via lysine epsilon-amino groups or cysteine sulfhydryl groups.

G. Naturally Fluorescent Proteins

Another preferred class of embodiments of the second reagent includes naturally fluorescent proteins such as the Green Fluorescent Protein (GFP) of *Aequorea Victoria* (Cubitt, A. B. et al. 1995. Understanding, improving, and using green fluorescent proteins. *Trends Biochem. Sci.* 20: 448–455; Chalfie, M., and Prasher, D. C. U.S. Pat. No. 5,491,084). Because the entire fluorophore and peptide of a naturally fluorescent protein can be expressed within intact living cells without the addition of other co-factors or fluorophores, voltage sensors comprising such proteins as the second reagent provide the ability to monitor membrane potential changes within defined cell populations, tissues or in an entire transgenic organism, where other reagents could not penetrate or be specifically localized. For example, by the use of cell type specific promoters and subcellular targeting motifs, it is possible to selectively target the second reagent to a discrete location to enable highly spatially defined measurements.

Endogenously fluorescent proteins have been isolated and cloned from a number of marine species including the sea pansies *Renilla reniformis, R. kollikeri* and *R. mullerei* and from the sea pens *Ptilosarcus, Stylatula* and *Acanthoptilum*, as well as from the Pacific Northwest jellyfish, *Aequorea victoria*; Szent-Gyorgyi et al. (SPIE conference 1999), D. C. Prasher et al., Gene, 111:229–233 (1992) and several species of coral (Matz et al. Nature Biotechnology 17 969–973 (1999). These proteins are capable of forming a highly fluorescent, intrinsic chromophore through the cyclization and oxidation of internal amino acids within the protein that can be spectrally resolved from weakly fluorescent amino acids such as tryptophan and tyrosine.

Additionally fluorescent proteins have also been observed in other organisms, although in most cases these require the addition of some exogenous factor to enable fluorescence development. For example, the cloning and expression of yellow fluorescent protein from *Vibrio fischeri* strain Y-1 has been described by T. O. Baldwin et al., Biochemistry (1990) 29:5509–15. This protein requires flavins as fluorescent co-factors. The cloning of Peridinin-chlorophyll a binding protein from the dinoflagellate *Symbiodinium* sp. was described by B. J. Morris et al., Plant Molecular Biology, (1994) 24:673:77. One useful aspect of this protein is that it fluoresces in red. The cloning of phycobiliproteins from marine cyanobacteria such as *Synechococcus*, e.g., phycoerythrin and phycocyanin, is described in S. M. Wilbanks et al., J. Biol. Chem. (1993) 268:1226–35. These proteins require phycobilins as fluorescent co-factors, whose insertion into the proteins involves auxiliary enzymes. The proteins fluoresce at yellow to red wavelengths.

A variety of mutants of the GFP from *Aequorea victoria* have been created that have distinct spectral properties, improved brightness and enhanced expression and folding in mammalian cells compared to the native GFP, SEQ. ID. NO: 1 Table 1, (*Green Fluorescent Proteins*, Chapter 2, pages 19 to 47, edited Sullivan and Kay, Academic Press, U.S. Pat. No. 5,625,048 to Tsien et al., issued Apr. 29, 1997; U.S. Pat. No. 5,777,079 to Tsien et al., issued Jul. 7, 1998; and U.S. Pat. No. 5,804,387 to Cormack et al., issued Sep. 8, 1998). In many cases these functional engineered fluorescent proteins have superior spectral properties to wild-type *Aequorea* GFP and are preferred for use as second reagents in the present invention.

TABLE 1

Aequorea Fluorescent Proteins

| Mutations | Common Name | Quantum Yield ($\Phi$) & Molar Extinction | Excitation & Emission Max | Relative Fluorescence At 37° C. | Sensitivity To Low pH % max F at pH 6 |
|---|---|---|---|---|---|
| *S65T type* | | | | | |
| S65T, S72A, N149K, M153T, I167T | Emerald | $\Phi = 0.68$<br>$\epsilon = 57,500$ | 487<br>509 | 100 | 91 |
| F64L, S65T, V163A | | $\Phi = 0.58$<br>$\epsilon = 42,000$ | 488<br>511 | 54 | 43 |
| F64L, S65T | EGFP | $\Phi = 0.60$<br>$\epsilon = 55,900$ | 488<br>507 | 20 | 57 |
| S65T | | $\Phi = 0.64$<br>$\epsilon = 52,000$ | 489<br>511 | 12 | 56 |
| *Y66H type* | | | | | |
| F64L, Y66H, Y145F, V163A | P4-3E | $\Phi = 0.27$<br>$\epsilon = 22,000$ | 384<br>448 | 100 | N.D. |
| F64L, Y66H, Y145F | | $\Phi = 0.26$<br>$\epsilon = 26,300$ | 383<br>447 | 82 | 57 |
| Y66H, Y145F | P4-3 | $\Phi = 0.3$<br>$\epsilon = 22,300$ | 382<br>446 | 51 | 64 |
| Y66H | BFP | $\Phi = 0.24$<br>$\epsilon = 21,000$ | 384<br>448 | 15 | 59 |
| *Y66W type* | | | | | |
| S65A, Y66W, S72A, N146I, M153T, V163A | W1C | $\Phi = 0.39$<br>$\epsilon = 21,200$ | 435<br>495 | 100 | 82 |
| F64L, S65T, Y66W, N146I, M153T, V163A | W1B | $\Phi = 0.4$<br>$\epsilon = 32,500$ | 434 452<br>476 (505) | 80 | 71 |
| Y66W, N146I, M153T, V163A | hW7 | $\Phi = 0.42$<br>$\epsilon = 23,900$ | 434 452<br>476 (505) | 61 | 88 |
| Y66W | | | 436<br>485 | N.D. | N.D. |
| *T203Y type* | | | | | |
| S65G, S72A, K79R, T203Y | Topaz | $\Phi = 0.60$<br>$\epsilon = 94,500$ | 514<br>527 | 100 | 14 |
| S65G, V68L, S72A, T203Y | 10C | $\Phi = 0.61$<br>$\epsilon = 83,400$ | 514<br>527 | 58 | 21 |
| S65G, V68L, Q69K, S72A, T203Y | h10C+ | $\Phi = 0.71$<br>$\epsilon = 62,000$ | 516<br>529 | 50 | 54 |
| S65G, S72A, T203H | | $\Phi = 0.78$<br>$\epsilon = 48,500$ | 508<br>518 | 12 | 30 |
| S65G, S72A T203F | | $\Phi = 0.70$<br>$\epsilon = 65,500$ | 512<br>522 | 6 | 28 |
| *T203I type* | | | | | |
| T203I, S72A, Y145F | Sapphire | $\Phi = 0.64$<br>$\epsilon = 29,000$ | 395<br>511 | 100 | 90 |
| T203I T202F | H9 | $\Phi = 0.6$<br>$\epsilon = 20,000$ | 395<br>511 | 13 | 80 |

Non Aequorea fluorescent proteins, for example Anthozoan fluorescent proteins, and functional engineered mutants thereof, are also suitable for use in the present invention including those shown in Table 2 below.

TABLE 2

Anthozoa Fluorescent Proteins

| Species | Protein Name | Quantum Yield ($\Phi$) & Molar Extinction | Excitation & Emission Max | Relative Brightness | SEQ. ID. NO: |
|---|---|---|---|---|---|
| Anemonia majano | amFP486 | $\Phi$ = 0.24<br>$\epsilon$ = 40,000 | 458<br>486 | 0.43 | SEQ. ID. NO: 2 |
| Zoanthus sp | zFP506 | $\Phi$ = 0.63<br>$\epsilon$ = 35,600 | 496, 506 | 1.02 | SEQ. ID. NO: 3 |
|  | zFP538 | $\Phi$ = 0.42<br>$\epsilon$ = 20,200 | 528, 538 | 0.38 | SEQ. ID. NO: 4 |
| Discosoma striata | dsFP483 | $\Phi$ = 0.46<br>$\epsilon$ = 23,900 | 443<br>483 | 0.5 | SEQ. ID. NO: 5 |
| Discosoma sp "red" | drFP583 | $\Phi$ = 0.23<br>$\epsilon$ = 22,500 | 558<br>583 | 0.24 | SEQ. ID. NO: 6 |
| Clavularia sp | CFP484 | $\Phi$ = 0.48<br>$\epsilon$ = 35,300 | 456<br>484 | 0.77 | SEQ. ID. NO: 7 |

H. Bioluminescent Proteins

Preferred luminescent components include chemi-luminescent, electro-luminescent and bioluminescent compounds. Preferred bioluminescent components include bioluminescent proteins such as firefly, bacterial or click beetle luciferases, aequorins and other photoproteins, for example as described in U.S. Pat. No. 5,221,623, issued Jun. 22, 1989 to Thompson et al., and U.S. Pat. No. 5,683,888 issued Nov. 4, 1997 to Campbell, U.S. Pat. No. 5,674,713 issued Sep. 7 1997 to DeLuca et al., U.S. Pat. No. 5,650,289 issued Jul. 22, 1997 to Wood and U.S. Pat. No. 5,843,746 issued Dec. 1, 1998 to Tatsumi et al.

Particularly preferred are bioluminescent proteins isolated from the ostracod *Cypridina* (or *Vargula*) *hilgendorfii*. (Johnson and Shimomura, (1978) Methods Enzymol 57 331–364, Thompson, Nagata & Tsuji (1989) Proc. Natl. Acad. Sci. USA 86, 6567–6571).

Beyond the availability of bioluminescent proteins (luciferases) isolated directly from the light organs of beetles, cDNAS encoding luciferases of several beetle species (including, among others, the luciferase of *P. pyralis* (firefly), the four luciferase isozymes of *P. plagiophthalamus* (click beetle), the luciferase of *L. cruciata* (firefly) and the luciferase of *L. lateralis*) (deWet et al., Molec. Cell. Biol. 7, 725–737 (1987); Masuda et al., Gene 77, 265–270 (1989); Wood et al., Science 244, 700–702 (1989); European Patent Application Publication No. 0 353 464) are available. Further, the cDNAs encoding luciferases of any other beetle species, which make bioluminescent proteins, are readily obtainable by the skilled using known techniques (de Wet et al. Meth. Enzymol. 133, 3–14 (1986); Wood et al., Science 244, 700–702 (1989).

Bioluminescent light-emitting systems have been known and isolated from many luminescent organisms, including certain bacteria, protozoa, coelenterates, molluscs, fish, millipedes, flies, fungi, worms, crustaceans, and beetles, particularly the fireflies of the genera *Photinus, Photuris,* and *Luciola* and click beetles of genus *Pyrophorus*.

In many of these organisms, enzymatically catalyzed oxido-reductions take place in which the free energy change is utilized to excite a molecule to a high energy state. Then, when the excited molecule spontaneously returns to the ground state, visible light is emitted. This emitted light is called "bioluminescence." Typically one quantum of light is emitted for each molecule of substrate oxidized (which is generically referred to as a luciferin). The electronically excited state of the oxidized substrate is a state that is characteristic of the luciferase-luciferin reaction of a bioluminescent protein; the color (and, therefore, the energy) of the light emitted upon return of the oxidized substrate to the ground state is determined by the enzyme (or luciferase).

Most firefly and click beetle luciferases are ATP and magnesium dependent and require oxygen for light production. Typically light emission from these enzymes exhibits a rapid burst in intensity followed by a rapid decrease in the first few seconds, followed by a significantly slower sustained light emission. Relatively sustained light output at high rates has been accomplished in these systems by inclusion of coenzyme A, dithiothreitol and other reducing agents that reduce product inhibition and slows inactivation of the luciferase that occurs during catalysis of the light producing reaction, as described in U.S. Pat. No. 5,641,641, issued Jun. 24, 1997, and U.S. Pat. No. 5,650,289, issued Jul. 22, 1997. Such stable light emitting systems are preferred for use in the present system.

Particularly preferred bioluminescent proteins are those derived from the ostracod *Cypridina* (or *Vargula*) *hilgendorfii*. The *Cypridina* luciferase (GenBank accession no. U89490) uses no cofactors other than water and oxygen, and its luminescent reaction proceeds optimally at pH 7.2 and physiological salt concentrations, (Shimomura, O., Johnson, F. H. and Saiga, Y. (1961) J. Cell. Comp. Physiol. 58 113–124). By comparison, firefly luciferase has optimal activity at low ionic strength, alkaline pH and reducing conditions, that are typically quite different to those usually found within mammalian cells. Because *Cypridina* luciferase has a turnover number of 1600 min$^{-1}$ and a quantum yield of 0.29, (Shimomura, O. & Johnson, F. H. and Masugi, T. (1969) Science 164 1299–1300; Shimomura, O. & Johnson, F. H. (1970) Photochem. Photobiol. 12 291–295), the *Cypridina* luciferase produces a specific photon flux exceeding that of the optimized firefly system by a factor of at least 50 (Miesenbock and Rothman, Proc. Natl. Acad. Sci. USA (1997) 94 3402–3407.

The ready availability of cDNAs encoding various bioluminescent proteins makes possible their use in the voltage assays of the present invention. By coupling energy transfer from the bioluminescent protein to the acceptor fluorophore which is mobile within a biological membrane the bioluminescent proteins can provide highly specific and sensitive voltage measurements.

III. Targeting to Biological Membranes

Typically the fluorescent and bioluminescent components additionally comprise a localization or targeting sequence to direct or sort the component to a particular face of a biological membrane or subcellular organelle. Preferred localization sequences provide for highly specific localization of the protein, with minimal accumulation in other biological membranes. Example localization sequences that direct proteins to specific subcellular structures are shown below in Table 3.

such as SH2, SH3, PDZ, 14,3,3 and PTB domains, protein-DNA domains such as zinc finger motifs, and protein-lipid interaction domains such as PH, $Ca^{2+}$/lipid binding domains. Other interaction domains are described in for example, the database of interacting proteins available on the web at http://www.doe-mbi.ucla.edu. An advantage of this approach is that extremely specific patterns of localization can be achieved that correspond in vivo to the functional compartmentation of proteins within a cell. Such functional compartmentation of proteins can play significant roles in specialized cell types such as neurons that have unique cellular architectures.

TABLE 3

Protein Localization Sequences

| Location | Sequence | SEQ. ID. NO. | Preferred Orientation |
|---|---|---|---|
| Nuclear (Import) | PPKKKRKV | SEQ. ID. NO. 8 | N-terminal |
| Endoplasmic reticulum (Import) | MSFVSLLLVGILFWATGAENLTK CEVFN | SEQ. ID. NO. 9 | N-terminal |
| Endoplasmic reticulum (Retention) | KDEL | SEQ. ID. NO. 10 | C-terminal, |
| | KKAA | SEQ. ID. NO. 11 | |
| Peroxisome (Import) | SKL | SEQ. ID. NO. 12 | C-terminal |
| Mitochondrial (Inner membrane) | MLSLRNSIRFFKPATRTLCSSRYLL | SEQ. ID. NO. 13 | N-terminal |
| Mitochondrial (Outer membrane) | MLRTSSLFTRRVQPSLFRNILRLQ ST | SEQ. ID. NO: 14 | N-terminal |
| Plasma membrane (Cytosolic face) | MGCIKSKRKDNLNDDGVDMKT | SEQ. ID. NO: 15 | N-terminal |
| Plasma membrane (Cytosolic face) | KKKKKKKSKTKCVIM | SEQ. ID. NO: 16 | C-terminal |

Other examples of localization signals are described in for example, in "Protein Targeting", chapter 35 of Stryer, L., *Biochemistry* (4th ed.). W. H. Freeman, 1995 and Chapter 12 (pages 551–598) of Molecular Biology of the Cell, Alberts et al. third edition, (1994) Garland Publishing Inc. In some cases, correct localization requires a number of discrete localization motifs to provide for correct sorting by the cellular machinery. For example, correct sorting of proteins to the extracellular face of the plasma membrane requires an N-terminal signal sequence and a C-terminal GPI anchor or transmembrane domain.

Localization sequences in general can be located almost anywhere in the amino acid sequence of the protein. In some cases the localization sequence can be split into two blocks separated from each other by a variable number of amino acids. The creation of such constructs via standard recombinant DNA approaches is well known in the art, as for example described in Maniatis, et al., *Molecular Cloning A Laboratory Manual*, Cold Spring Harbor Laboratory, N.Y, 1989).

Localization of the second reagent can also be achieved by fusion to a protein with a defined pattern of spatial distribution in a given cell type. In this case, the specific localization sequences need not be defined. Because such fusions to fluorescent or bioluminescent proteins can be directly visualized by microscopy it is possible to routinely test previously unknown sequences and determine their utility in the assay.

Another class of localization sequences includes targetable sequences that enable conditional binding via an interaction domain to a specific location in the cell. Examples of include protein-protein interaction domains The approach is generally applicable to any interaction domain. The creation of such constructs via standard recombinant DNA approaches is well known in the art, as for example described in Maniatis, et al., *Molecular Cloning A Laboratory Manual*, Cold Spring Harbor Laboratory, N.Y, 1989).

The addition of the domain to the naturally fluorescent or luminescent protein provides for the potential regulation of binding to the subcellular site in response to a defined activation signal. In certain circumstances this can be used to enhance the sensitivity and or specificity of the fluorescence changes if cellular activation also regulates membrane potential. For example, creation of a fusion protein comprising the bioluminescent or fluorescent protein to a receptor or ion channel directly coupled to the voltage change could augment the fluorescence response if stimulation of the cell also resulted in a change in the cellular location of the fusion protein.

IV Transfection and Expression of Reagents

Nucleic acids used to transfect cells with sequences coding for expression of the polypeptide of interest generally will typically be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the fluorescent or bioluminescent protein coding sequence, operatively coupled to appropriate localization or targeting domains and appropriate transcriptional I translational control signals. These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y, 1989). Many commercially available expression vectors are available from a variety of sources including Clontech (Palo Alto, Calif.), Stratagene (San Diego, Calif.) and Invitrogen (San Diego, Calif.) as well as and many other commercial sources.

A contemplated version of the method is to use inducible controlling nucleotide sequences to produce a sudden increase in the expression of bioluminescent or fluorescent protein e.g., by inducing expression of the construct. Example inducible systems include the tetracycline inducible system first described by Bujard and colleagues (Gossen and Bujard (1992) Proc. Natl. Acad. Sci USA 89 5547–5551, Gossen et al. (1995) Science 268 1766–1769) and described in U.S. Pat. No 5,464,758.

Transformation of a host cell with recombinant DNA may be carried out by conventional techniques as are well known to those skilled in the art. Where the host is prokaryotic, such as *E. coli*, competent cells that are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein.

V. Transgenic Organisms

In another embodiment, the invention provides a transgenic non-human organism that expresses a nucleic acid sequence that encodes a bioluminescent or fluorescent protein. Because bio-luminescent and naturally fluorescent proteins can be specifically expressed within intact living cells, voltage sensors comprising such proteins as the second reagent provide the ability to monitor membrane potential changes within defined cell populations, tissues or in an entire transgenic organism.

Such non-human organisms include vertebrates such as rodents, fish such as Zebrafish, non-human primates and reptiles as well as invertebrates such as insects, *C. elegans* etc. Preferred non-human organisms are selected from the rodent family including rat and mouse, most preferably mouse. The transgenic non-human organisms of the invention are produced by introducing transgenes into the germline of the non-human organism. Embryonic target cells at various developmental stages can be used to introduce transgenes. Different methods are used depending on the organism and stage of development of the embryonic target cell. In vertebrates, the zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

A transgenic organism can be produced by cross-breeding two chimeric organisms which include exogenous genetic material within cells used in reproduction. Twenty-five percent of the resulting offspring will be transgenic i.e., organisms that include the exogenous genetic material within all of their cells in both alleles. 50% of the resulting organisms will include the exogenous genetic material within one allele and 25% will include no exogenous genetic material.

Retroviral infection can also be used to introduce transgene into a non-human organism. In vertebrates, the developing non-human embryo can be cultured in vitro to the blastocyst stage. During this time, the blastomeres can be targets for retro viral infection (Jaenich, R., *Proc. Natl. Acad. Sci USA* 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 82:6927–6931, 1985; Van der Putten, et al., *Proc. Natl. Acad. Sci USA* 82:6148–6152, 1985). Transfection is easily and efficiently obtained by culturing the blastomeres on a monolayer of virus-producing cells (Van der Putten, supra; Stewart, et al., *EMBO J.* 6:383–388, 1987).

Alternatively, infection can be performed at a later stage. Virus or virus-producing cells can be injected into the blastocoele (D. Jahner et al., *Nature* 298:623–628, 1982). Most of the founders will be mosaic for the transgene since incorporation occurs only in a subset of the cells that formed the transgenic nonhuman animal. Further, the founder may contain various retro viral insertions of the transgene at different positions in the genome that generally will segregate in the offspring. In addition, it is also possible to introduce transgenes into the germ line, albeit with low efficiency, by intrauterine retro viral infection of the midgestation embryo (D. Jahner et al., supra).

A third type of target cell for transgene introduction for vertebrates is the embryonic stem cell (ES). ES cells are obtained from pre-implantation embryos cultured in vitro and fused with embryos (M. J. Evans et al. *Nature* 292: 154–156, 1981; M. O. Bradley et al., *Nature* 309: 255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

As the preceding discussion indicates and would be readily appreciated by those skilled in the art, a wide variety of known donor/acceptor pairs can be used as first and second reagents. Particularly preferred combinations include, but are not limited to, the following, in which the first-named fluorophore is the donor and the second is the acceptor: fluorescein/bis-thiobarbiturate trimethineoxonol; Naturally Fluorescent Protein/bis-thiobarbiturate trimethineoxonol; Naturally Fluorescent Protein/bis-thiobarbiturate pentamethineoxonol; coumarin/bis-thiobarbiturate trimethineoxonol; coumarin/bis-thiobarbiturate pentamethineoxonol; bis-thiobarbiturate trimethineoxonol/Texas Red; bis-thiobarbiturate trimethineoxonol/resorufin; bis-thiobarbiturate trimethineoxonol/Cy5; bis-thiobarbiturate trimethineoxonol/bis-thiobarbiturate pentamethineoxonol; Texas Red/bis-thiobarbiturate pentamethineoxonol; NBD/bis-thiobarbiturate trimethineoxonol; NBD/bis-thiobarbiturate pentamethineoxonol; Luciferase/Naturally fluorescent protein.

VI. Linker Groups Between First and Second Reagent

In some particularly preferred embodiments of the compositions and methods of the present invention, a linker group is employed between the first and second fluorophores. The linker group maintains a certain minimum proximity between the first and second fluorophores and ensures efficient energy transfer between the donor and acceptor (or fluorophore and quencher) when they are on the same side of the membrane, even at low concentrations. The good energy transfer allows one to separate the donor emission further from the acceptor absorbance and thus decrease the spectral crosstalk that contributes to the reduction of the voltage-sensitive ratio change from theoretical values. Another major advantage of a linker is that it converts the system into a unimolecular phenomenon. This greatly simplifies the fluorescence readout, ensures 1:1 stoichiometry of donor and acceptor (or fluorophore and quencher), and eliminates the need for optimizing relative loading levels of donor and acceptor for an optimum voltage-sensitive fluorescence change (with the additional benefit of minimal cellular perturbation and toxicity). The linker group is long enough to span the entire membrane.

The hydrophobic fluorescent molecule and the second reagent are attached to each other by means of a bifunctional linker. "Linker group" shall mean the "chemical arm" between the first and second reagent. As one skilled in the art will recognize, to accomplish the requisite chemical structure, each of the reactants must contain the necessary reactive groups.

Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkyl halides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the two species to each other. The portions of the linker closest to the second reagent may be hydrophilic, whereas the portions of the linker closest to the mobile fluorescent molecule should be hydrophobic to permit insertion into the membrane and to avoid retarding the voltage-dependent translocation of the anion. The covalent linkages should be stable relative to the solution conditions under which the cells are loaded. Generally preferred linking groups will comprise 20–40 bonds from one end to the other and 0–10 heteroatoms (NH, O, S) and may be branched or straight chain. Without limiting the foregoing, it should be evident to one skilled in the art that only combinations of atoms which are chemically compatible comprise the linking group. For example, amide, ester, thioether, thioester, keto, hydroxyl, carboxyl, ether groups in combinations with carbon-carbon bonds are acceptable examples of chemically compatible linking groups. Other chemically compatible linkers may be found in U.S. Pat. No. 5,470,997 (col. 2 and col. 4–7) and U.S. Pat. No. 5,470,843 (cols. 11–13).

Figure 11:
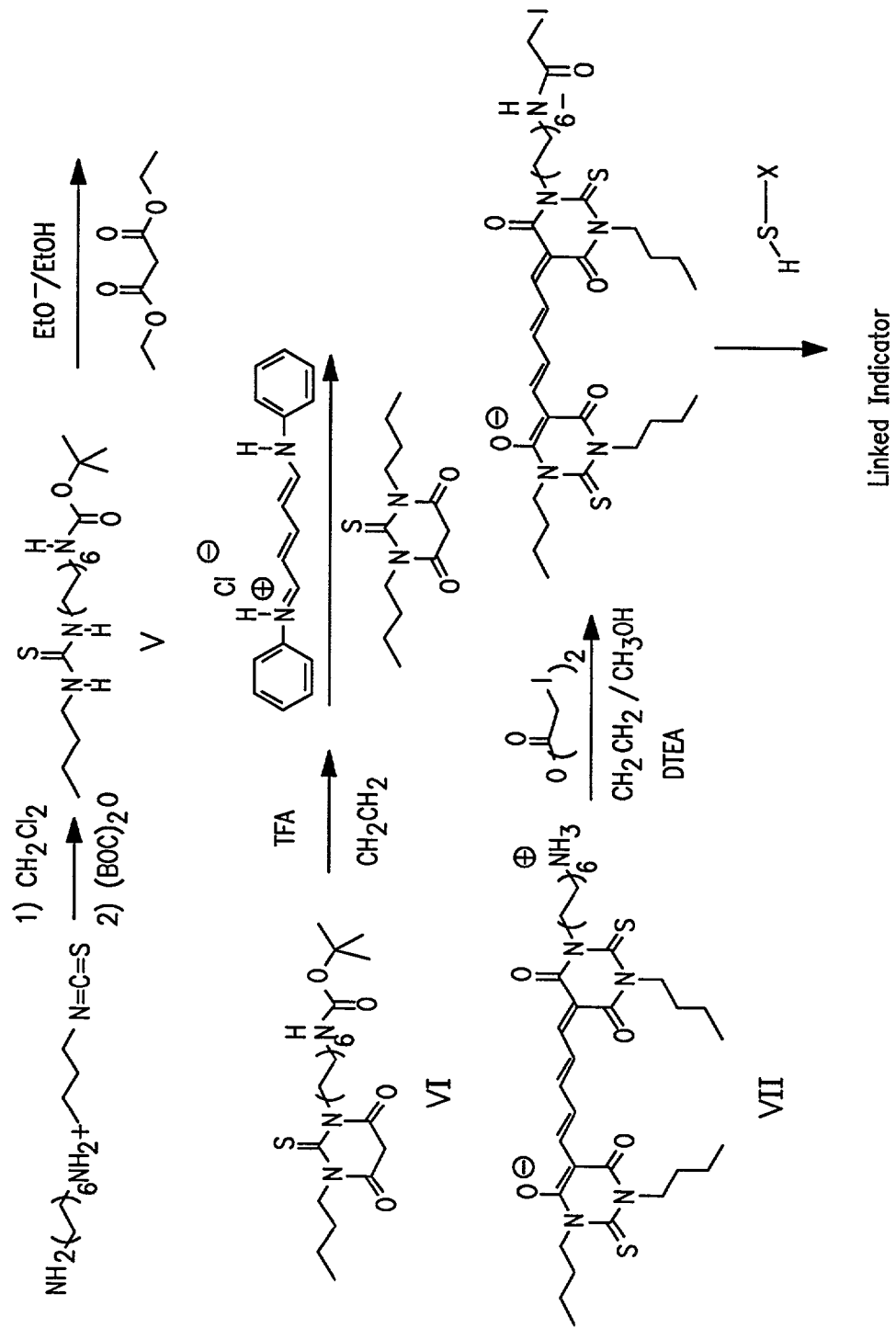
FIG. 11 shows a synthesis of an asymmetric oxonol and its linkage to a second reagent.

Asymmetric 1,3-substituted thioureas have been prepared for use in synthesizing oxonols with N-substituted linkers containing terminal reactive groups capable of conjugating to appropriate second reagent fluorophores/quenchers. In one example, one of the oxonol substituents is a pentyl chain ($C_5$) with a terminal bromide or tosylate group. Thiobarbiturates have been synthesized from these thioureas and diethylmalonate in ethoxide/ethanol. Mixed pentamethine oxonols prepared from 1 equivalent of the barbiturate with functionalized linkers and 1,3-dibutyl thiobarbiturate have been characterized. An exemplary synthesis is depicted in FIG. 11. It will be recognized that oxonols with alkyl chains of length other than $C_5$ can be readily prepared by such a method and are contemplated as within the scope of this invention.

One preferred class of suitable linkers includes bi-functionalized polyalkylene glycol oligomers (polyethyleneglycol, polypropyleneglycol, polybutyleneglycol, etc.) of an appropriate length to span the plasma membrane (25–30 carbon equivalents), for example 8–10 PEG units. The oxygen (or sulfur, in the corresponding thio-analogs thereof) modulates the hydrophobicity and hence translocation rate and loading. Compounds joined by such linker groups have the general formula

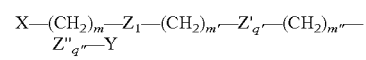

wherein:
X is a hydrophobic fluorescent anion;
Y is a fluorescent second reagent;
Z, Z', Z'' are independently O, S, SS, CO, COO;
m, m' and m'' are integers from 0 to about 32;
q, q', and q'' are independently 0 or 1; and
m+q +m'+q'+m''+q'' is from about 20 to 40 (preferably between 25 and 35).

Preferably Z is S, i.e., the linkers are polyalkylene thioethers; m=5, Z=S, q=1, m'=12, Z'=S, q'=1, m"=11, Z"=CO, and q=1.

Another class of suitable linkers includes functionalized alkyl chains with terminal thiol groups that form a central disulfide linkage. The disulfide functions as a hydrophobic swivel in the center of the membrane. These compounds have the general formula

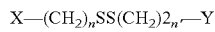

X—(CH$_2$)$_n$SS(CH$_2$)2$_{n'}$—Y wherein:

X is a hydrophobic fluorescent anion;

Y is a fluorescent second reagent;

n and n' are integers from 0 to about 32 wherein n+n' is less than or equal to 33.

Figure 12:
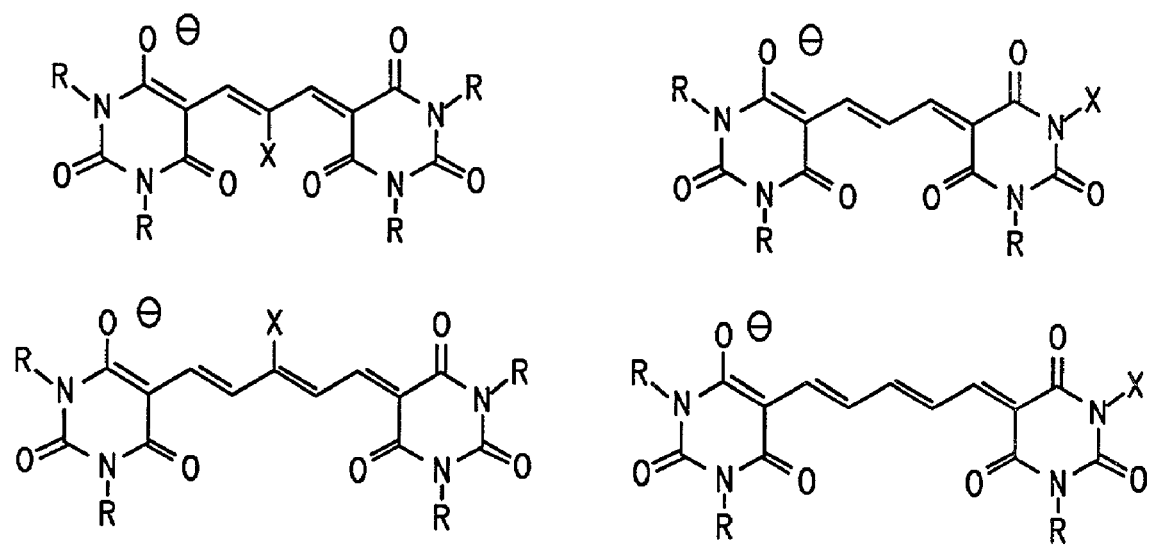
FIG. 12 shows possible linkage points (X) of oxonols to a second reagent.

As would be readily appreciated by those skilled in the art, the linker groups may be reacted with appropriately substituted or functionalized first and second fluorophores using conventional coupling chemistries. Further, it is evident that the linker group may be attached to a fluorophore at a variety of different positions. Important locations (X) for attachment of the linker in exemplary classes of oxonols are illustrated in FIG. 12.

VII. Measurement Methods

In one class of embodiments of the present invention, the hydrophobic ion fluorescence on one face of the membrane is quenched by a mechanism other than FRET.

FRET has the advantages of working over relatively long distances (compared to the thickness of a typical biological membrane), which minimizes the necessary concentration of acceptors to give a ratiometric output at two emission wavelengths. However, if FRET is too efficient over distances greater than the thickness of the membrane, it can fail to provide good discrimination between acceptors on the same vs. opposite sides of the membrane.

The second fluorophore/quencher or luminescent component can be located on either the intracellular or the extracellular face, as long as it is specific to one or the other. In the specific examples reported herein, the extracellular surface was targeted for convenience.

FRET or fluorescence quenching is can be detected by emission ratioing that can distinguish the two populations of the mobile fluorophore, i.e., those bound to the extracellular vs. those bound to the intracellular face of the membrane. In particular, FRET using a fluorescent acceptor and a fluorescent donor provides an emission ratio change that is well suited to laser scanning confocal microscopy and internally corrects for variations in donor loading, cell thickness and position (including motion artifacts), and excitation intensity. Emission ratios usually change by larger percentages than either emission wavelength signal alone, because the donor and acceptor emissions should change in opposite directions, which reinforce each other when ratioed. If emission ratioing is not desirable or possible, either wavelength can still be used alone, or the change in donor excited-state lifetime monitored.

Emission ratios are measured either by changing the passband of a wavelength-selective filter in front of a single detector, or preferably by splitting the emitted light with a dichroic mirror and measuring two wavelength bands simultaneously with two detectors, which may each be preceded by additional wavelength-selecting filters. In the first method, the wavelength-selective filters may be two or more interference filters with different passbands alternately placed in front of the detector, or they may be a continuously tunable monochromator which is repeatedly scanned over a wavelength range. The advantage of the first method is that only one detector is used, which economizes on detectors and avoids the problem of precisely matching two detectors. The advantages of the second method, using a dichroic mirror and two separate detectors, are that the two emissions may be measured truly simultaneously rather than sequentially, and that it makes more efficient use of the photons emitted from the sample.

FRET between a luminescent component and fluorescent component may be preferred in certain circumstances. Because this approach does not require light irradiation of the sample, phototoxicity and autofluorescence of the sample are significantly reduced. Because light emission is exclusively produced from the luminescent component, the approach typically exhibits improved specificity and sensitivity. However because the luminescent component typically creates significantly less light output than is achieved using traditional fluorescent approaches it is often necessary to use more sensitive detectors, and to collect and integrate light emission over time compared to fluorescent emission ratioing.

Another preferred detection method involves the use of time resolved fluorescence approaches. These methods combine many of the advantages of the use of fluorescence, with the enhanced specificity and freedom from autofluorescence, of luminescence based measurements.

The methods generally encompass the use of a long-lived fluorescent component to provide sustained light emission in the absence of illumination. Typical components include lanthanides such as terbium or europium chelates covalently joined to a polynuclear heterocyclic aromatic sensitizer (for example described in U.S. Pat. No. 5,622,821, issued Apr. 22, 1997) as the first or second reagent. These reagents are preferred because they are relatively easy to synthesize and attach to macromolecules, are highly fluorescent, chemically stable and good resonance energy transfer donors.

The time resolved analysis requires a pulsed excitation source and gated detectors to enable the transient illumination of the sample and decay of sample autofluorescence. By making fluorescence measurements after the decay of autofluorescence, the assay method typically exhibits significantly improved signal to noise ratios compared to traditional fluorescence based approaches. Instrumentation for conducting time resolved analysis is commercially available from a number of sources including Hewlett-Packard, LKB, and LJL.

Molecular specificity for particular cell types in a mixed population may be further improved by the use of targetable reagents. For example, cell-specific antibodies or lectins as the carriers of the extracellular fluorescent label, or by using naturally fluorescent, or bioluminescent proteins specifically expressed in a given cell type as the intra- or extracellular label. Specifically labeled cells can also reduce background staining and therefor provide larger fluorescence changes, particularly in complex tissues, where not all the cells may respond to a given stimulus.

High sensitivity is achieved when the voltage sensor (i.e., the hydrophobic anion of the first reagent) translocates at least a full unit charge nearly all the way through the membrane. Even without specific ion channels or transporters, such translocation can be quite rapid if the ion is negatively charged, delocalized, and hydrophobic. For example, the lipid-soluble non-fluorescent anion of dipicrylamine (2,2',4,4',6,6'-hexanitrodiphenylamine) produces displacement currents in excitable tissue with submillisecond kinetics, comparable in speed to sodium channel gating currents [Benz, R. and Conti, F. 1981. Structure of the squid axon membrane as derived from charge-pulse relaxation studies in the presence of absorbed lipophilic ions. *J. Membrane Biol.* 59:91–104; Benz, R. and Nonner, W. 1981. Structure of the axolemma of frog myelinated nerve: relaxation experiments with a lipophilic probe ion. *J. Membrane Biol.* 59:127–134; Fernandez, J. M., Taylor, R. E., and Bezanilla, F. 1983. Induced capacitance in the squid giant axon. *J. Gen. Physiol.* 82:331–346]. However, voltage sensing should not require further diffusion of the ion through the unstirred aqueous layers, because that slows the response and generates a sustained leakage current.

To create an optical readout from the translocation of the fluorescent hydrophobic ion (i.e., the first reagent) from one side of the biological membrane to the other side, FRET or fluorescence quenching between the translocating ion and a fluorophore or quencher (i.e., the second reagent) fixed to just one face of the membrane is employed. Most conveniently, the extracellular face is employed.

Figure 1B:
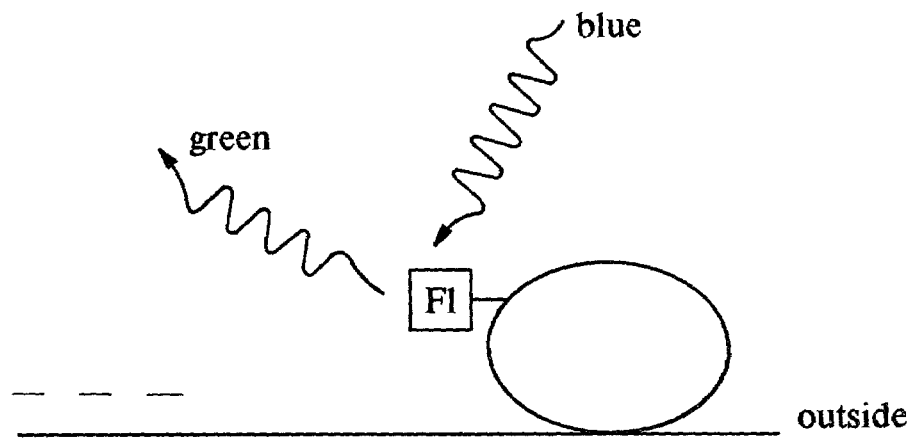
Figure 1B:
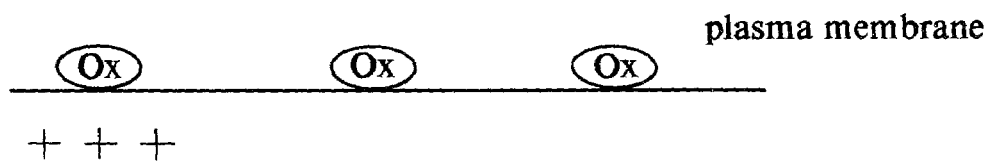

By way of example, and not limitation, the case where the translocating ions are anionic fluorescent acceptors which absorb at wavelengths that overlap with the emission spectrum of the extracellularly fixed donor fluorophores is schematically shown in FIG. 1. At a resting negative membrane potential (A) permeable oxonols have a high concentration at the extracellular surface of the plasma membrane and energy transfer from the extracellularly bound FL-WGA (fluorescein-wheat germ agglutinin) is favored. FRET is symbolized by the straight arrow from lectin to oxonol. At a positive membrane potential (B) the anions are located primarily on the intracellular surface of the membrane and energy transfer is greatly reduced because of their increased mean distance from the donors on the extracellular surface.

Figure 5:
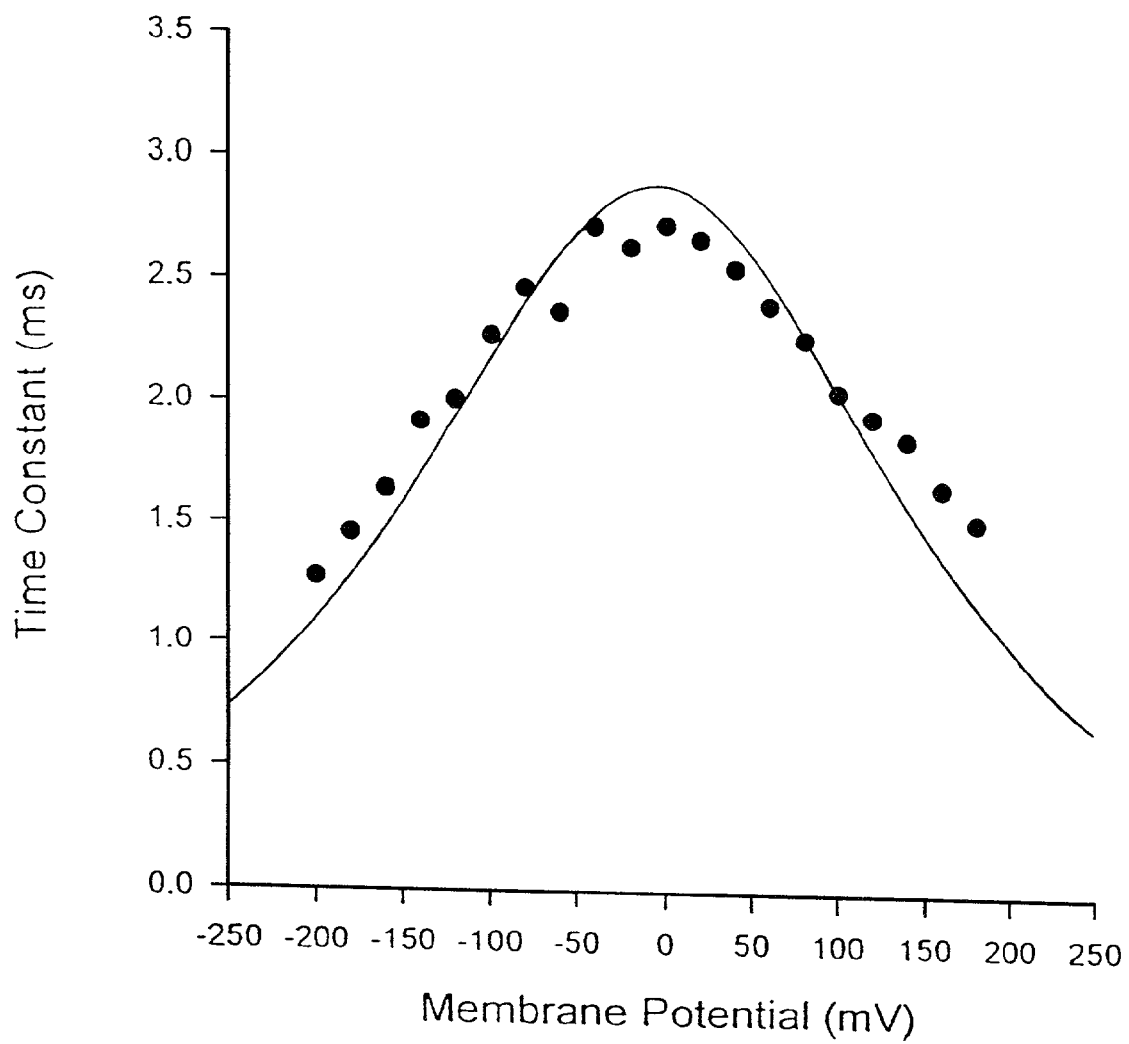
FIG. 5 illustrates voltage dependence of DiSBA-$C_6$-(3) displacement current time constants in L-M(TK$^-$)cells for the same data shown in FIG. 4.

The speed of the voltage-sensitive fluorescence response depends on the translocation rate of the fluorophore from one site to the other. The speed of response for DiSBA-$C_6$-(3) is shown in FIG. 5 and follows the general equations (1) and (2). As this equation indicates, fluorescent ions which jump across the membrane on a millisecond timescale in response to biologically significant changes in transmembrane potential are needed to follow rapid polarization/depolorization kinetics. Slower-jumping ions would not be useful, for example, in following fast electrical signals in neuronal tissue (a primary application of the compositions and methods of the present invention). The development and discovery of such molecules with the added constraint of being fluorescent is not trivial.

The mobile hydrophobic anions can be donors rather than acceptors. Each of the alternatives has its own advantages. An example with the hydrophobic ion being the FRET donor is the DiSBA-$C_6$-(3)/Texas Red WGA combination. A primary advantage of this arrangement is that it minimizes the concentration of the hydrophobic dye molecule in the membrane; this reduces toxicity and cellular perturbations resulting from the displacement current and any photodynamic effects. Another advantage is the generally higher quantum yields of fluorophores bound in membranes relative to those on proteins or water; this gives better FRET at a given distance.

Bis-(1,3-dialkyl-2-thiobarbiturate)-trimethineoxonols, where alkyl is n-hexyl and n-decyl (DiSBA-$C_6$-(3) and DiSBA-$C_{10}$-(3) respectively) have been shown herein to function as donors to Texas Red labeled wheat germ agglutinin (TR-WGA) and as acceptors from fluorescein labeled lectin (FL-WGA). In voltage-clamped fibroblasts, the translocation of these oxonols was measured as a displacement current with a time constant of about 2 ms for 100 mV depolarization at 20 C, which equals the speed of the fluorescence changes. Fluorescence ratio changes of between 4–34% were observed for a 100 mV depolarization in fibroblasts, astrocytoma cells, beating cardiac myocytes, and B104 neuroblastoma cells. The large fluorescence changes allowed high speed confocal imaging.

Single cells were used in the examples so that the optical signals could be compared with voltage changes accurately known from traditional microelectrode techniques, such as patch clamping, which are applicable only to single cells. However, it should be apparent that the dyes can be used for many applications in which microelectrodes are not applicable. Comparison with microelectrodes is needed merely for accurate calibration and proof that the mechanism of fluorescence signal generation is gas described herein. The two reagent compositions and methods described herein can either resolve the different electrical potentials of many neighboring cells or neighboring parts of a single cell, or give an average reading for all the membrane locations, depending on whether the optical signal is spatially imaged or pooled.

The methods described herein are applicable to a wide variety of membranes. In particular, membrane potentials in membranes of isolated cells, tissues and intact transgenic organisms can be detected and monitored. The method finds greatest utility with plasma membranes, especially the outermost plasma membrane of mammalian cells. Representative membranes include, but are not limited to, subcellular organelles, membranes of the endoplasmic reticulum, secretory granules, mitochondria, microsomes and secretory vesicles. Cell types which can be used include but are not limited to, neurons, cardiac cells, lymphocytes (T and B lymphocytes, nerve cells, muscle cells and the like.

VIII. Drug Screening

The invention also provides methods for screening test samples such as potential therapeutic drugs that affect membrane potentials in biological cells. These methods involve measuring membrane potentials as described above in the presence and absence (control measurement) of the test sample. Control measurements are usually performed with a sample containing all components of the test sample except for the putative drug. Detection of a change in membrane potential in the presence of the test agent relative to the control indicates that the test agent is active. Membrane potentials can be also be determined in the presence or absence of a pharmacologic agent of known activity (i.e., a standard agent) or putative activity (i.e., a test agent). A difference in membrane potentials as detected by the methods disclosed herein allows one to compare the activity of the test agent to that of the standard agent. It will be recognized that many combinations and permutations of drug screening protocols are known to one of skill in the art and they may be readily adapted to use with the method of membrane potential measurement disclosed herein to identify compounds which affect membrane potentials. Use of the membrane potential determination technique disclosed herein in combination with all such methods are contemplated by this invention. In a particular application, the invention offers a method of identifying a compound which modulates activity of an ion channel, pump, or exchanger in a membrane, comprising:

(a) loading the cells with the first and second reagents, which together measure membrane potential as described above;

(b) determining the membrane potential as described above;

(c) exposing the cells to the test sample;

(d) redetermining the membrane potential and comparing with the result in (b) to determine the effect of the test sample;

(e) optionally, exposing the membrane to a stimulus which modulates an ion channel, pump or exchanger, and redetermining the membrane potential and comparing with the result in (d) to determine the effect of the test sample on the response to the stimulus.

In another application, the invention offers a method of screening test samples to identify a compound which modulates the activity of an ion channel, pump or exchanger in a membrane, comprising:

(a) loading a first set and a second set of cells with first and second reagents which together measure membrane potential;

(b) optionally, exposing both the first and second set of cells to a stimulus which modulates the ion channel, pump or exchanger;

(c) exposing the first set of cells to the test sample;

(d) measuring the membrane potential in the first and second sets of cells; and (e) relating the difference in membrane potentials between the first and second sets of cells to the ability of a compound in the test sample to modulate the activity of an ion channel, pump or exchanger in a membrane.

In another aspect the method includes the use of a membrane potential modulator to set the resting, or stimulated membrane potential to a predefined value. At this predefined value the cell is unable to rapidly reset the membrane potential in response to the transient activation of the target ion channel. Thus as a result of the artificial membrane potential, even transient activation of the target ion channel leads to a prolonged, measurable change in membrane potential that is typically larger and more conveniently measured during screening. This method enables the detection of very transient ion channel currents, which are normally difficult to measure in a convenient format. Such channels include rapidly inactivating sodium channels, T-type calcium channels and ligand-gated channels.

In another aspect of this method, the membrane potential modulator comprises a ligand dependent ion channel. Activation of the ligand gated ion channel causes a voltage change in the cell that provides the stimulus to activate a voltage-dependent channel target. The ligand can be added directly or released via UV flash uncaging to enable rapidly inactivating voltage dependent ion channels to be monitored.

This approach enables voltage activated ion channels to be activated without using traditional electrophysiological (i.e. voltage clamp or patch clamp) methods, that are not readily amendable to high throughput screening.

Ion channels of interest include, but are not limited to, sodium, calcium, potassium, nonspecific cation, and chloride ion channels, each of which may be constitutively open, voltage-gated, ligand-gated, or controlled by intracellular signaling pathways.

Biological cells which can be screened include, but are not limited to primary cultures of mammalian cells, transgenic organisms and mammalian tissue. Cells in screening assays may be dissociated either immediately or after primary culture. Cell types include, but are not limited to white blood cells (e.g. leukocytes), hepatocytes, pancreatic beta-cells, neurons, smooth muscle cells, intestinal epithelial cells, cardiac myocytes, glial cells, and the like. The invention also includes the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel) and methods for their expression in cell lines of interest is within the knowledge of one of skill in the art (see, U.S. Pat. No. 5,436,128). Representative cultured cell lines derived from humans and other mammals include LM (TK−) cells, HEK293 (human embryonic kidney cells), 3T3 fibroblasts, COS cells, CHO cells, RAT1 and HLHepG2 cells.

The screening methods described herein can be made on cells growing in or deposited on solid surfaces. A common technique is to use a microtiter plate well wherein the fluorescence measurements are made by commercially available fluorescent plate readers. The invention includes high throughput screening in both automated and semiautomated systems, such as described in PCT publication No. WO 98/52047, and U.S. patent application Ser. No. 09/122,544 filed Jul. 24, 1999 entitled "Detector and Screening Device for Ion Channels." One such method is to use cells in Costar 96 well microtiter plates (flat with a clear bottom) and measure fluorescent signal with CytoFluor multiwell plate reader (Perseptive Biosystems, Inc., MA) using two emission wavelengths to record fluorescent emission ratios.

The invention may be better understood with reference to the accompanying examples, which are intended for purposes of illustration only and should not be construed as in any sense limiting the scope of the invention as defined in the claims appended hereto.

EXAMPLES

Example I

Synthesis of Oxonol Dyes

All starting materials and reagents were of the highest purity available (Aldrich; Milwaukee, Wis.) and used without further purification, except where noted. Solvents were HPLC grade (Fisher) and were dried over activated molecular sieves 3Å. NMR spectra were acquired on a Varian Gemini 200 MHz spectrometer (Palo Alto, Calif.). The spectra were referenced relative to the residual solvent peak ($CHCl_3$, =7.24 ppm). Fluorescence spectra were taken on a SPEX Fluorolog-2 (Edison, N.J.) and were corrected for lamp and detector wavelength variations using the manufacturer supplied correction files.

Bis-(1,3-dibutyl-2-thiobarbiturate)-trimethineoxonol DiSBA-$C_4$-(3)

DiSBA-$C_4$-(3) was synthesized based on the procedure for the ethyl derivative [British Patent 1,231,884]. 1,3-dibutyl-thiobarbiturate (500 mg, 2 mmol) was dissolved in 700 μL of pyridine. To this solution, a mixture of 181 μL (1.1 mmol) of malonaldehyde bis(dimethyl acetal) and 100 μL of 1 M HCl was added. The solution immediately turned red. After 3 h, half of the reaction mixture was removed and 2 equiv. of the protected malonaldehyde was added every hour for 4 h to the remaining mixture. The reaction mixture was then filtered to collect purple/black crystals of the DiSBA-$C_4$-(3) pyridinium salt. After washing the crystals with water and then drying under vacuum (0.5 torr), 67.2 mg of pure product was collected. $^1$H NMR ($CDCl_3$): 8.91 (2H, d, J=5.1 Hz, py), 8.76 (1H, t, J=13.7 Hz, central methine), 8.52 (1H, t, J=8.0 Hz, py), 8.16 (2H, d, J=13.9 Hz, methine), 8.00 (2H, dd, $J_1$~$J_2$=6.9 Hz, py), 4.47 (8H, cm, NC$\underline{H}_2$CH$_2$CH$_2$CH$_3$), 1.69 (8H, cm, NCH$_2$C$\underline{H}_2$CH$_2$CH$_3$), 1.39 (8H, cm, NCH$_2$CH$_2$C$\underline{H}_2$CH$_3$), 0.95 (12H, t, J=6.4 Hz, methyl).

To prepare 1,3-di-butyl-thiobarbiturate, 1.22 g of Na (53 mmol) was slowly dissolved in 20 mL of dry ethanol under argon. To the ethoxide solution, 8.5 g (8 mL, 53 mmol) of diethyl malonate followed by 5 g (26.5 mmol) of dibutylthiourea were added. The reaction mixture was heated and refluxed for 3 days. After cooling, the mixture was filtered. The filtrate was clarified with addition of water. Concentrated HCl was then added until the pH was 1–2. The acidic filtrate was then extracted 3× with hexanes. The extract was concentrated and 5.5 g of crude product precipitated out of solution. The solid was recrystallized from methanol with addition of small amounts of water yielding 4.23 g of the pure barbituric acid (65%). 1H NMR (CDCl$_3$): 4.33 (4H, cm, NCH$_2$CH$_2$CH$_2$CH$_3$), 3.71 (2H, s, ring CH$_2$), 1.63 (4H, cm, NCH$_2$CH$_2$CH$_2$CH$_3$), 1.35 (4H, cm, NCH$_2$CH$_2$CH$_2$CH$_3$), 0.94 (6H, t, J=6.2 Hz, methyl).

Bis-(1,3-dihexyl-2-thiobarbiturate)-pentamethineoxonol (DiSBA-C$_6$-(5)): 1,3-dihexyl-2-thiobarbituric acid (200 mg, 0.64 mmol) and glutacondialdehyde dianil monohydrochloride (whose Chem. Abs. name is N-[5-(phenylamino)-2,4-pentadienylidene]benzenamine, monohydrochloride) (91 mg, 0.32 mmol) were mixed in 1 mL pyridine. Within 10 s, the solution turned blue. After letting the reaction mixture stir for 1.5 h, the solvent was removed under high vacuum. The residue was dissolved in CHCl$_3$ and chromatographed on silica gel eluting with a (93:7) CHCl$_3$/MeOH solution. The pure blue oxonol (72 mg) was recovered. $^1$HNMR (CDCl$_3$/CD$_3$OD): d 7.60–7.80 (cm, 4H, methines), 7.35 (t, J=1 1.3 Hz, 1H, central methine), 4.31 (cm, 8H, NCH$_2$R), 1.57 (cm, 8H, NCH$_2$CH$_2$R), 1.20 (br m, 24H, bulk methylenes), 0.74 (br t, 12H, methyl).

Figure 13:
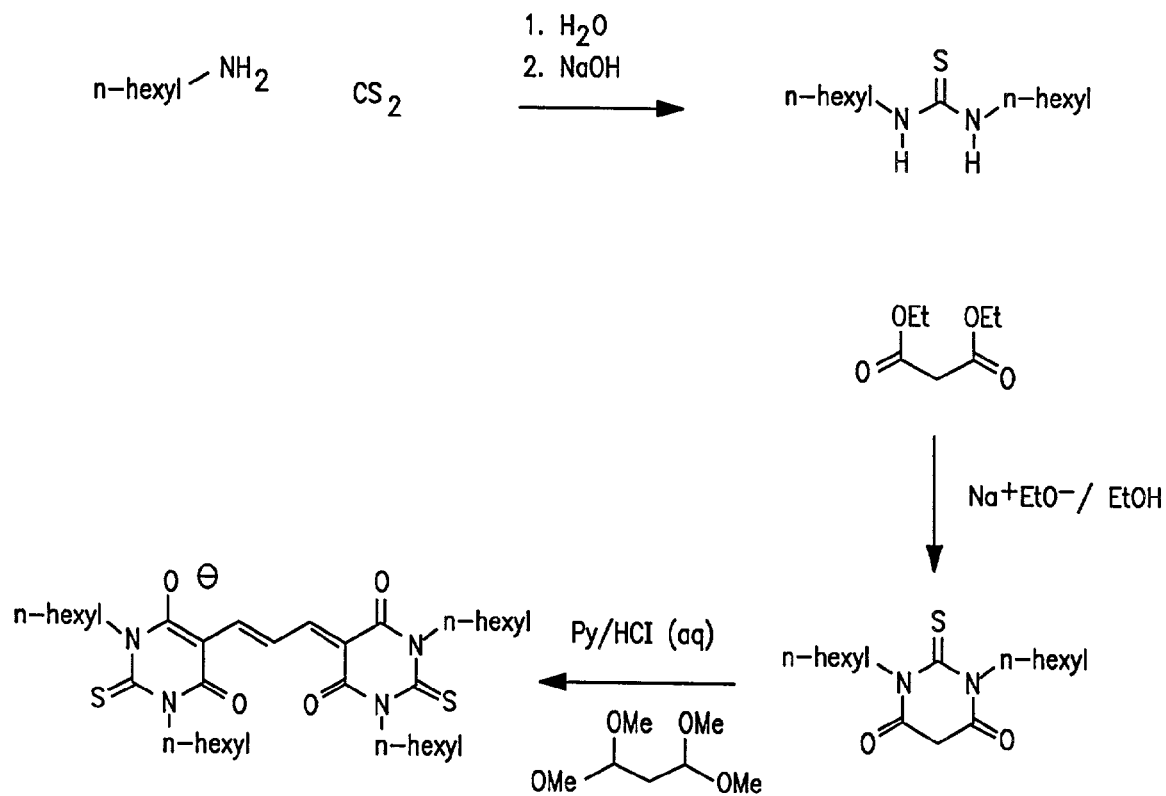
FIG. 13 shows a synthesis of Di-SBA-$C_6$-(3).

Other oxonols were made using the same procedure, starting with the appropriate thiourea prepared from requisite primary amine and carbon disulfide [Bortnick, N., Luskin, L. S., Hurwitz, M. D., and Rytina, A. W. 1956. t-Carbinamines,RR'R"CNH$_2$. III. The preparation of isocyanates, isothiocyanates and related compounds. *J. Am. Chem. Soc.* 78:4358–4361]. An exemplary synthesis of Di-SBA-C$_6$-(3) is depicted in FIG. 13.

Example II

Synthesis of Fluorescent Phospholipids

Cou-PE: 3-amidoglycine-6-chloro-7-butyryloxy coumarin was synthesized as described in pending U.S. patent application, Ser. No. 08/407,554, filed Mar. 20, 1995 as set out below. For synthesis of 2,4 dihydroxy-5-chlorobenzaldehyde, 21.7 g (0.15 Mol) 4-chlororesorcinol were dissolved in 150 ml dry diethyl ether and 27 g finely powdered zinc (II) cyanide and 0.5 g potassium chloride were added with stirring. The suspension was cooled on ice. A strong stream of hydrogen chloride gas was blown into the solution with vigorous stirring. After approximately 30 minutes the reactants were dissolved. The addition of hydrogen chloride gas was continued until it stopped being absorbed in the ether solution (approx. 1 hour). During this time a precipitate formed. The suspension was stirred for one additional hour on ice. Then the solid was let to settle. The ethereal solution was poured from the solid. The solid was treated with 100 g of ice and heated to 100 degrees C. in a water bath. Upon cooling the product crystallized in shiny plates from the solution. They were removed by filtration on dried over potassium hydroxide. The yield was 15.9 g (0.092 Mol, 61%). $^1$H NMR (CDCl$_3$): 6.23 ppm (s, 1H, phenol), 6.62 ppm (s, 1H, phenyl), 7.52 ppm (s, 1H, phenyl), 9.69 ppm (s, 1H, formyl), 11.25 ppm (s, 1H, phenol).

To prepare 3-carboxy 6-chloro 7-hydroxy coumarin, 5.76 g (0.033 Mol) 2,4-dihydroxy-5-chlorobenzaldehyde and 7.2 g (0.069 Mol) malonic acid were dissolved in 5 ml warm pyridine. 75 microliters aniline were stirred into the solution and the reaction let to stand at room temperature for 3 days. The yellow solid that formed was broken into smaller pieces and 50 ml ethanol was added. The creamy suspension was filtered through a glass frit and the solid was washed three times with 1 N hydrochloric acid and then with water. Then the solid was stirred with 100 ml ethyl acetate, 150 ml ethanol and 10 ml half concentrated hydrochloric acid. The solvent volume was reduced in vacuo and the precipitate recovered by filtration, washed with diethyl ether and dried over phosphorous pentoxide. 4.97 g (0.021 Mol, 63%) of product was obtained as a white powder. $^1$H NMR (dDMSO): 6.95 ppm (s, 1H), 8.02 ppm (s, 1H), 8.67 ppm (s, 1H).

To prepare 7-butyryloxy-3-carboxy-6-chlorocoumarin, 3.1 g (12.9 mMol) 3-carboxy-6-chloro-7-hydroxycoumarin were dissolved in 100 ml dioxane and treated with 5 ml butyric anhydride, 8 ml pyridine and 20 mg dimethyl aminopyridine at room temperature for two hours. The reaction solution was added with stirring to 300 ml heptane upon which a white precipitate formed. It was recovered by filtration and dissolved in 150 ml ethyl acetate. Undissolved material was removed by filtration and the filtrate extracted twice with 50 ml 1 N hydrochloric acid/brine (1:1) and then brine. The solution was dried over anhydrous sodium sulfate. Evaporation in vacuo yielded 2.63 g (8.47 mMol, 66%) of product. $^1$H NMR (CDCl$_3$): 1.08 ppm (t, 3H, J=7.4 Hz, butyric methyl), 1.85 ppm (m, 2H, J$_1$ J$_2$=7.4 Hz, butyric methylene), 2.68 ppm (t, 2H, J=7.4 Hz, butyric methylene), 7.37 ppm (s, 1H, coumarin), 7.84 ppm (s, 1H, coumarin), 8.86 ppm (s, 1H, coumarin).

Preparation of 7-butyryloxy-3-benzyloxycarbonylmethylaminocarbonyl-6-chlorocoumarin is effected as follows. 2.5 g (8.06 mMol) 7-Butyryloxy-3-carboxy-6-chlorocoumarin, 2.36 g hydroxybenztriazole hydrate (16 mMol) and 1.67 g (8.1 mMol) dicyclohexyl carbodiimide were dissolved in 30 ml dioxane. A toluene solution of O-benzylglycine [prepared by extraction of 3.4 g (10 mMol) benzylglycine tosyl salt with ethyl acetate—toluene—saturated aqueous bicarbonate—water (1:1:1:1, 250 ml), drying of the organic phase with anhydrous sodium sulfate and reduction of the solvent volume to 5 ml] was added dropwise to the coumarin solution. The reaction was kept at room temperature for 20 hours after which the precipitate was removed by filtration and washed extensively with ethylacetate and acetone. The combined solvent fractions were reduced to 50 ml on the rotatory evaporator upon which one volume of toluene was added and the volume further reduced to 30 ml. The precipitating product was recovered by filtration and dissolved in 200 ml chloroform—absolute ethanol (1:1). The solution was reduced to 50 ml on the rotatory evaporator and the product filtered off and dried in vacuo yielding 1.29 g of the title product. Further reduction of the solvent volume yielded a second crop (0.64 g). Total yield: 1.93g (4.22 mMol, 52%). $^1$H NMR (CDCl$_3$): 1.08 ppm (t, 3H, J=7.4 Hz, butyric methyl), 1.84 ppm (m, 2H, J$_1$ J$_2$=7.4 Hz, butyric methylene), 2.66 ppm (t, 2H, J=7.4 Hz, butyric methylene), 4.29 ppm (d, 2H, J=5.5 Hz, glycine methylene), 5.24 ppm (s, 2H, benzyl), 7.36 ppm (s, 1H, coumarin), 7.38 ppm (s, 5H, phenyl), 7.77 ppm (s, 1H, coumarin), 8.83 ppm (s, 1H, coumarin), 9.15 ppm (t, 1H, J=5.5 Hz, amide).

7-Butyryloxy-3-carboxymethylaminocarbonyl-6-chlorocoumarin was prepared as follows. 920 mg (2 mMol) 7-butyryloxy-3-benzyloxycarbonylmethylaminocarbonyl-6- chlorocoumarin were dissolved in 50 ml dioxane. 100 mg palladium on carbon (10%) and 100 microliters acetic acid were added to the solution and the suspension stirred vigorously in a hydrogen atmosphere at ambient pressure. After the uptake of hydrogen seized the suspension was filtered. The product containing carbon was extracted five times with 25 ml boiling dioxane. The combined dioxane solutions were let to cool upon which the product precipitated as a white powder. Reduction of the solvent to 20 ml precipitates more product. The remaining dioxane solution is heated to boiling and heptane is added until the solution becomes cloudy. The weights of the dried powders were 245 mg, 389 mg and 58 mg, totaling 692 mg (1.88 mMol, 94%) of white product. $^1$H NMR (dDMSO): 1.02 ppm (t, 3H, J=7.4 Hz, butyric methyl), 1.73 ppm (m, 2H, $J_1$ $J_2$=7.3 Hz, butyric methylene), 2.70 ppm (t, 2H, J=7.2 Hz, butyric methylene), 4.07 ppm (d, 2H, J=5.6 Hz, glycine methylene), 7.67 ppm (s, 1H, coumarin), 8.35 ppm (s, 1H, coumarin), 8.90 ppm (s, 1H, coumarin), 9.00 ppm (t, 1H, J=5.6 Hz, amide).

6-chloro-7-(n-butyryloxy)coumarin-3-carboxamidoacetic acid (26.2 mg, 100 mmol) was dissolved in 2 mL of 1:1 CHCl$_3$/dioxane. Isobutylchloroformate (14.3 mL, 110 mmol) was added under Argon at 4° C. and left stirring for 30 min. Separately, dimyristoylphosphatidylethanolamine (DMPE) (20 mg, 31.5 mmol) was dissolved in 1 mL of CHCl$_3$ with 1 drop of dry MeOH and 6 mL (34.5 mmol) of diisopropylethylamine (DIEA) added. The mixed anhydride solution was then pipetted into the phospholipid solution. After 2 h, the solvent was removed under vacuum. The residue was dissolved in 3 mL of MeOH and mixed with 3 mL of 0.25 M NaHCO$_3$. The solution almost immediately turn yellow and was stirred for 15 min. The solution was then extracted 3–5 times with CHCl$_3$. A bad emulsion is formed. The extracts were combined and concentrated. The residue was dissolved in 1 mL 1:1 MeOH/H$_2$O and purified on a C$_{18}$ reverse phase column (1.7×7 cm). Eluting with the same solvent, a fluorescent band passed through the column, followed by a slower one. The solvent polarity was decreased to 9:1 MeOH/H$_2$O and the major yellow band then eluted off the column. After concentration and drying 2.5 mg (2.74 mmol) of pure product was collected. $^1$HNMR (CD$_3$OD): d 8.72 (s, 1H, coumarin), 7.81 (s, 1 H, coumarin), 6.84 (s, 1H, coumarin), 5.25 (cm, 2H), 4.43 (dd, $J_1$=12.1 Hz, $J_2$=3.2 Hz), 4.22 (d, J=6.6 Hz, 1H), 4.13 (s, ~4H), 3.7–4.1 (cm, ~11 H), 3.47 (cm, ~3H), 3.2–3.3 (~q), 2.31 (cm~7H), 1.57 (br s, ~8H, CH$_2$ a to carbonyl), 1.2–1.5 (cm, ~63H, bulk CH$_2$'s), 0.92 (unrest, ~12 H, CH$_3$). Electrospray (neg. ion) MS [MeOH/H$_2$O: 95/5] (peak, rel. int.) 456.8 (M$^{-2}$, 20), 524.5 (50), 704.9 (6), 734.7 (100), 913.9 (M$^{-1}$, 95); deconvoluted M=915.3 amu; calc. M=915.5 amu. UV-vis (MeOH/HBSS; 2/1) 1$_{max}$=414 nm. Fluorescence (MeOH/HBSS; 2/1) 1$_{emax}$=450 nm, Quantum Yield=1.0.

Cy5-PE: DMPE (1.0 mg, 1.6 mmol) was dissolved in 650 mL of (12:1) CHCl$_3$/MeOH and DIEA (1 mL, 5.7 mmol) was added. Separately, Cy5-OSu (Amersham; Arlington Heights, Ill.), the N-hydroxysuccinimide ester of N-ethyl-N'-(5-carboxypentyl)-5,5'-disulformdodicarbocyanine, (0.8 mg, 1 mmol) was dissolved in 150 mL of (2:1) CHCl$_3$/MeOH and added to the phospholipid solution. After 3 h, the solvent was removed under vacuum. The residue was dissolved in MeOH and loaded on a C$_{18}$ reverse phase column (1×10 cm) equilibrated with 1:1 MeOH/H$_2$O. Eluting with the same solvent, the hydrolyzed ester was removed. The polarity was decreased to 9:1 MeOH/H$_2$O and the pure blue product was eluted off the column, yielding 400 mg (310 nmol, 31%).

Example III

Synthesis of Linker for Donors and Acceptors

Figure 14:
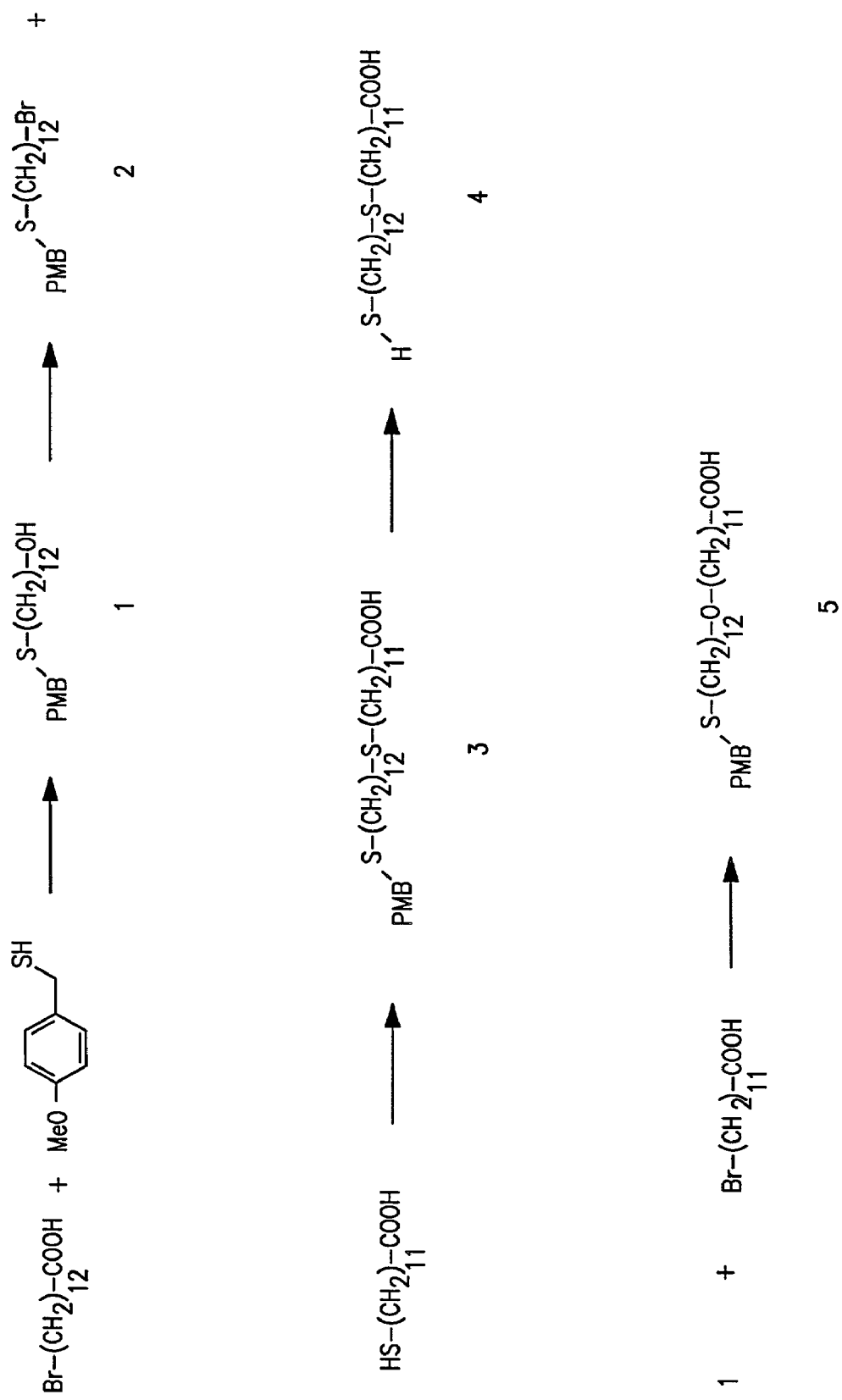
FIG. 14 shows the synthesis of a bifunctional linker.
Figure 15:
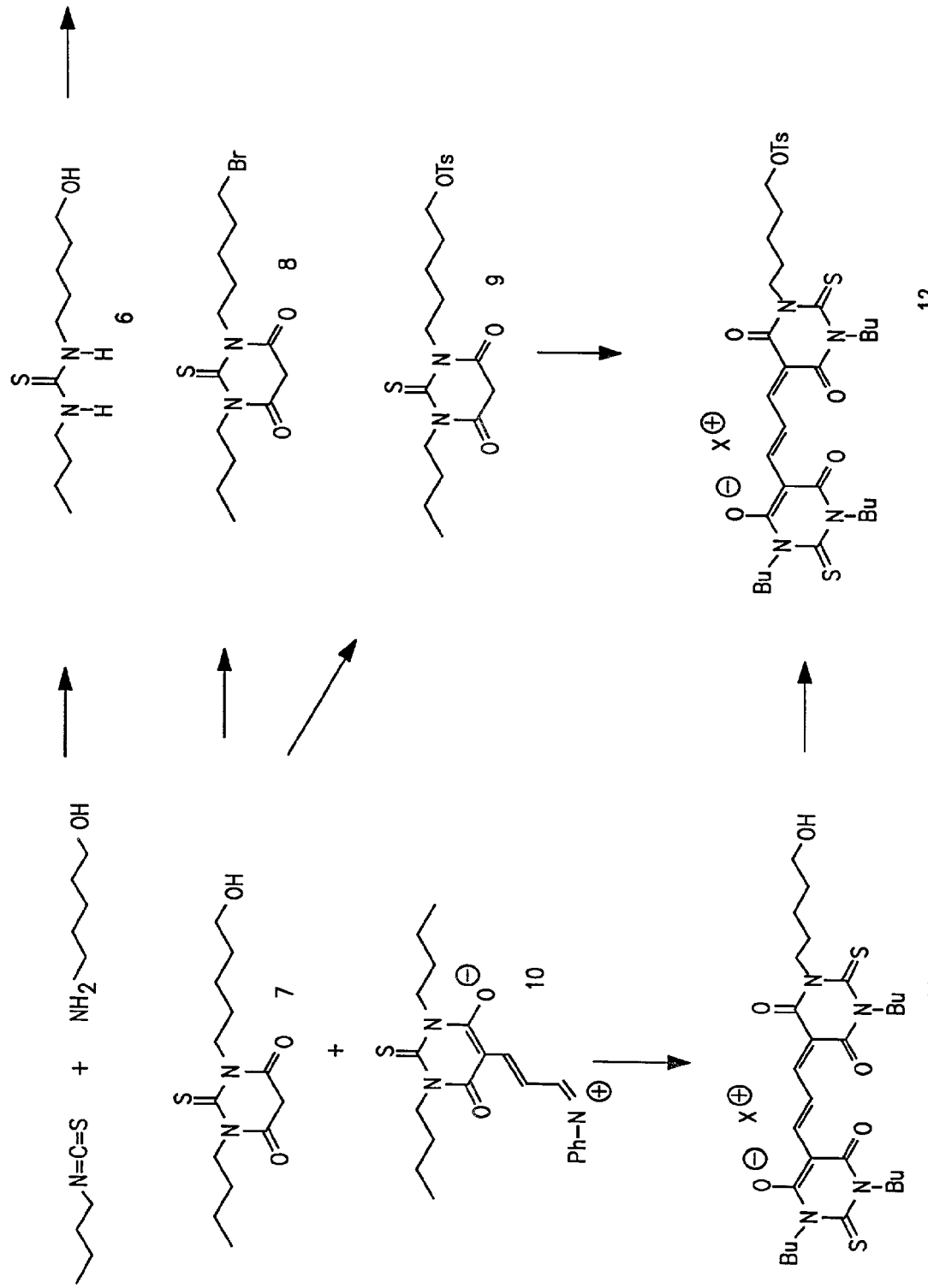
FIGS. 15 and 16 show the synthesis of an asymmetric oxonol with a linker suitable for attachment to a second reagent.
Figure 16:
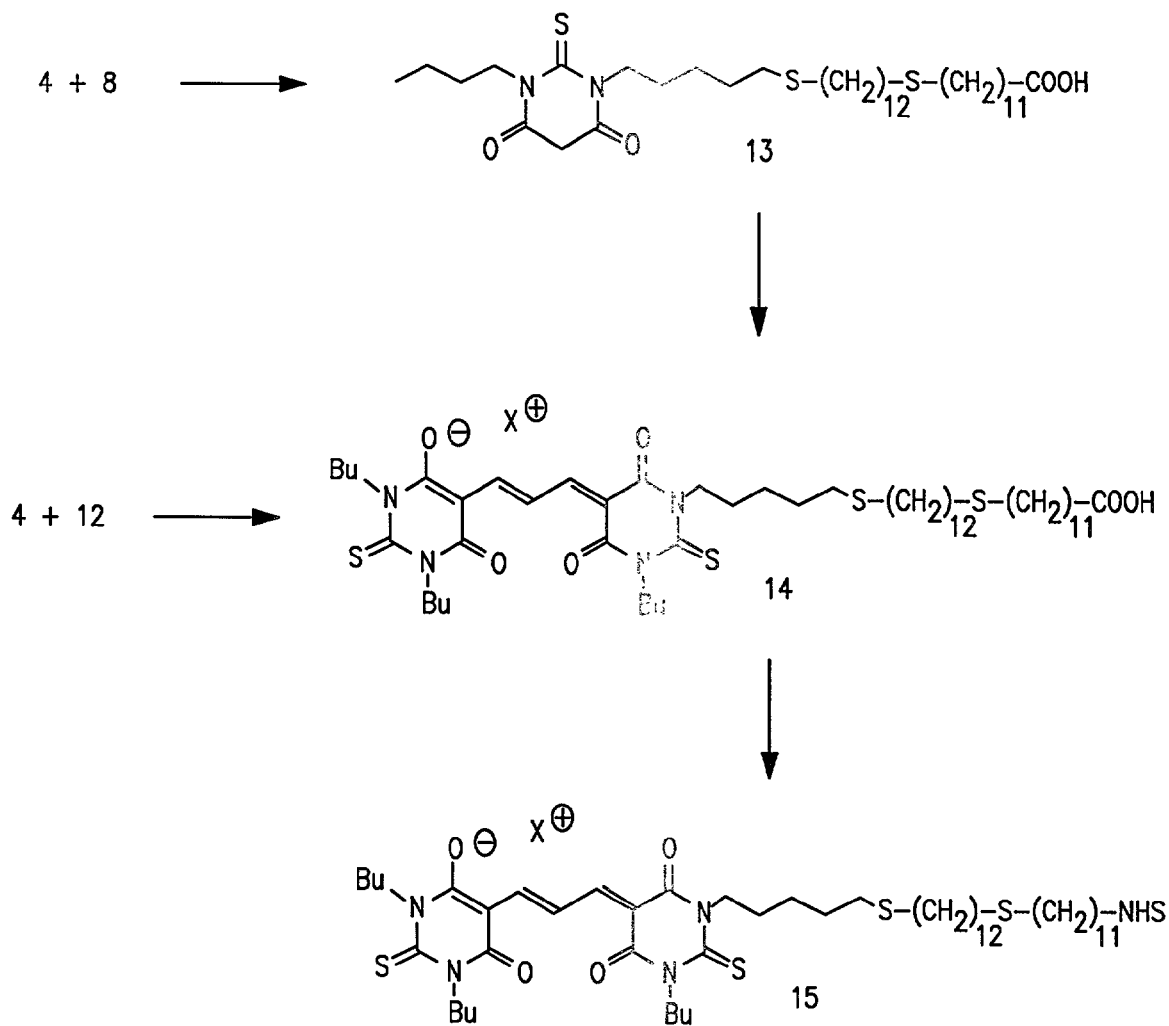

This example is with reference to FIGS. 14–16.

12-p-methoxybenzylthio-1-dodecanol (1): Na (800 mg, 34.8 mmol) was dissolved in 30 mL of dry MeOH. Under argon, p-methoxybenzylmercaptan (2.75 mL, 3.04 g, 19.7 mmol) was added to the methoxide solution. After a few minutes, 12-bromododecanol (2.5 g, 9.43 mmol) was dropped into the reaction mixture. Within 5 minutes a solid began to come out of solution. After a minimum of 3 h, the reaction was filtered and washed 3× with cold MeOH, yielding 2.874 g (8.49 mmol, 90%) of pure product after drying. $^1$H NMR (CDCl$_3$): d 7.23 (d, J=8.8 Hz, 2H, AA' of AA' BB' aromatic system), 6.85 (d, J=8.8 Hz, 2H, BB' of AA' BB' aromatic system), 3.80 (s, 3H, methoxy), 3.66 (s, 2H, benzyl), 3.64 (dt, $J_1$=6.6 Hz, $J_2$=5.5 Hz, 2H, RCH$_2$OH), 2.40 (t, J=7.3 Hz, 2H, RSCH$_2$R), 1.50–1.65 (cm, 4H, CH$_2$ b to heteroatoms), 1.2–1.4 (cm, 16H, bulk methylenes).

12-p-methoxybenzylthio-1-bromododecane (2): (1) (500 mg, 1.48 mmol) was mixed with carbon tetrabromide (611 mg, 1.85 mmol) in 2.5 mL CH$_2$Cl$_2$ and cooled in an ice bath until solid began to come out of solution. The ice bath was removed and triphenylphosphine (348 mg, 2.22 mmol) was added to the reaction. The solution immediately turned yellowish. The starting material had been consumed after 30 min according to TLC (EtOAc/Hex, 1:1). The solvent was removed and 50 mL of hexane was added to the solid residue. After stirring overnight, the solution was filtered and concentrated to a solid. The solid was then mixed with about 10–15 mL of hexane and again filtered. The concentrated filtrate yielded 537 mg (1.34 mmol, 91%) of pure product after drying. $^1$H NMR (CDCl$_3$): d 7.23 (d, J=8.6 Hz, 2H, AA' of AA' BB' aromatic system), 6.85 (d, J=8.7 Hz, 2H, BB' of AA' BB' aromatic system), 3.80 (s, 3H, methoxy), 3.67 (s, 2H, benzyl), 3.41 (t, J=6.9 Hz, 2H, RCH$_2$Br), 2.40 (t, J=7.3 Hz, 2H, RSCH$_2$R), 1.86 (cm, 2H, CH$_2$ b to Br), 1.15–1.45 (cm, 18H, bulk methylenes).

12-(12-p-methoxybenzylthio-1-dodecylthio)-dodecanoic acid (3): Na (116 mg, 5 mmol) was dissolved it dry MeOH. 12-mercapto-1-dodecanoic acid (340 mg, 1.46 mmol)—synthesized according to JACS 115, 3458–3474, 1993 was added to the methoxide solution. After stirring with some heating for 5 min, (2) (497 mg, 1.24 mmol) was added to the reaction. The reaction became very viscous and an additional 1.75 mL of MeOH was introduced. The reaction was then left overnight. The reaction was quenched with 10% acetic acid. The paste-like reaction mixture was transferred to a 500 mL separatory funnel dissolved in equal volumes of EtOAc/Hex (1:1) and the acetic acid solution. The organic layer was separated. The aqueous layer was then extracted two more times. The combine extracts were concentrated yielding 740.3 mg (1.34 mmol) of crude product. The excess acetic acid was removed as a toluene azeotrope. The solid was crystallized from isopropyl ether giving 483 mg (71%). TLC and NMR show an impurity believed to be a disulfide side product. The material was further purified by flash chromatography eluting with CHCl$_3$/MeOH/AA (99:0.5: 0.5) yielding 334 mg (0.604 mmol, 49%) of pure product. $^1$H NMR (CDCl$_3$): d 9.45 (brs, 1H, COOH), 7.23 (d, J=8.8 Hz, 2H, AA' of AA' BB' aromatic system), 6.85 (d, J=8.7 Hz, 2H, BB' of AA' BB' aromatic system), 3.80 (s, 3H, methoxy), 3.66 (s, 2H, benzyl), 2.50 (t, J=7.3 Hz, 4H, RCH$_2$SCH$_2$R), 2.40 (t, J=7.3 Hz, 2H, RSCH$_2$R), 2.35 (t, J=7.5 Hz, 2H, RCH$_2$COOH), 1.5–1.7 (cm, 8H, CH$_2$ b to heteroatoms), 1.15–1.45 (cm, 30H, bulk methylenes). $^{13}$C NMR (CDCl$_3$):

d 179.5 (COOH), 129.9 (aromatic, 2C), 113.9 (aromatic, 2C), 55.2 (MeOR), 35.6 ($CH_2$), 33.7 ($CH_2$), 32.2 ($CH_2$), 31.3 ($CH_2$), 29.7 ($CH_2$), 29.4 ($CH_2$), 29.2 ($CH_2$), 28.9 ($CH_2$), 24.6 ($CH_2$).

1-butyl-3-(12-(12-pentylthio-1-dodecylthio)-dodecanoic acid) thiobarbiturate (13): (3) (73.8 mg, 133.5 µmol) was deprotected in 2 mL of dry TFA/anisole (14:1) at 70° C. for 2.5 h. The solvent was removed under vacuum and the residue was dissolved in 10 mL dry EtOH. Sodium borohydride (330 mg) was added and the mixture was stirred overnight. The solution was then acidified with conc. HCL until gas stopped evolving. The solution was then extracted with ether 4×. The combined extracts were concentrated leaving a white solid. The solid was then dissolved and concentrated 2× with degassed MeOH. After drying on the high vacuum, 69.5 mg of solid was recovered. It was estimated by TLC that this solid was 1:1 the deprotected product and di-p-methoxyphenylmethane, (104 µmol, 78%). The deprotected linker was dissolved in 0.5 mL dry DMF, with heating. NaH (~550 µmol) was added which caused some gas evolution. (8) (38.5 mg, ~100 µmol) was then added to the reaction in 100 uL DMF and the reaction was left overnight at 60° C. TLC in EtOAc/MeOH/AA (90:8:2) indicated that a new more non-polar barbituric acid had been formed. The solvent was removed and the residue was dissolved in EtOAc/Hex (1:1) and washed with water. The material was then purified by chromatography, eluting with EtOAc/MeOH/AA (90:8:2). NMR of the product showed resonance from barbituric acid and the linker. Electrospray (neg. ion) MS [MeOH/$H_2O$: 95/5] (peak, rel. int.) 516.4 (95), 699.4 ($M^{-1}$, 100), 715.1 ($M^{-1}$+16, 40), 1024.0 ($M^{-1}$+32, 25); calc. $M^{-1}$=700.1 amu. The ether linkers appears to be partially oxidized to sulfoxides.

1-(1,3-dibutyl thiobarbiturate)-3-(1-butyl-3-(12-(12-pentylthio-1-dodecylthio)-dodecanoic acid) thiobarbiturate) trimethineoxonol (14): (3) (73.8 mg, 133.5 mol) was deprotected in 2 mL of dry TFA/anisole (14:1) at 70° C. for 2.5 h. The solvent was removed under vacuum and the residue was dissolved in 20 mL dry EtOH. Sodium borohydride (330 mg) was added and the mixture was stirred overnight. The solution was then acidified with conc. HCL until gas stopped evolving. The solution was then extracted with ether 4×. The combined extracts were concentrated leaving a white solid. The solid was then dissolved and concentrated 2× with degassed MeOH. After drying on the high vacuum, 71.1 mg of solid was recovered. It was estimated by TLC that this solid was 1:1 the deprotected product and di-p-methoxyphenylmethane, (106 µmol, 79%). The deprotected linker was dissolved in 1 mL dry DMF, with heating. NaH (~350 µmol) was added which caused some gas evolution. (12) (35.5 µmol) was then added to the reaction in 200 µL DMF. The reaction did not seem to be proceeding after 1 h, so 4 mg of N.H. (60%) was added to the reaction mixture. The solution now appeared orange instead of red and a second non-polar oxonol began to form. The reaction, heated at 60° C., was allowed to go for 18 h. Half of the reaction mixture was worked up as follows. The reaction mixture was transferred to a 30 mL separatory funnel in 12 mL toluene. About 4 mL a 10% acetic acid solution and 3 mL of water were added. Most of the oxonol partitioned into the organic layer, which was washed 3× with acetic acid solution/water (1:1). The organic layer was then concentrated and purified by flash chromatography (2.5×18 cm). The column was packed and first eluted with $CHCl_3$/MeOH/AA (93:5:2). After 1 non-polar oxonol was removed, the solvent polarity was increased to $CHCl_3$/MeOH/AA (90:8:2). This caused the oxonol product to elute off the column. After concentrating the fractions and drying, 7.2 mg pure product (7.25 µmol, 20%) was attained. $^1$H NMR ($CDCl_3$/MeOH): d 8.54 (t, J=13.8 Hz, 1H, central methine), 7.97 (d, J=14.2 Hz, 2H, methines), 4.39 (cm, 8H, $NCH_2R$), 2.46 (t, J=7.3 Hz, 8H, $RCH_2SCH_2R$), 2.2 (t, 2H, $RCH_2COOH$), 1.5–18 (bulk methylenes), 1.2–1.4 (bulk methylenes), 0.92 (t, J=7.2 Hz, 9H, methyls). Electrospray (neg. ion) MS [MeOH/$H_2O$: 95/5] (peak, rel. int.) 683 (50), 977.8 (30), 992.1 ($M^{-1}$, 100), 1008.1 ($M^{-1}$+16, 40), 1024.0 ($M^{-1}$+32, 10); calc. $M^{-1}$=992.5 amu. The +16 and +32 peaks suggest oxidation of thioethers to sulfoxide groups. (14) has also been successfully synthesized from (13) using (10) in a similar fashion as that described in the synthesis of (11).

1-(1,3-dibutyl thiobarbiturate)-3-(1-butyl-3-(12-(12-pentylthio-1-dodecylthio)-N-hydroxysuccinimide dodecanoate) thiobarbiturate) trimethineoxonol (15):

22.5 µmol of (14) was reacted with disuccinimidyl carbonate (57 mg, 225 µmol) in 0.5 mL $CH_2Cl_2$ in the presence of DIEA (39 µL, 225 mmol). After 1.5 hours, TLC (EtOAc/MeOH) (9:1) indicated that 3 new non-polar bands had been formed. The solvent was removed and two non-polar oxonol bands were purified by flash chromatography, eluting with (EtOAc/MeOH) (95:5). Electrospray (neg. ion) MS [MeOH/$H_2O$: 95/5] (peak, rel. int.) 1089.3 ($M^{-1}$, 20), 1105.1 ($M^{-1}$+16, 100), 1121.0 ($M^{-1}$+32, 60); calc. $M^{-1}$=1089.5 amu.

Example IV

Measurement of Membrane Potential with Oxonol Dyes as Fret Acceptors and Fluorescent Lectins as Fret Donors FL-WGA was purchased from Sigma Chemical Co. (St. Louis, Mo.). TR-WGA was prepared from WGA and Texas Red (Molecular Probes; Eugene, Oreg.) in a 100 mM bicine buffer at pH 8.5. A 73 µM solution of WGA was reacted with a 6-fold excess of Texas Red for 1 h at room temperature. The protein conjugate was purified on a G-25 Sephadex column.

All cells were grown and handled like L-M(TK⁻) except where noted. L-M(TK⁻) cells were grown in Dulbecco's Modified Eagle Media (Gibco; Grand Island, N.Y.) with 10% fetal bovine serum (FBS) and 1% penicillin streptomycin (PS) (Gemini; Calabasas, Calif.). B104 cells were differentiated with 1 µM retinoic acid for 5 days prior to use. The cells were plated on glass coverslips at least one day before use. The adherent cells were washed and maintained in 2.5–3.0 mL of HBSS with 1 g/L glucose and 20 mM HEPES at pH 7.4. A freshly prepared 75 µM aqueous solution of the appropriate oxonol was made prior to an experiment from a DMSO stock solution. The cells were stained by mixing 100 µL of the oxonol solution with 750 µL of the bath and then adding the diluted solution to the cells. The dye was left for 30–40 minutes at a bath concentration of 2.3 M. 1.5 mM β-cyclodextrin in the bath solution was necessary for cell loading of DiSBA-$C_6$-(3). The butyl and ethyl derivatives were water-soluble enough to load cells with out β-cyclodextrin complexation. DiSBA-$C_{10}$-(3) was loaded in a pH 7.4 solution containing 290 mM sucrose and 10 mM HEPES, 364 mOsm, for 10 min at a bath concentration of 10 M. DiSBA-$C_{10}$-(3) labeling was quenched by replacing the bath with HBSS solution. The cells were stained with 15 g/mL of FL-WGA for 15 minutes. The B104 cells required a 125 g/mL bath concentration to give satisfactory lectin staining. The excess dyes were removed with repeated washes with HBSS. If the excess ethyl or butyl oxonol derivatives were left in the bath, slow currents and fluorescence changes due to redistribution of the dyes into the cell were observed during depolarizations greater than 1 s. The cardiac myocytes [Henderson, S. A., Spencer, M., Sen, A., Kumar, C., Siddiqui, M. A. Q., and Chien, K. R. 1989. Structure organization, and expression of the rat cardiac myosin light chain-2 gene. *J. Biol. Chem.* 264: 18142–18146] were a gift of Professor Kenneth Chien, UCSD. The Jurkat lymphocyte suspensions were grown in RPMI media with 5% heat inactivated FBS and 1% PS. 15–20 mL aliquots of the cellular suspension were washed three times before and after dye staining by centrifugation at 100× g for 4 minutes followed by additions of fresh HBSS.

The fluorescently labeled cells were excited with light from a 75 W xenon lamp passed through 450–490 nm excitation interference filters. The light was reflected onto the sample using a 505 nm dichroic. The emitted light was collected with a 63× Zeiss (1.25 or 1.4 numerical aperture) lens, passed through a 505 nm long pass filter and directed to a G-1B 550 nm dichroic (Omega; Brattleboro, Vt.). The reflected light from this second dichroic was passed through a 515 DF35 bandpass filter and made up the FL-WGA signal. The transmitted light was passed through a 560 or 570 LP filter and comprised the oxonol signal. For experiments using the oxonol as a donor to TR-WGA, the 550 nm dichroic was used for excitation and a 580 nm dichroic was used to split the emission. The long wavelength Texas Red fluorescence was passed through a 605 nm DF55 bandpass filter. Voltage dependent fluorescence changes in single cells were measured using a Nikon microscope attached to a Photoscan II photometer equipped with two R928 PMTs for dual emission recordings. A 7-point Savitsky-Golay smoothing routine was applied to all optical data [Savitsky, A. and Golay, M. J. E. 1964. Smoothing and differentiation of data by simplified least squares procedure. *Anal. Chem.* 36:1627–1639], unless otherwise noted. The 1–2 KHz single wavelength data was acquired with an Axobasic program that used the TTL pulse counting routine LEVOKE. Confocal images were acquired using a home built high speed confocal microscope [Tsien, R. Y. and B. J. Bacskai. 1994. Video-rate confocal microscopy. In Handbook of Biological Confocal Microscopy. J. B. Pawley, editor. Plenum Press, New York]. The cell was voltage-clamped at a holding potential of −70 mV. After a 200 ms delay, the cell was given a 200 ms depolarizing square voltage pulse to 50 mV. Pseudocolor images showing the ratio of the FL-WGA to oxonol emissions were collected every 67 ms and clearly showed a change in ratio, localized to the plasma membrane, upon depolarization of the cell to +50 mV.

Patch clamp recording were made using an Axopatch 1-D amplifier equipped with a CV-4 headstage from Axon Instruments (Foster City, Calif.). The data were digitized and stored using the PCLAMP software. The pH 7.4 intracellular solution used contained 125 mM potassium gluconate, 1 mM $CaCl_2.2H_2O$, 2 MM $MgCl_2.6H_2O$, 11 mM EGTA, and 10 mM HEPES. For the B104 cells, 4 mM ATP and 0.5 mM GTP were added.

The quantum yield of DiSBA-$C_6$-(3) was determined relative to rhodamine B in ethanol ($f$=0.97) [Weber, G. and Teale, F. W. K. 1957. Determination of the absolute quantum yield of fluorescent solutions. Faraday Soc. Trans. 53:646–655]. $R_O$ was calculated following standard procedures [Wu, P. and Brand, L. 1994. Resonance energy transfer: methods and applications. *Anal. Biochem.* 218:1–13]. The spectra of FL-WGA in HBSS and DiSBA-$C_6$-(3) in octanol were used to determine the overlap integral. Values of 1.4 and 0.67 were used for the index of refraction and orientation factor respectively.

Figure 2:
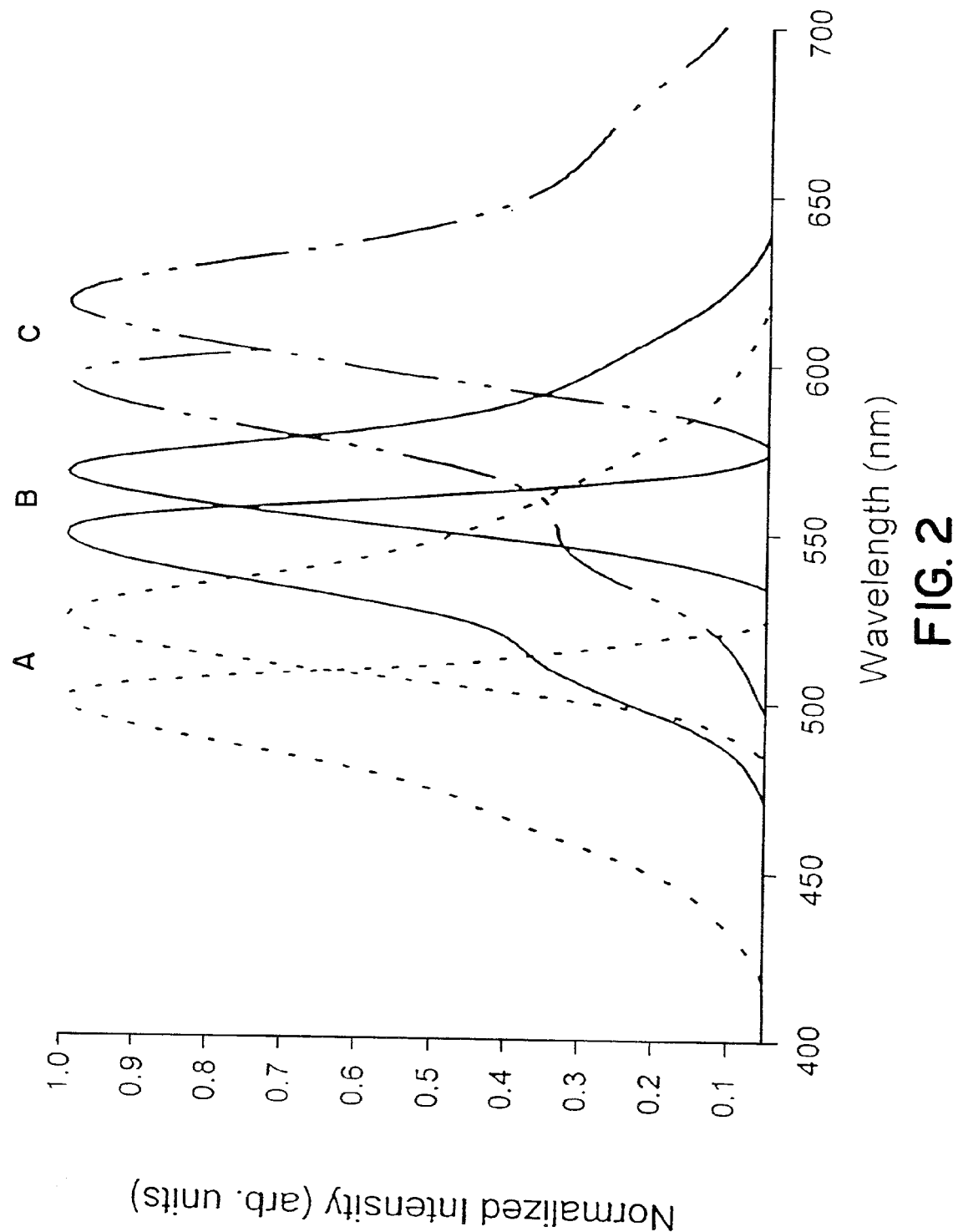
FIG. 2 illustrates normalized excitation and emission spectra for (A) fluorescein-labeled wheat germ agglutinin (FL-WGA) in Hanks' Balanced Salt Solution (HBSS), (B) (1,3-dihexyl-2-thiobarbiturate)trimethine oxonol [DiSBA-$C_6$-(3)] in octanol, and (C) TR-WGA in HBSS.

Symmetrical bis(thiobarbiturate)oxonols were chosen as likely candidates for rapidly translocating fluorescent ions based on the above design criteria. The strong absorbance maximum (~200,000 $M^{-1}cm^{-1}$) at 540 nm and good quantum yield (0.40) in membranes makes them desirable for use as a fluorescence donors or acceptors in cells. The fluorescence excitation and emission spectra of DiSBA-$C_6$-(3) is shown in FIG. 2 along with those for FL-WGA and TR-WGA. The excitation spectra are the shorter of each pair. Octanol was selected as the oxonol solvent in order to mimic the membrane environment.

The translocation rates were studied in L-M(TK$^-$) cells using whole-cell voltage clamp recording. The L-M(TK$^-$) cells were chosen because they have very low background currents and are easy to patch clamp. These cells have a resting potential of −5 mV and no evident voltage activated currents.

Figure 3:
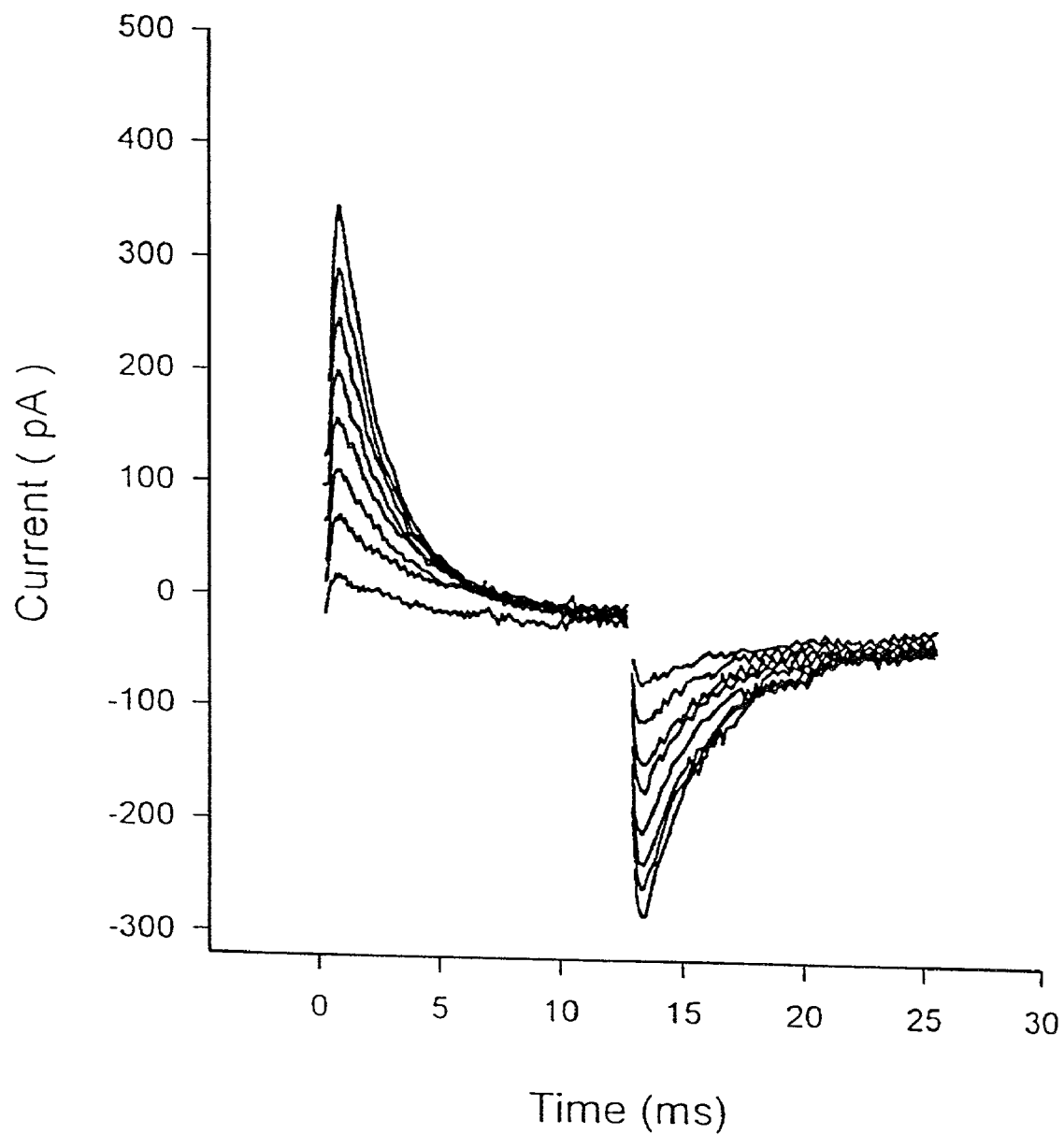
FIG. 3 illustrates displacement currents of 2.3 M DiSBA-$C_6$-(3) in L-M(TK$^-$) cells at 20 C.

Displacement currents from DiSBA-$C_6$-(3) at 20 C are displayed in FIG. 3. 12.5 ms long voltage steps at 15 mV increments were applied to the cell, from a holding potential of −70 mV. The larger, faster transients due to simple membrane capacitance transient could be minimized using the capacitance and series resistance compensation capabilities of the Axopatch amplifier, allowing the displacement currents to be clearly observed. The currents are due to redistribution of the membrane-bound oxonol in response to 8 depolarizations. The time constant for the displacement current is 2 ms for 120 mV depolarization. Equal amounts of charge move at the onset and conclusion of the voltage step, but in opposite directions, consistent with redistribution of stored ions from one energy minimum to the other across the plasma membrane. Furthermore, the induced capacitance dq/dV from the oxonol movement is calculated to be ~5 pF for 100 mV depolarization. This value corresponds to roughly one third the membrane capacitance without the dye. Interestingly, sodium channel gating charges are also responsible for about 33% of the total capacitance of squid axons for small depolarizations [Hodgkin, A. 1975. The optimum density of sodium channels in an unmyelinated nerve. *Philos. Trans. R. Soc. Lond. [Biol]* 270:297–300]. Negligible currents were observed in the absence of the oxonol. DiSBA-$C_{10}$-(3) gave displacement currents of approximately the same speed, whereas analogues with R=butyl and ethyl gave much slower currents. The butyl compound had a time constant of ~18 ms and the currents from the ethyl compound were very small, slow, and difficult to observe.

Figure 4:
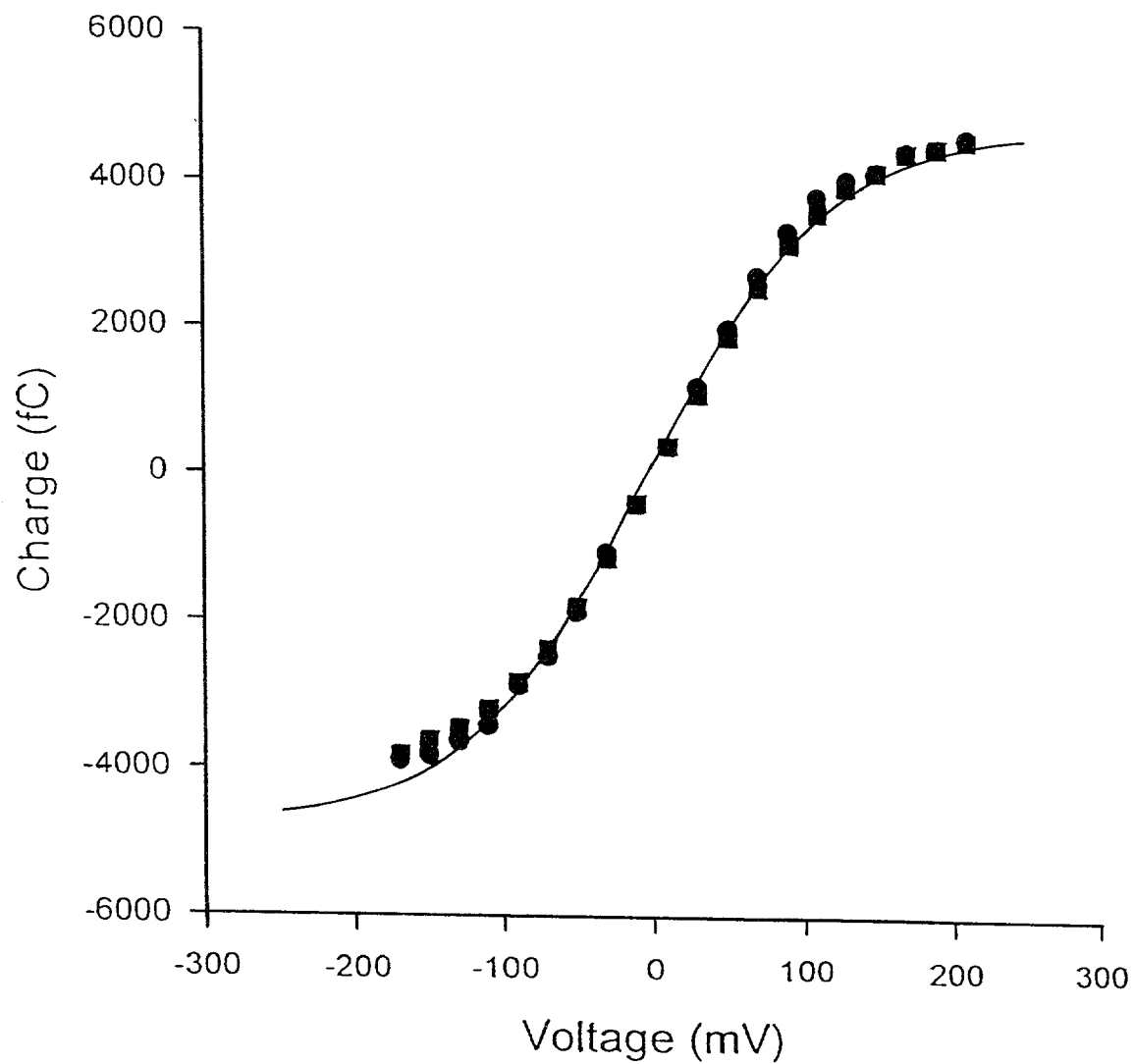
FIG. 4 illustrates voltage dependence of DiSBA-$C_6$-(3) moved during the displacement and tailcurrents for step voltage changes from a −30 mV holding potential.

FIGS. 4 and 5 show the voltage dependence and time constants for charge translocation in a cell loaded with about 4 times as much oxonol as in the experiment of FIG. 3. In FIG. 4, the circles are the data from the on response and the squares from the tail currents. The raw data were fit to a single exponential and the charge moved, the area, was calculated as the product of the current amplitude and the time constant. The experimental data are in reasonable accord with existing models of hydrophobic ion transport between two energy minima near the aqueous interfaces of the lipid bilayer [Ketterer, B., Neumcke, B., and Läuger, P. 1971. Transport mechanism of hydrophobic ions through lipid bilayer membranes. *J. Membrane Biol.* 5:225–245; Andersen, O. S. and Fuchs, M. 1975. Potential energy barriers to ion transport within lipid bilayer. *Biophys. J.* 15:795–830; Benz, R., Läuger, P., and Janko, K. 1976. Transport kinetics of hydrophobic ions in lipid bilayer membranes. *Biochim. Biophys. Acta* 455:701–720]. These models predict that the equilibrium charge displacement q(V) and the translocation time constant (V) should depend on the externally applied membrane potential V in the following manner:

$$\Delta q(V) = \Delta q_{max} \tanh\left[\frac{q\beta(V-V_h)}{2kT}\right] \quad (1)$$

$$\tau(V) = \tau_{max} \operatorname{sech}\left[\frac{q\beta(V-V_h)}{2kT}\right] \quad (2)$$

$V_h$, the membrane potential at which there are equal numbers of ions in each potential energy well, could differ from zero because of membrane asymmetry. β is the fraction of the externally applied potential effectively felt by the translocating ion; q is the charge on each ion, k and T are Boltzmann's constant and absolute temperature. $q_{max}$ and $_{max}$ are respectively the total charge in each energy well and the time constant for translocation, both at $V=V_h$. The smooth curve in FIG. 4 is the fit to Eq. 1 with $q_{max}$=4770±140 fC, β=0.42±0.02, and $V_h$=−3.8±1.5 mV. Likewise the smooth curve in FIG. 5 is the fit to Eq. 2 with $_{max}$=2.9 ms at $V_h$=−5 mV and β=0.42.

These results demonstrate that the oxonol senses a significant part of the electric field across the membrane, that it translocates in ~3 ms or less, and that the greatest sensitivity and linearity of translocation as a function of membrane potential is in the physiologically relevant range.

To transduce charge displacements into optical signals, the oxonol fluorescences at the intracellular and extracellular membrane binding sites is made different. Fluorescence asymmetry is created with the introduction of fluorescently labeled lectins bound to the extracellular membrane surface. Excitation of FL-WGA leads to energy transfer to oxonols located in the extracellular membrane binding site as shown in FIG. 1. The extinction coefficient and the fluorescence quantum yield of FL-WGA were measured to be 222,000 $M^{-1}cm^{-1}$ (~3 fluorescein/protein) and 0.23, respectively. In Jurkat cell suspensions labeled with FL-WGA, up to 30% of the lectin fluorescence intensity was quenched upon titration of DiSBA-$C_4$-(3). In the best case where all of the quenching is due to energy transfer, the average distance from the lectin to the membrane-bound oxonol is still greater than 50 Å, the calculated Förster distance $R_O$ for the FL-WGA/oxonol pair. The spectral overlap between the FL-WGA emission and DiSBA-$C_6$-(3) excitation is given in FIG. 2. Because FRET falls off with the inverse sixth power of the distance separating the two fluorophores, energy transfer to oxonols in the intracellular membrane site, an additional 40 Å away, is probably negligible.

Figure 6:
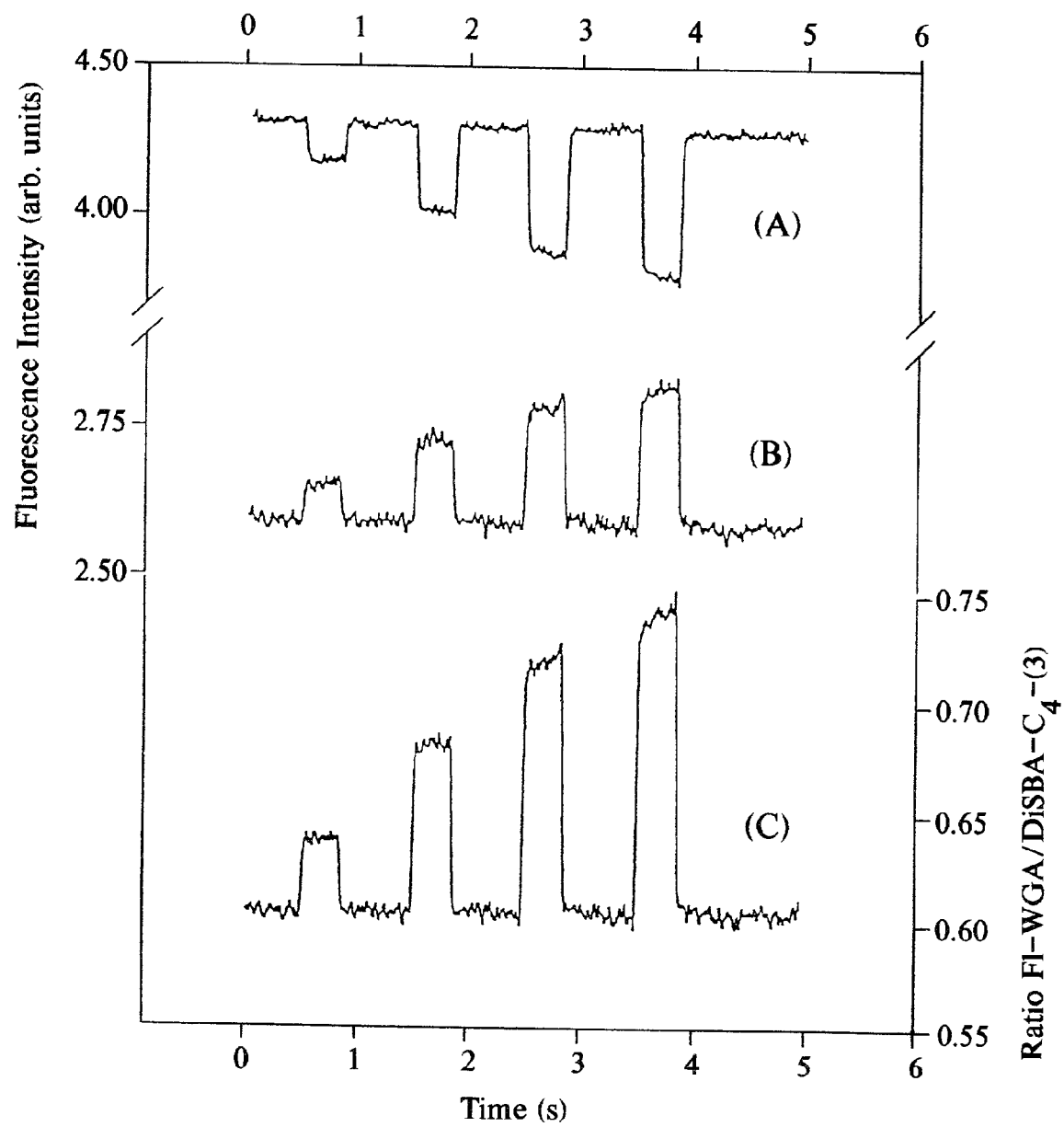
FIG. 6 illustrates simultaneous fluorescence changes of the FL-WGA/DiSBA-$C_4$-(3) pair in response to 4 depolarizations from −70 mV of 40, 80, 120, and 160 mV in a L-M(TK-) cell at 20 C, with the single wavelength fluorescence emission traces of DiSBA-$C_4$-(3) and FL-WGA being shown in panels A and B, respectively, and the FL-WGA/DiSBA-$C_4$-(3) ratio displayed in (C)

Upon depolarization, the oxonol molecules redistribute such that more are bound to the intracellular site and less to the extracellular one. This change manifests itself with a decrease in the energy transfer, resulting in an increase in the fluorescence of the FL-WGA and a concomitant decrease in the oxonol emission. The fluorescence signals in a voltage clamped L-M(TK⁻) cell labeled with (the DiSBA-$C_4$-(3)/FL-WGA pair) and depolarized with four increasing voltage steps are shown in FIG. 6. The data are the average of 29 sweeps. The FL-WGA emission increases 7–8%, the oxonol fluorescence decreases 10% and the FL-WGA/oxonol emission ratio changes 19% for a 120 mV depolarization. The simultaneous changes in donor and acceptor emissions is consistent with the FRET mechanism outlined in FIG. 1. The decrease in oxonol emission with depolarization is opposite to what is observed for the slow voltage-sensitive uptake of oxonols in cells [Rink et al. 1980, supra]. The fluorescence changes have time constants of ~18 ms at 20 C, in agreement with the DiSBA-$C_4$-(3) displacement currents. No large fluorescence changes are observed in the absence of FL-WGA. The translocation rate of DiSBA-$C_4$-(3) speeds up with increasing temperature. The time constant falls to 7–8 ms at 29 C, corresponding to an activation energy of ~17 kcal/mol. However, raising the temperature also increases internalization of the lectin and eventually decreases the fluorescence change. The oxonols with R=ethyl and butyl also reach internal cellular membranes, though active membrane internalization is probably not necessary. Additional dilution of the voltage-dependent FRET signals arises from spectral overlap of the fluorescein and oxonol, such that some of the light in the fluorescein emission channel comes from the oxonol and vice versa.

Figure 7:
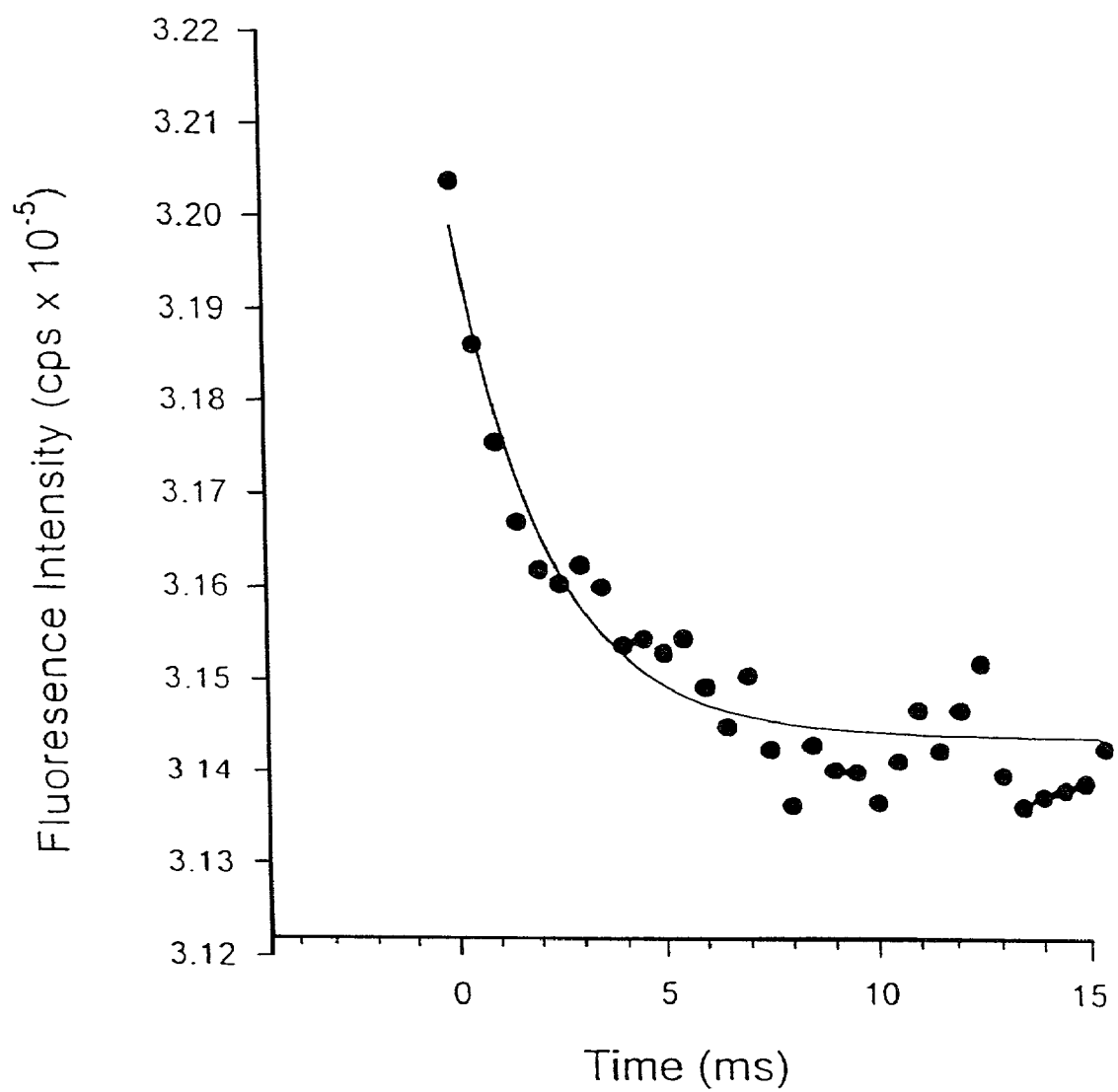
FIG. 7 illustrates the time course of the fluorescence change of the FL-WGA/DiSBA-$C_{10}$-(3)pair in response to a 100 mV depolarization from −70 mV.

Increasing the length of the alkyl chains on the oxonol improves the response times significantly. The DiSBA-$C_6$-(3)/FL-WGA pair, has a time constant of ~3 ms at 20 C, while the DiSBA-$C_{10}$-(3)/FL-WGA pair, responds with a time constant of 2 ms, as shown in FIG. 7. The solid curve is a fit to a single exponential with a 2 ms time constant. The data is the average of 3 L-M(TK⁻) cells, at 20 C, acquired at 2 kHz. The response in the figure is slightly slower than the true value because of smoothing. The fluorescence time constants are in agreement with those from the displacement currents, for example in FIG. 3. The beneficial effect of adding hydrophobicity to the oxonol in the form of longer alkyl chains reaches a plateau. There is a large 6-fold increase in translocation rate substituting hexyl for butyl on the oxonol core. However, addition of twice as many methylene groups in going from the hexyl to the decyl compound results in less than a 2-fold increase. These faster translocating oxonols are essentially insoluble in water and require modified procedures to load into cells. DiSBA-$C_6$-(3) is easily loaded in normal medium supplemented with 1.5 mM β-cyclodextrin to complex the alkyl chains. Nonfluorescent DiSBA-$C_6$-(3) aggregates in Hanks Balanced Salt Solution (HBSS) become fluorescent upon addition of β-cyclodextrin. DiSBA-$C_{10}$-(3) requires loading in a medium of low ionic strength with osmolarity maintained with sucrose. Labeling is confined almost exclusively to the plasma membrane, presumably because the hydrophobicity is now great enough to prevent desorption from the first membrane the dye encounters.

Example V

Figure 17:
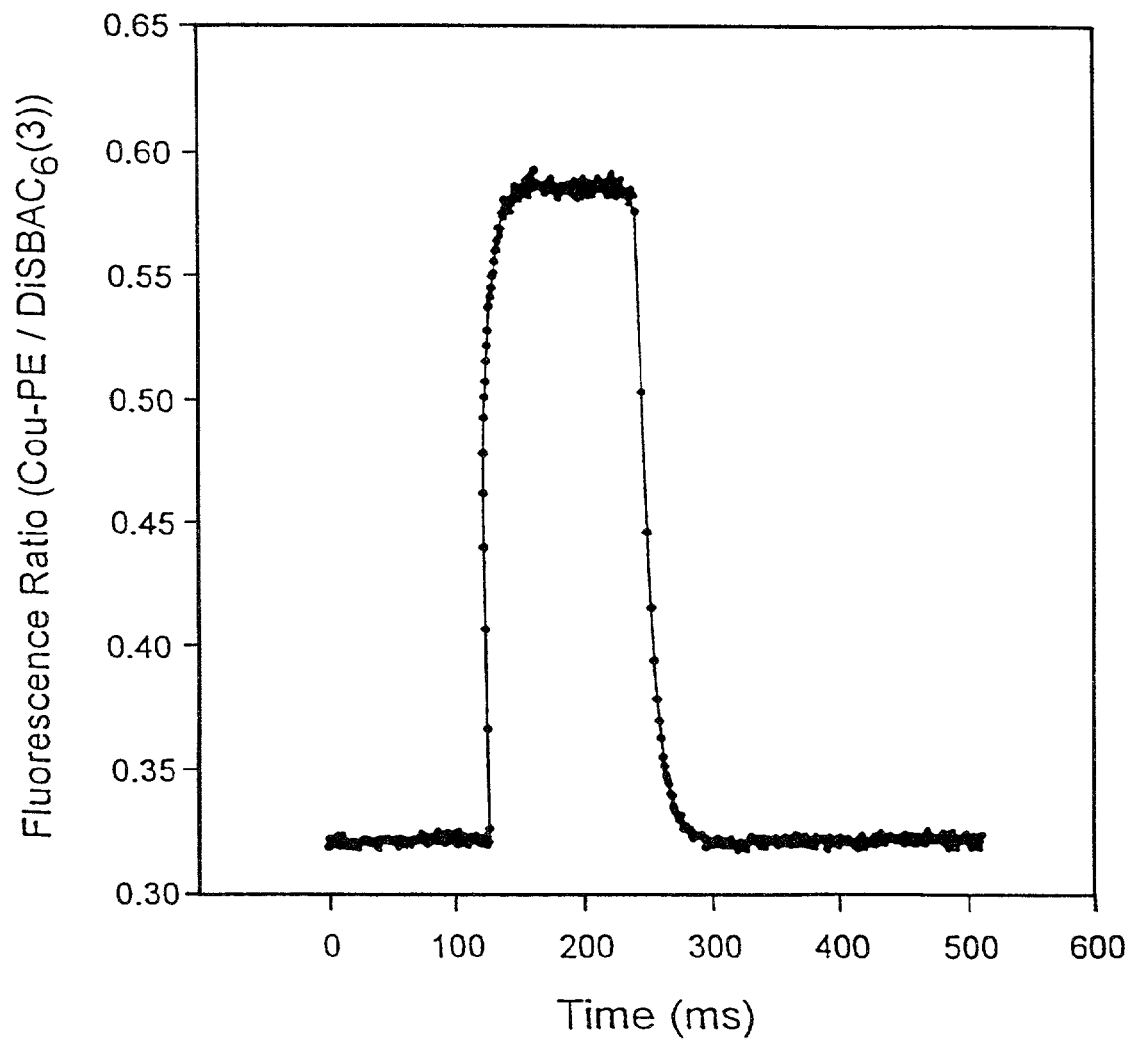
FIG. 17 shows FRET between Cou-PE, a conjugate of a 6-chloro-7-hydroxycoumarin to dimyristoylphosphatidylethanolamine, as FRET donor, to a bis-(1,3-dihexyl-2-thiobarbiturate)-trimethineoxonol in an astrocytoma cell.
Figure 18:
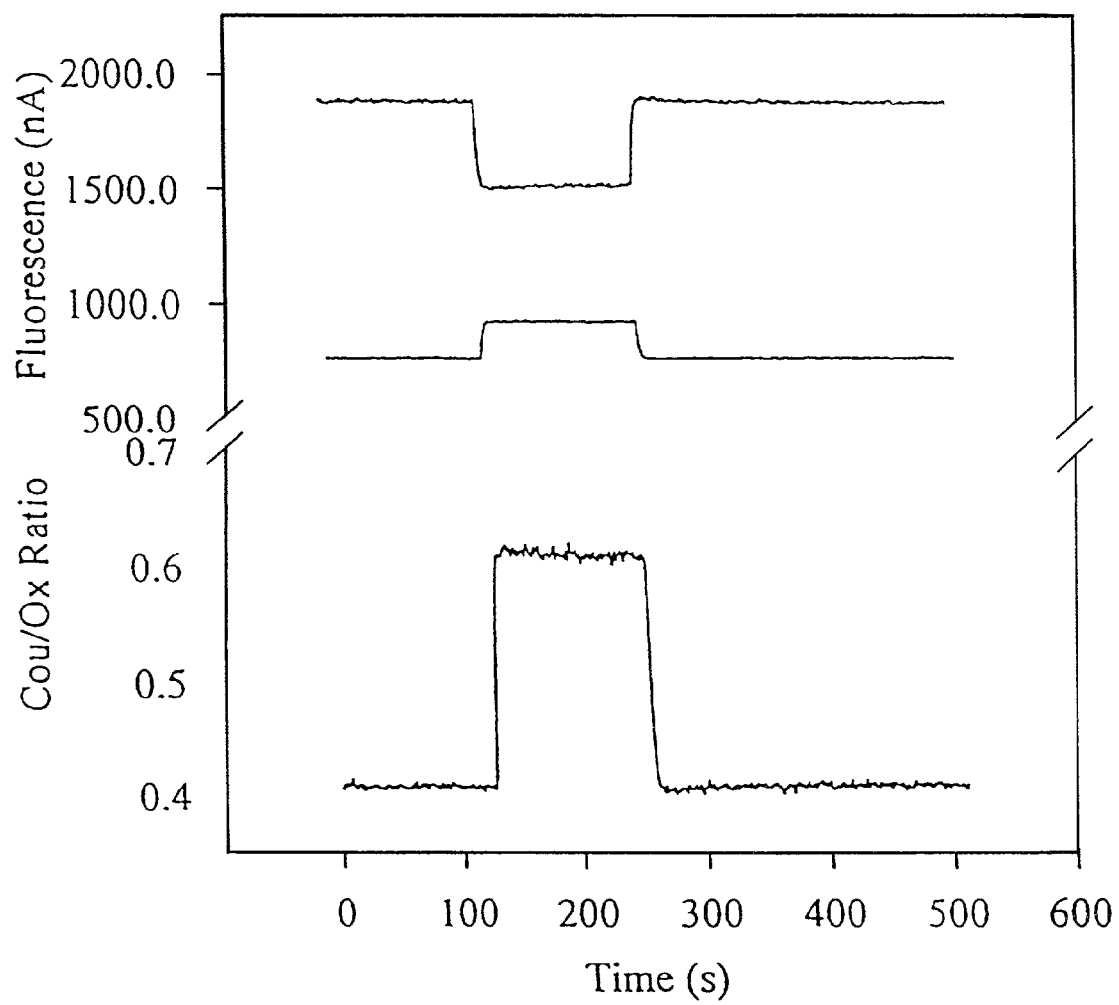
FIG. 18 shows FRET between DMPE-glycine-coumarin (Cou-PE) as FRET donor to a bis-(1,3-dihexyl-2-thiobarbiturate)-trimethineoxonol in L-cells.
Figure 19:
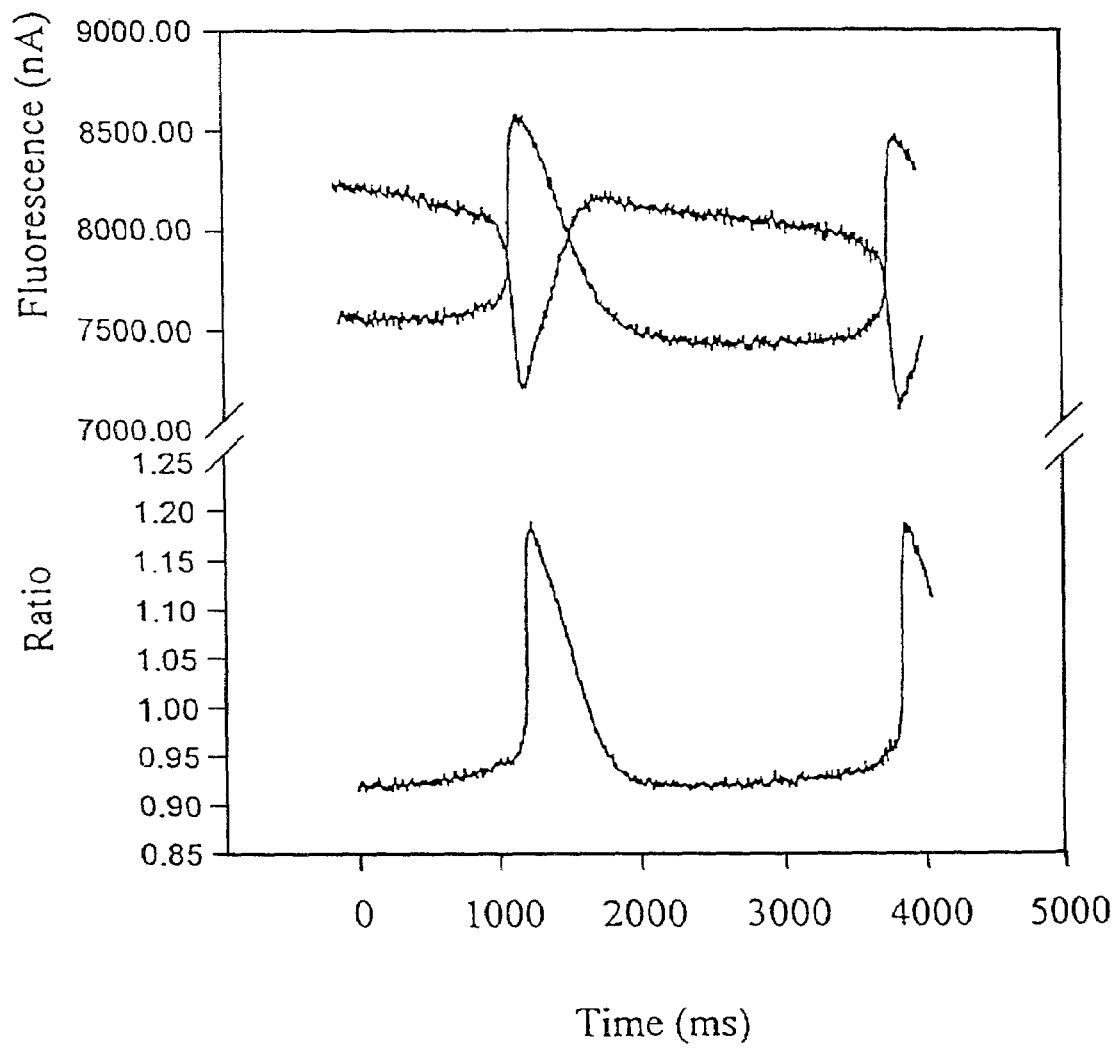
FIG. 19 shows FRET between DMPE-glycine-coumarin (Cou-PE) as FRET donor to a bis-(1,3-dihexyl-2-thiobarbiturate)-trimethineoxonol in cardiomyocytes measured by ratio output.

Measurement of Membrane Potential with Oxonol Dyes as Fret Acceptors and Fluorescent Lipid Fret Donors A. Trimethine Oxonols A 6-chloro-7-hydroxycoumarin conjugated to dimyristoylphosphatidylethanolamine (DMPE) via a glycine linker, Cou-PE, has been prepared and found to function as an excellent voltage-sensitive FRET donor to bis-(1,3-dialkyl-2-thiobarbiturate)-trimethineoxonols. This new FRET pair has given an 80% ratio change for a 100 mV depolarization in an astrocytoma cell, which is the largest voltage-sensitive optical signal observed in a cell, FIG. 17. The voltage sensitivity of this FRET pair is consistently 2–3 times better than Fl-WGA/trimethineoxonol in a variety of cell types. In L-cells, ratio values between 25–50% are found, with equal percent changes found in both channels, FIG. 18. In neonatal cardiomyocytes, 5–30% fluorescence ratio changes were observed for spontaneously generated action potentials. The largest signals are almost 4 times larger than those possible with Fl-WGA/trimethineoxonol. An example of such a large change from a single cluster of heart cells is given in FIG. 19. The benefits of a ratio output are evident in the figure. The individual wavelengths, at the top of the figure, show a decreasing baseline that is due to fluorophore bleaching. The ratio data shown on the bottom of the figure compensates for the loss of intensity in both channels and results in a flat baseline. Furthermore, motion artificially causes broadening of the individual wavelength responses. The ratio data reduces these artifacts and results in a sharper signal that more closely represents the actual voltage changes. The greater sensitivity for this new FRET pair is most likely due to a combination of factors. Moving the donor closer to the membrane surface and decreasing the Forster transfer distance, $R_O$, may result in increased FRET discrimination between the mobile ions on the same and opposite sides of the membrane. Also, the increased spectral separation facilitates collection of the donor and acceptor emission and reduces signal loss due to crosstalk.

B. Pentamethine Oxonols

Bis-(1,3-dialkyl-2-thiobarbiturate)-pentamethineoxonols have been prepared by condensing 1,3 substituted thiobarbituric acids with glutacondialdehyde dianil monohydrochloride, also known as N-[5-(phenylamino)-2,4-pentadienylidene]benzenamine monohydrochloride. The pentamethine oxonols absorb at 638 nm ($\epsilon$=225,000 $M^{-1}$ $cm^{-1}$) and fluoresce maximally at 663 nm in ethanol. The absorbance and emission are shifted 100 nm to longer wavelengths, compared to the trimethine oxonols. This shift is consistent with other polymethine dyes, such as cyanines, where addition of 2 additional methine units results in 100 nm wavelengths shifts to the red.

The pentamethines can be loaded into cells in culture in the same manner as the trimethine oxonol. The butyl compound, $DiSBAC_4(5)$, can be loaded in Hanks' Balanced Salt Solution, while the hexyl compound, $DiSBAC_6(5)$, requires addition of beta-cyclodextrin to mask the hexyl side chains and solubilize the hydrophobic oxonol.

Voltage-sensitive FRET from various plasma membrane-bound fluorescent donors to the pentamethine oxonols have been demonstrated in single cells. Fl-WGA has been shown to undergo FRET with the pentamethine and give ratio changes comparable to those observed for the trimethine oxonol. In astrocytoma cells, ratio changes of 15–30% were recorded for a 100 mV depolarization step from −70 mV. Apparently, the decrease in FRET due to the reduced overlap integral, J, on moving the oxonol absorbance 100 nm longer is compensated by increased selectivity of FRET to the extracellular face of the membrane relative to the intracellular one and/or decreased spectral overlap.

Figure 20:
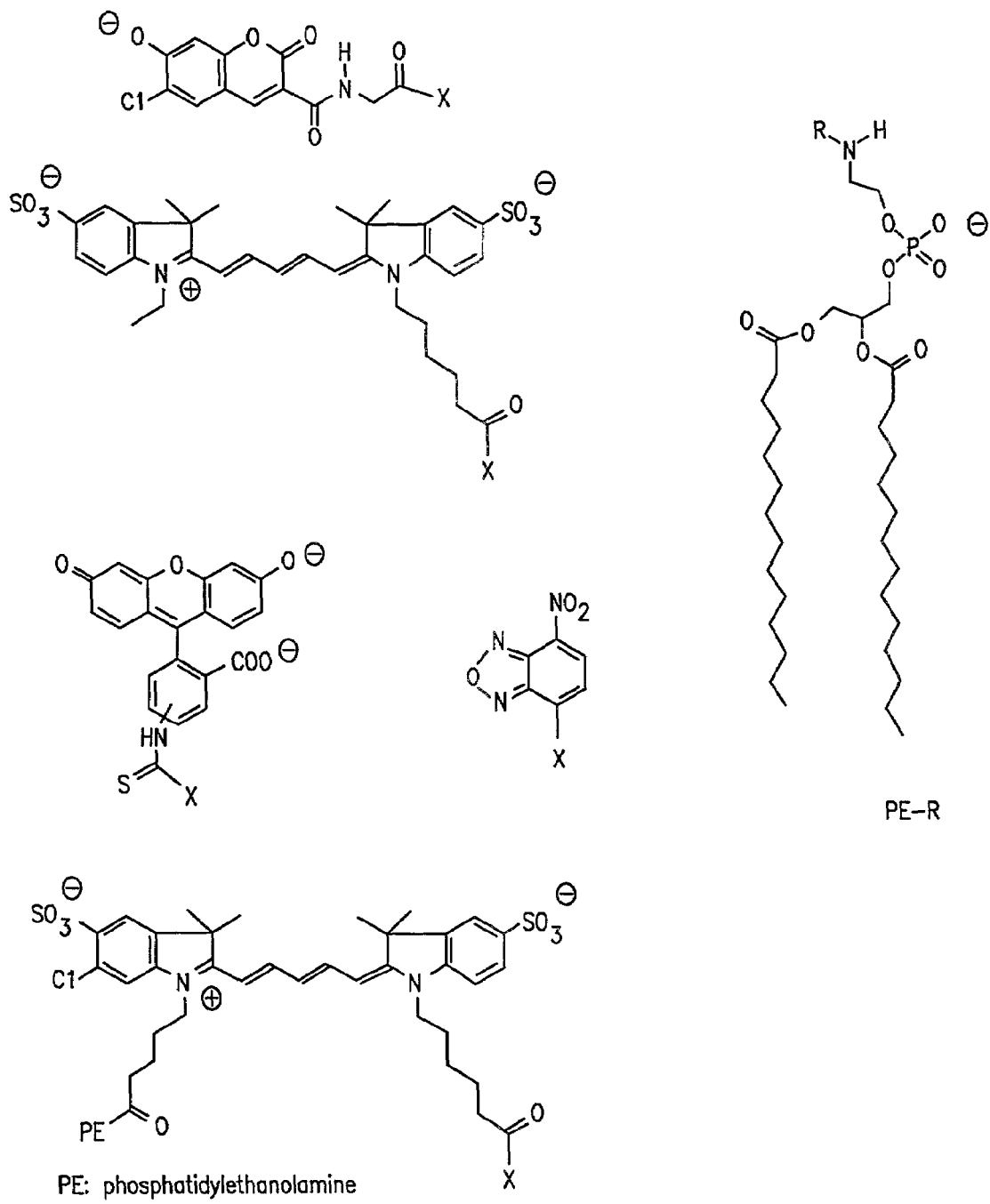
FIG. 20 shows representative fluorescent phosphatidylethanolamine conjugates that function as FRET donors to the oxonols. The structures on the left depict representative fluorophores and X denotes the site of attachment of the phosphatidylethanolamine (PE). The structure (PE-R) on the right shows a phosphatidylethanolamine where R denotes a fluorophore attached to the amine of the ethanol amine.
Figure 21:
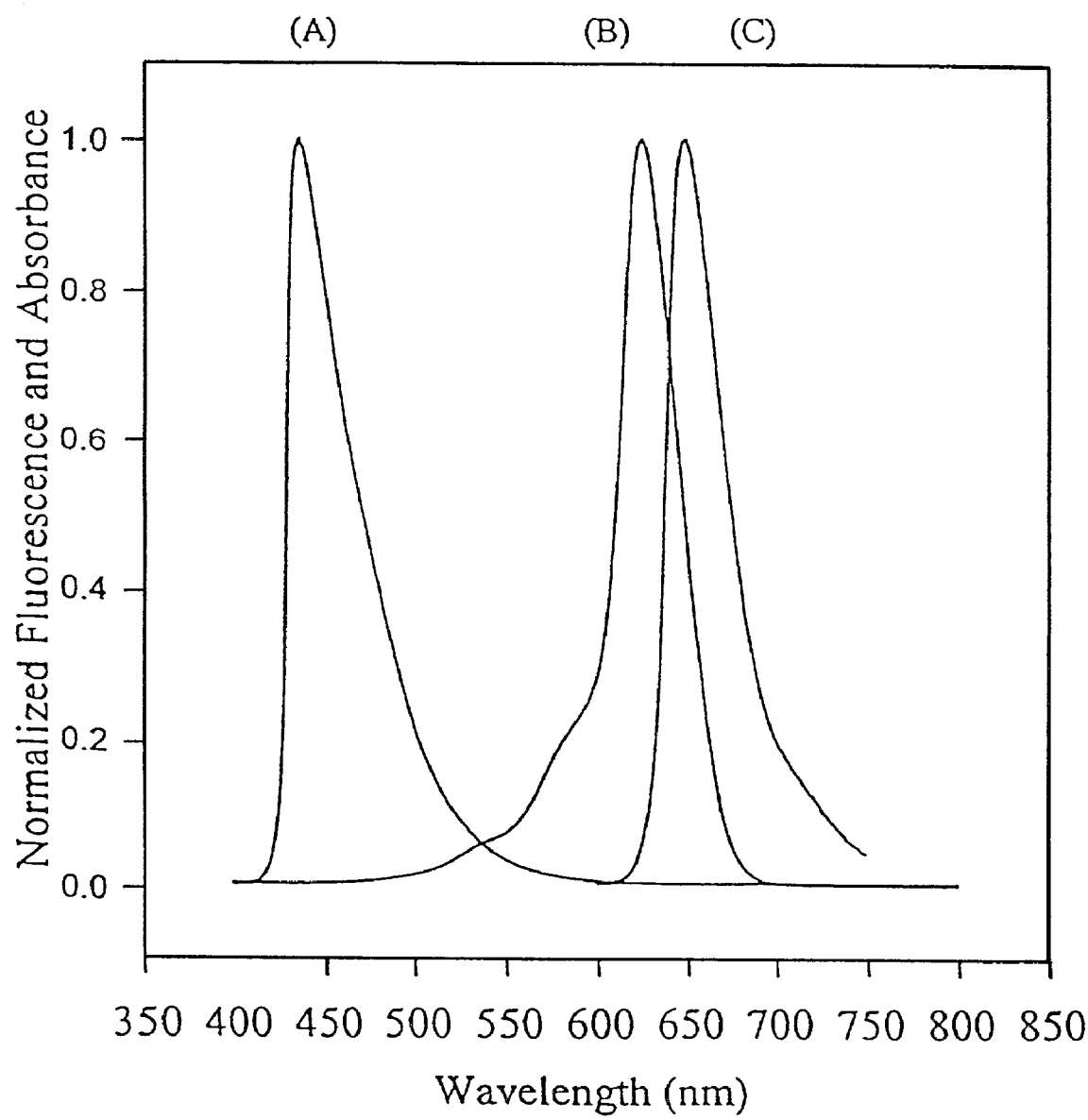
FIG. 21 shows (A) emission spectrum of the Cou-PE; (B) the excitation spectrum of DiSBA-$C_6$-(5); and (C) the emission spectrum of DiSBA-$C_6$-(5).

Fluorescent phosphatidylethanolamine conjugates have also been found to function as FRET donors to the pentamethine oxonol. The structures of PE conjugates tested are shown in FIG. 20. NBD-PE/pentamethineoxonol pair has given 1–10% ratio changes per 100 mV. Cou-PE/pentamethineoxonol has given 15–30% ratio changes in voltage clamped astrocytomas for 100 mV depolarization. This pait is remarkable because the Cou-PE emission and $DiSBAC_6(5)$ absorbance maxima are separated by 213 nm and there is hardly any visible overlap, FIG. 21. The large extinction at long wavelengths of the pentamethine enable FRET between the coumarin and the pentamethine oxonol. The Ro for this pair has been calculated to be 37 Å, using a quantum yield value of 1.0 for the Cou-PE.

Figure 22:
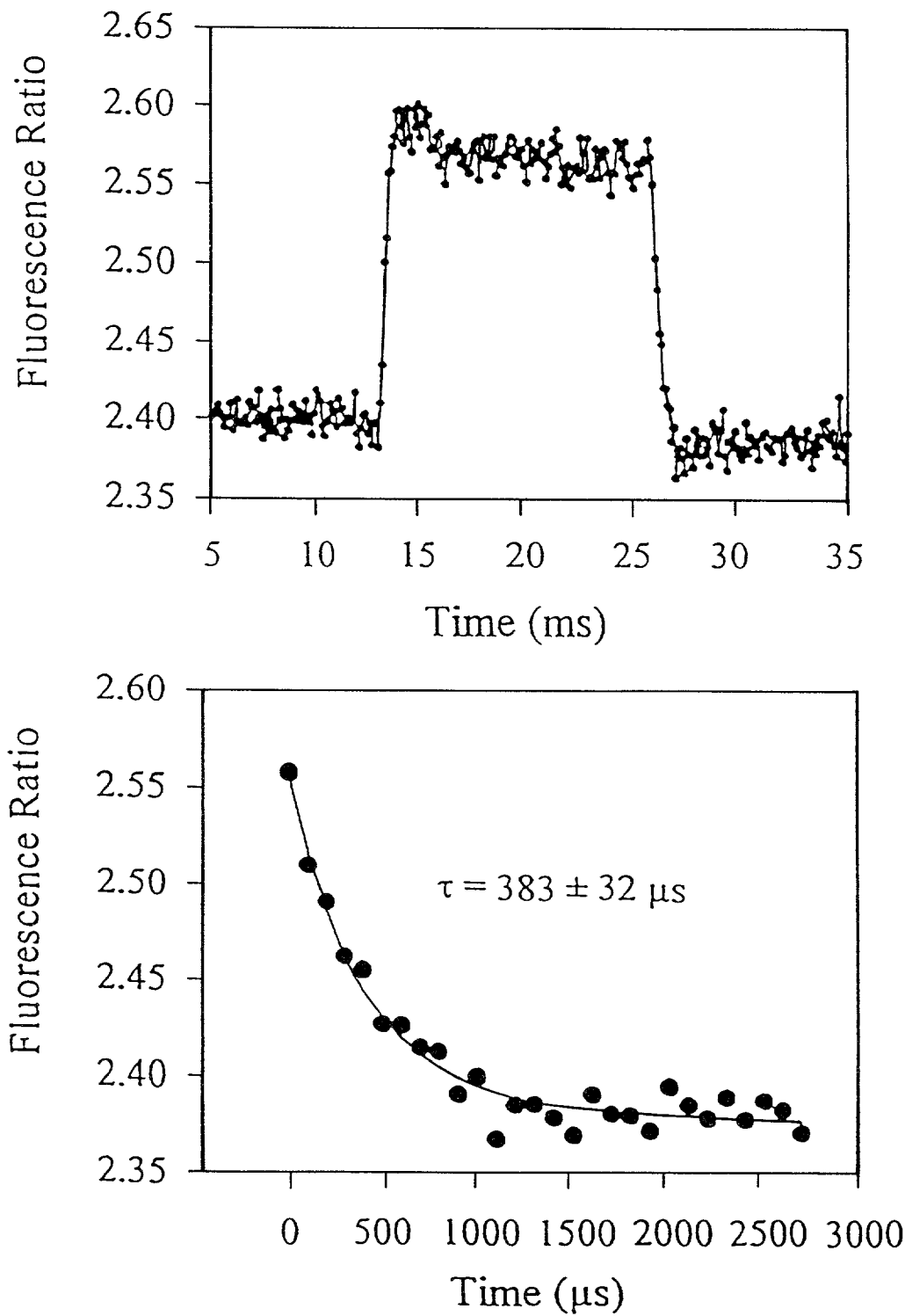
FIG. 22 shows the speed of DiSBA-$C_6$(5) translocation in response to a 100 mV depolarization step, using FRET from asymmetrically labeled Cou-PE.
Figure 23:
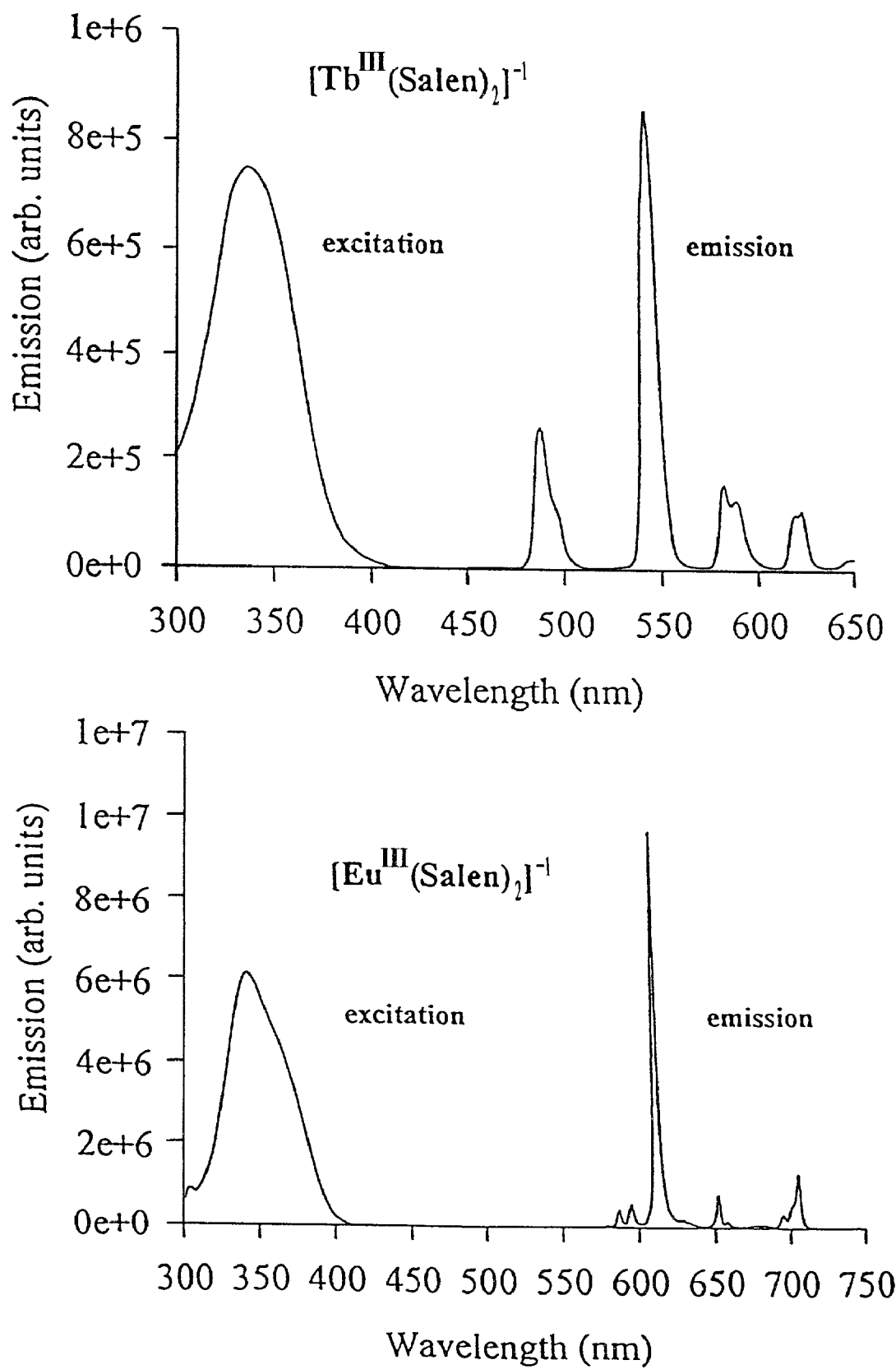
FIG. 23 shows the spectra of [Tb(Salen)$_2$]$^{-1}$ (top) and [Eu(Salen)$^2$]$^{-1}$ (bottom), both as piperidinium salts dissolved in acetonitrile.

The membrane translocation rates for the pentamethines are 5–8 times faster than the trimethine analogues. DiSBAC$_4$(5) displacement currents in voltage-clamped astrocytoma cells showed that butyl pentamethine oxonol jumps across the plasma membrane with a time constant of ~2 ms in response to voltage steps of +20–120 mV. The trimethine analogue translocates ~18 ms under identical conditions. The displacement currents of $DiSBAC_6(5)$ decay very rapidly and are difficult to separate from the cell capacitance. As a result of the large voltage-dependent signal from the Cou-PE/$DiSBAC_6(5)$ pair, it was possible to optically measure the speed of voltage response of $DiSBAC_6(5)$. The time constant for $DiSBAC_6(5)$ translocation was measured optically at 0.383±0.032 ms in response to a 100 mV depolarization step, using FRET from asymmetrically labeled Cou-PE. The ratio data and the exponential response are shown in FIG. 22. The enhanced translocation rates result from the greater charge delocalization and slightly more hydrophobicity of the pentamethine oxonols. The rapid voltage response of $DiSBAC_6(5)$ is the fastest known for a permeant, highly fluorescent molecule. The submillisecond response is fast enough to accurately register action potentials of single neurons.

Example VI

Measurement of Membrane Potential with Oxonol Dyes as Fret Donors

The direction of energy transfer can be reversed using TR-WGA instead of FL-WGA. DiSBA-C$_6$-(3) functions as a FRET donor to TR-WGA in L-M(TK$^-$) cells with the same response time as FL-WGA/DiSBA-C$_6$-(3). The spectral overlap of this FRET pair is shown in FIG. 2. The signal change, however, is only one half that for FL-WGA/DiSBA-C$_6$-(3).

DiSBAC$_6$(3) has been successfully used as a FRET donor to Cy5 labeled PE, in B104 neuroblastoma cells. The ratio changes of 5–15%/100 mV are the largest observed with the mobile ion being the donor.

Example VII

Measurement of Membrane Potentials in Different Cell Types

Figure 8:
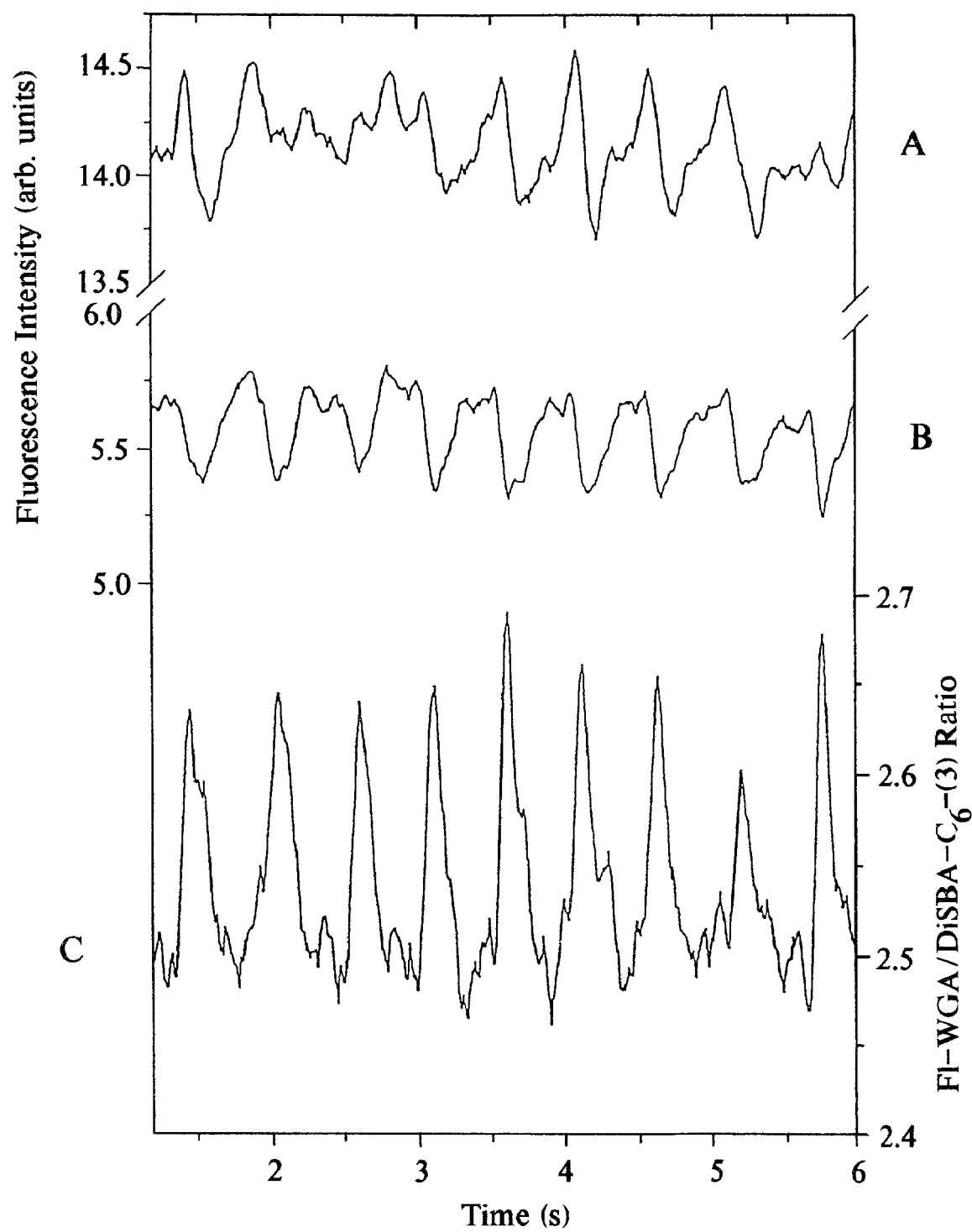
FIG. 8 illustrates a single sweep trace of fluorescence ratio changes from the FL-WGA/DiSBA-$C_4$-(3) pair in beating neonatal cardiac myocytes, with the top trace (A) showing the FL-WGA channel, (B) the longer wavelength oxonol channel and (C) the FL-WGA/oxonol ratio, in which motion artifacts are significantly reduced.
Figure 9:
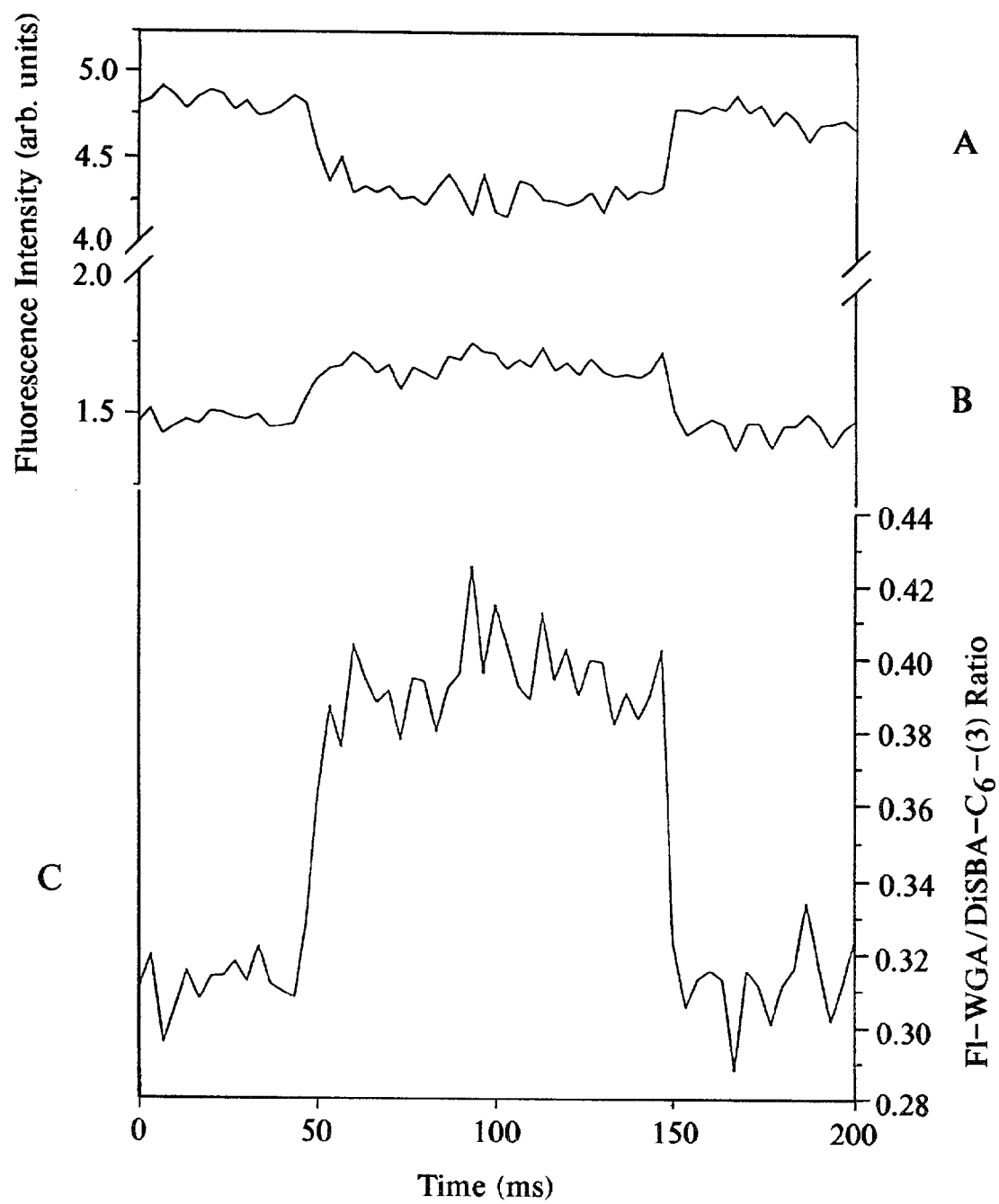
FIG. 9 illustrates the fluorescence changes of the FL-WGAl/DiSBA-$C_6$-(3) pair in a voltage clamped astrocytoma cell, the top trace (A) being the DiSBA-$C_6$-(3) emission, (B) the FL-WGA fluorescence signal and (C) the FL-WGA/oxonol ratio.

The FL-WGA/DiSBA-C$_6$-(3) system was tested in a variety of cell lines. In neonatal cardiac myocytes, the two fluorophores could be loaded without affecting the spontaneous beating. Therefore, the added capacitance from the oxonol displacement current did not prevent generation of action potentials. The periodic 90 mV action potentials [Conforti, L., Tohse, N., and Sperelakis, N. 1991. Influence of sympathetic innervation on the membrane electrical properties of neonatal rat cardiomyocytes in culture. *J. Devel. Physiol.* 15:237–246] could be observed in a single sweep, FIG. 8C. The ratio change without subtraction of any background fluorescence was 4–8%. Motion artifacts were observed in the single wavelength data. In FIGS. 8A and B, large slow changes in the detected light were observed in both channels. Satisfyingly, these effects were essentially eliminated in the ratio data. The data were acquired at 100 Hz and 10 M of isoproterenol was added to the bath solution. The voltage dependent fluorescence changes are faster than the mechanically based artifacts, as expected [Hill, B. C. and Courtney, K. R. 1982. Voltage-sensitive dyes discerning contraction and electrical signals in myocardium. *Biophys. J.* 40:255–257]. Some cells, loaded with oxonol at 2.3 M, did stop beating after about 7 seconds of continuous exposure to the xenon arc illumination. At 0.6 M loading, the phototoxicity and unfortunately the signal were reduced. In differentiated B 104 neuroblastoma cells an 8% ratio increase was recorded, without any background subtraction, for a 120 mV depolarization. The inward sodium currents did not deteriorate from phototoxic effects during experiments with excitation exposures totaling 10–20 s. FL-WGA/DiSBA-$C_6$-(3) labeled 1321N astrocytoma cells showed oxonol and FL-WGA fluorescence almost exclusively on the plasma membrane. Ratio changes of 22–34% for 100 mV were observed in photometry experiments such as FIG. 9. After a 50 ms delay, the membrane potential was depolarized 100 mV from −70 mV for 100 ms. The traces are the average of 4 sweeps acquired at 300 Hz, with no smoothing. The time constant for the fluorescence changes is less than 3.3 ms consistent with the displacement currents, such as those in FIG. 3. A small background signal was subtracted from the starting signal, <5% for the oxonol channel and <15% for the fluorescein channel. The fluorescence intensities in the fluorescein and oxonol channels increased ~17% and decreased ~16% respectively for 100 mV depolarization. In these cells, unlike the L-M(TK−), the crosstalk between emission channels was decreased and larger changes occurred in the fluorescein signal. These signal changes are the largest millisecond membrane potential dependent ratio changes observed in single cells. Previous investigations have shown that 4-ANEPPS gives a 9% /100 mV excitation ratio change [Montana, V., Farkas, D. L., and Loew, L. M. 1989. Dual-wavelength ratiometric fluorescence measurements of membrane potential. *Biochemistry* 28:4536–4539]. In addition, FL-WGA/DiSBA-$C_6$-(3) fluorescence changes in each emission channel are comparable to the largest reported changes, for example, the 21% /100 mV change in a neuroblastoma using RH-421 [Grinvald, A., Fine, A., Farber, I. C., and Hildesheim, R. 1983. Fluorescence monitoring of electrical responses from small neurons and their processes. *Biophys. J.* 42:195–198]. The large signals from FL-WGA/DiSBA-$C_6$-(3) made it possible to record ratio images of membrane potential changes in voltage C. clamped L-M(TK−) and astrocytoma cells using a high speed confocal microscope.

The astrocytoma cells gave a 10–20% ratio increase that was localized to the plasma membrane for a 120 mV depolarization.

Example VIII

Synthesis of Fluorescent Tetraaryl Borates

With reference to FIG. 10, in a 25 mL flame dried two neck flask 0.788 g (580 L, 2.2 mmol) of compound I was dissolved in 6 mL of dry hexane under argon. After cooling the flask to −70 C, 1.46 mL of a 1.5 M n-butyllithium solution (2.2 mmol) was added via syringe. In a separate flask 0.60 dry borane II was dissolved in a deoxygenated mixture of 6 mL hexane and 1.5 mL of freshly distilled THF. The borane solution was then added via syringe to the lithium reagent. A solid immediately precipitated. After 30 min the cold bath was removed and the reaction was allowed to slowly heat up. Three hours later the solvent was decanted off and the solid rinsed with more hexane. The solid was dissolved in acetonitrile and water and then poured into a separatory funnel. The aqueous layer was again washed with hexane and then extracted with ethyl acetate. Half of the extract was concentrated yielding 124.9 mg (170.5 mol) of the desired product. This product was then mixed with 97 mg of tetrabutylammonium fluoride in acetonitrile for 15 min at room temperature. After workup 129.1 mg of compound III as the tetrabutylammonium salt was recovered (93%). $^1$HNMR ($d_6$ acetone) 7.61 (br d, 2H, $CF_3$-phenyl group), 7.43 (cm, ~3H, $CF_3$-phenyl group), 6.90–7.26 (cm, ~7H, $CF_3$-phenyl group), 3.43 (cm, 8H, NC$\underline{H}_2$C$H_2$ C$H_2$ $CH_3$), 1.81 (cm, ~8H, NC$H_2$C$\underline{H}_2$C$H_2$C$H_3$), 1.42 (cm, ~8H, NC$H_2$C$H_2$ C$\underline{H}_2$ $CH_3$), 0.93 (t, J=7.1 Hz, NC$H_2$C$H_2$ $CH_2$C$\underline{H}_3$).

With reference to FIG. 10, for synthesis of compound IV, in a 5 mL round bottom flask 14 mg (17.2 umol) of compound III, 7 mg (25.8 umol) of bromomethylbimane, 27.3 mg (172 umol) of potassium carbonate, and 5 mg (18.9 umol) of 18-crown-6 were mixed in 0.6 mL of dry acetonitrile. The mixture was heated at 70 C 1.5 h. After cooling, the reaction mixture was dissolved in ethyl acetate and washed 3× with water. The organic residue was purified by flash chromatography eluting with toluene/acetone (2:1). The major band was collected yielding 12.1 mg (70%) of pure product IV tetrabutyl ammonium salt. $^1$HNMR (d6 acetone) 7.58 (br d, 2H, $CF_3$-phenyl group), 7.4–7.5 (cm, 2H, $CF_3$-phenyl group), 7.0–7.3 (cm, 1OH, $CF_3$-phenyl group), 5.29 (d, J=1.6 Hz, 2H, $CH_2$), 3.46 (cm, 8H, NC$\underline{H}_2$C$H_2$ $CH_2$ $CH_3$), 2.56 (d, J=0.7 Hz, 3H, bimane methyl), 1.84 (cm, ~8H, NC$H_2$C$\underline{H}_2$ $CH_2$ $CH_3$), 1.79 (d, J=0.8 Hz, 3H, bimane methyl), 1.76 (s, 3H, bimane methyl), 1.44 (cm, ~8H, NC$H_2$C$H_2$ C$\underline{H}_2$ $CH_3$), 0.98 (t, J=7.2 Hz, NC$H_2$C$H_2$C$H_2$ C$\underline{H}_3$); $f$=0.73 in dioxane based on quinine sulfate in 0.1 N $H_2SO_4$ $f$=0.55.

Example IX

Synthesis of Asymmetric Oxonols with a Linker Group (A) This example illustrates the synthesis of asymmetric oxonols containing a built-in linker group. With reference to FIG. 11, for synthesis of compound V, 4.35 g (21.7 mmol) of 1,12-diaminododecane was dissolved in 40 mL of dry $CH_2Cl_2$. Via syringe, 2.62 mL (2.17 mmol) of butyl isothiocyanate was added to the reaction flask. A white solid had precipitated after 15 minutes. One hour after the addition, the reaction mixture was filtered. The filtrate was then evaporated leaving a white solid. The solid was redissolved in 45 mL of dry $CH_2Cl_2$ and mixed with 2.44 mL of N,N-diisopropylethylamine (DIEA) and 3.9 g (17.9 mmol) of di-tert-butyl dicarbonate. After reacting for 1 hour, the mixture was poured into a separatory funnel and washed with 5% sodium bicarbonate. A solid came out of solution and was filtered away (<100 mg). The organic solution was then washed with water and a saturated brine solution. The organic layer was then dried with $MgSO_4$ and filtered. The filtrate was evaporated leaving a white solid, which was recrystallized in isopropyl ether yielding 4.30 g (10.3 mmol) of pure compound V (48% overall). $^1$HNMR ($CDCl_3$) 5.73 (br s, 2H, thioamide), 4.50 (br s, 1H, carbamate), 3.40 (br s, 4H, NC$\underline{H}_2$), 3.10 (q, J=7.2 Hz, ~3 H, C$\underline{H}_2$ next to carbamate), 1.44 (s, 9H, t-butyl), 1.2–1.7 (cm, bulk $CH_2$ s), 0.94 (t, J=7.2 Hz, n-butyl methyl).

For preparing compound VI, 441 mg (19.2 mmol) of sodium was dissolved in 5 mL of dry ethanol under argon. When almost all of the sodium was dissolved, 2.92 mL (3.1 g, 19.2 mmol) of diethyl malonate was added to the ethoxide solution. Some solid precipitated out of solution. 4.0 g (9.6 mmol) of compound V was added and the mixture was refluxed under argon at 100 C for 70 hours. After cooling, the reaction mixture was filtered and washed with ethanol. Water was added to the filtrate and a white solid precipitated out of solution. The solid (779 mg, mostly of unreacted starting material) was filtered away. The filtrate was then acidified to pH ~2 and then extracted into ethyl acetate. The organic layer was then dried with MgSO$_4$ and filtered. After removing the solvent, 1.6 g (3.3 mmol) of a yellow oil was recovered (34%). $^1$HNMR (CDCl$_3$) 4.22 (cm, 4H, NCH$_2$ next to barbiturate). 3.63 (s, 2H, ring CH$_2$), 2.99 (cm, 2H, CH$_2$ next to carbamate), 1.53 (cm, 4H, NCH$_2$CH$_2$), 1.34 (s, 9H, t-butyl), 1.1–1.3 (cm, bulk CH$_2$ s), 0.85 (t, J=7.4 Hz, n-butyl methyl).

To prepare compound VII, 1 mL of trifluoroacetic acid (TFA) was added with stirring to 200 mg (0.41 mmol) of compound VII dissolved in 3 mL of CH$_2$Cl$_2$. After 1.25 hours, all the solvent was removed under reduced pressure. One equivalent each of N-[5-(phenylamino)-2,4-pentadienylidene]aniline monohydrochloride and 1,3-di-n-butylthiobarbiturate was added and all three components dissolved in 1 mL pyridine and left overnight. The product was purified from the other pentamethine oxonols by flash chromatography. The nonpolar products were eluted with CHCl3/CH$_3$OH (9:1). The pure product containing the linker eluted with CHCl$_3$/CH$_3$OH (1:1). The product was bound very tightly to the silica gel and only 10 mg of product was recovered. $^1$HNMR (CDCl$_3$/CD$_3$OD) 7.5–7.8 (cm, 4H, vinyl methines), 7.35 (t, J=~14 Hz, 1H, central methine), 4.34 (br t, ~10H NCH$_2$ next to barbiturate), 2.72 (cm, ~3H, CH$_2$ next to amine), 1.4–1.7 (br cm, ~12H, NCH$_2$CH2), 1.0–1.4 (cm, ~40H, bulk CH$_2$ s), 0.81 (t, J=7.3 Hz, 9H, n-butyl methyl).

(B) This particular example is with reference to FIGS. 15 and 16.

N-butyl-N-5-pentanol thiourea (6): 5-amino-1-pentanol (1.416 mL, 13 mmol) was dissolved in 7 mL of CH$_2$Cl$_2$. Under argon, butylisothiocynate (1.570 mL, 13 mmol) was added via syringe. After 2.5 h, the solvent was removed under vacuum leaving an oil. Under high vacuum, the oil was freeze dried 2× with liquid nitrogen and left under reduced pressure over night. The next morning 2.615 g of pure solid product was collected (12 mmol, 92%). $^1$H NMR (CDCl$_3$): d 5.90 (br s, 2H, NH), 3.66 (t, J=6.2 Hz, 2H, RCH$_2$OH), 3.42 (br m, 4H, NHCH$_2$R), 1.80 (br s, 1H, OH), 1.3–1.7 (unres. cm's, 10H, bulk methylenes), 0.94 (t, J=7.2 Hz, 3H, methyl). $^{13}$C NMR (CDCl$_3$): d 181.5 (thiocarbonyl), 62.2 (RCH$_2$OH), 44.2 (NHCH$_2$R), 44.1 (NHCH$_2$R), 31.9 (CH$_2$), 31.0 (CH$_2$), 28.6 (CH$_2$), 23.0 (CH$_2$), 19.9 (CH$_2$), 13.6 (CH$_3$).

1-butyl,3-(5-pentanol) thiobarbiturate (7): In dry EtOH, 345 mg (15 mmol) of Na was dissolved. After almost all of the Na had dissolved, diethylmalonate (2.278 mL, 15 mmol) was added under argon. The mixture was then heated to 60° C. to dissolve the precipitated sodium malonate. The heat was then removed and N-butyl-N-5-pentanol thiourea (6) (1.310 g, 6 mmol) was added. The reaction mixture was refluxed a 100° C. for 3.5 days. After cooling, the reaction mixture was filtered and washed with EtOH. An approximately equal volume of H$_2$O was added to the filtrate and acidified to pH 1–2 with conc. HCL. The aqueous solution was extracted 3× with 1:1 EtOAc/hexanes. The combined extracts were dried with MgSO$_4$, filtered, and concentrated leaving an oil. TLC EtOAc/MeOH (4:1) showed that in addition to the major barbiturate product there were two nonpolar impurities. Flash silica gel chromatography afforded some purification (4×17 cm), eluting with EtOAc/MeOH (4:1). The material was still an oil and a second column was done eluting with CHCl$_3$/MeOH/AA (90:8:2). Despite being an oil, 0.726 g (2.54 mmol, 42%) of pure product was recovered. $^1$H NMR (CDCl$_3$): d 4.31 (cm, 4H, NCH$_2$R), 3.71 (br s, 2H, ring methylene), 3.63 (t, J=6.3 Hz, 2H, RCH$_2$OH), 2.75 (br s, 1H, OH), 1.5–1.8 (cm, 6H, bulk methylenes), 1.2–1.5 (cm, 4H, bulk methylenes), 0.94 (t, J=7.2 Hz, 3H, methyl).

1-butyl,3-(5-bromopentane) thiobarbiturate (8): (7) (98 mg, 343 umol) was dissolve in 600 uL dry CH$_2$Cl$_2$ and mixed with carbon tetrabromide (142 mg, 429 umol). The solution was cooled on ice and triphenylphosphine (135 mg, 515 umol) was added. The solution bubbled and turned yellow immediately. After 30 min. the solvent was removed and hexane was added to the solid residue. The mixture was allowed to stir overnight. TLC showed only 1 barbiturate in hexane solution along with triphenylphospine oxide. The impurity was removed by flash silica gel chromatography (2.5×22 cm) packed in EtOAc/MeOH (98:2). The nonpolar impurity was eluted off the column using the packing solvent followed by EtOAc/MeOH (90:10). The desired product was eluted with CHCl$_3$/MeOH/AA (93:5:2), yielding 40 mg (115 umol, 34%). $^1$H NMR (CDCl$_3$): d 4.33 (cm, 4H, NCH$_2$R), 3.72 (s, 2H, ring methylene), 3.42 (t, J=6.7 Hz, 2H, RCH$_2$Br), 1.91 (cm, 2H, methylene), 1.66 (cm, 4H, methylenes), 1.52 (cm, 2H, methylene) 0.95 (t, J=7.2 Hz, 3H, methyl).

1,3-di-butyl-5-(3-phenylamino propendienyl) thiobarbiturate (10): Malonaldehyde bis(phenylimine) (500 mg, 1.69 mmol) was dissolved in 20 mL of dry DMF. Separately, 1,3 di-butyl thiobarbiturate (430 mg, 1.76 mmol) was dissolved in 5 mL dry pyridine and placed in a 10 mL dropping funnel. The thiobarbiturate solution was slowly added over 5 min and the reaction was left stirring for 5 h. About 20 mL of water was added to the mixture and a yellow solid precipitated out of solution. The solid was filtered and dried yielding 575 mg (1.5 mmol, 89%). Minor impurities, including oxonol, were removed by flash silica gel chromatography (3×15 cm) eluting with EtOAc/hexanes (1:1). Some material precipitated on the column. Nevertheless after drying, 390 mg of pure product was recovered (1 mmol, 59%). 1H NMR (CDCl$_3$/MeOH): d 8.10 (d, J=3.0 Hz, 1H), 8.04 (s, 1H), 7.3–7.5 (cm, 3H), 7.1–7.25 (cm, 3H ), 4.40 (cm, 4H, NCH$_2$R), 1.65 (cm, 4H, NCH$_2$CH$_2$R), 1.36 (cm, 4H, NCH$_2$CH$_2$CH$_2$CH$_3$), 0.90 (t, J=7.3 Hz, 6H, methyls).

1-(1,3-dibutyl thiobarbiturate)-3-(1-butyl,3-(5-hydroxypentyl)thiobarbiturate) trimethineoxonol triethylammonium salt (11): Compound (7) (85 mg, 297 umol) was mixed with (10) (114 mg, 297 umol) in 1.2 mL dry pyridine and left stirring for 17 h. TLC EtOAc/MeOH showed that there was 3 major oxonol products. Conc. HCL was added to 80% of the reaction mixture which caused a solid to precipitate out of solution. The solid was filtered and washed with water. After drying 220 mg of red solid was recovered. 96 mg of this solid was mixed with 1–2 mL EtOAc and filtered. The remaining solid was dissolved in CHCl$_3$/MeOH (95:5) and loaded on to a 19×2.5 cm silica gel column. Eluting with the same solvent, the most nonpolar oxonol was eluted off the column. The solvent was then changed to CHCl$_3$/MeOH/Et$_3$N (90:8:2) to elute the middle band which was shown by NMR to be the desired product. After concentrating and drying, 18.5 mg (28 umol, 27%) of the pure product was recovered. $^1$H NMR (CDCl$_3$): d 8.60 (t, J=13.9 Hz, 1H, central methine), 8.14 (dd, J$_1$=13.8 Hz, J2=2,2 Hz, 2H, methines), 4.45 (cm, 8H, NCH$_2$R), 3.66 (t, J=6.3 Hz, 2H, RCH$_2$OH), 3.20 (q, J=7.3 Hz, 6H, triethylammonium), 1.5–1.8 (cm, 8H, NCH$_2$CH$_2$R), 1.2–1.5 (cm, 10H, bulk methylenes), 1.35 (t, J=7.3 Hz, 9H, triethylammonium), 0.95 (t, J=7.2 Hz, 9H, terminal methyl). MS.

1-(1,3-dibutyl thiobarbiturate)-3-(1-butyl-3-(5-tosyloxypentyl)thiobarbiturate) trimethineoxonol (12): In 4 mL pyridine, (11) (86.1 mg, 131 umol) was mixed with tosyl chloride (333 mg, 1.75 mmol). The reaction mixture was stirred for 3.5 h before the solvent was removed under vacuum. The residue was dissolved in EtOAc and washed with 1 M HCL, followed by sat. brine 2×. TLC EtOAc/MeOH (9:1) showed that most of the starting material was converted to a more non polar product. However, a polar oxonol impurity was evident and the material had to be further purified by flash chromatography. The column was packed in CHCl₃/MeOH (97:3). It was necessary to increase the polarity to CHCl₃/MeOH (92:8) in order to elute off the product. The fractions containing the desired product were combined and dried, yielding 74.8 mg (102 umol, 78%) of product. $^1$H NMR (CDCl₃): d 8.50 (t, 1H, central methine), 7.92 (dd, $J_{1=14}$ Hz, $J_2$=2 Hz, 2H, methines), 7.81 (d, 2H, tosyl), 7.35 (d, J=8.2 Hz, 2H, tosyl), 4.37 (cm, 8H, NCH₂R), 4.09 (br t, 2H, RCH₂OTs), 2.45 (s, 3H, tosyl methyl), 1.2–1.9 (unres. cm, bulk methylenes), 0.91 (t, J=7.2 Hz, 9H, terminal methyl).

Example IX

Synthesis of Fluorescent Lanthanide Chelates with a Single Negative Charge

Terbium(III) Bis-(N,N'-bis(salicylidene)ethylenediamine) piperidinium salt, Hpip⁺ Tb(SALEN)₂⁻: N,N'-bis(salicylidene)ethylenediamine (SALEN) (0.719 g, 2.68 mmol) was dissolved in 40 mL MeOH at 60° C. Terbium chloride hexahydrate (0.5 g, 1.34 mmol) dissolved in 1 mL water was added to the solution. Piperidine (536 µL, 5.42 mmol) was added and a yellow precipitate immediately formed. After 1 h, the heat was removed and the reaction mixture was left stirring overnight. The solid was filtered and dried yielding 709 mg (0.91 mmol, 68%) of the desired complex. Electrospray (neg. ion) MS [MeOH/H₂O: 95/5] (peak, rel. int.) 691.2 (M⁻¹, 100) calc. M⁻¹=691.5 amu.

Europium(III) Bis-(N,N'-bis(salicylidene)ethylenediamine) piperidinium, Hpip⁺ Eu(SALEN)₂⁻: N,N'-bis(salicylidene)ethylenediamine (SALEN) (0.360 g, 1.34 mmol) was dissolved in 40 mL MeOH and piperidine (298 µL, 3.02 mmol) at 60° C. Europium chloride hexahydrate (0.246 g, 0.67 mmol) dissolved in 0.5 mL water was added to the solution and a yellow precipitate immediately came out of solution. After 1 h, the heat was removed and the reaction mixture was left for 2 hours. The solid was filtered and dried yielding 341 mg (0.44 mmol, 66%) of the desired complex.

Example X

Construction of Targeted Naturally Fluorescent Proteins

Molecular Biology. The Aequorea Victoria GFP coding sequence (Clontech) was engineered to contain the mutations S72A, Y145F and T203I (Sapphire) (SEQ. ID. NO: 1) (Green Fluorescent Proteins, Chapter 2, pages 19 to 47, edited Sullivan and Kay, Academic Press). This fluorescent protein has an excitation peak around 395 nm and an emission peak around 512 nm, making it a useful donor with the trimethine oxonol acceptor. To create a targetable construct, the plasma membrane localisation signal form the tyrosine kinase lyn was fused in frame with the Sapphire coding sequence. This was achieved using two stage PCR by adding the sequence (MGCIKSKRKDNLNDDGVDMKT, SEQ. ID. NO: 15) to the N-terminus of Sapphire. This sequence, which is derived from the first 21 amino acids of lyn, contains a well defined membrane localization domain that serves in vivo to specifically localize lyn to the inner plasma membrane of mammalian cells.

In the first-stage PCR, a sense primer (ATTCCCAAGCTTGCGGCCGCCACCATGGGCTGCATCAA-GAGCAAGCGCAAGGACAACCTGAACGAC-GACGGCGTG, SEQ ID. NO: 20) and an anti-sense primer (CCGGAATTCTTACTTGTACAGCTCGTCCATGCC, SEQ ID. NO: 21) were used. In the second-stage, a sense primer (GACAACCTGAACGACGACGGCGTGGA-CATGAAGACCATGGTGAGCAAGGGCGAGGAGCTG SEQ ID. NO: 22) and the anti-sense primer were used. The PCR product was digested with HindIII and EcoRI, and ligated into the mammalian expression vector pCDNA3 (Invitrogen). Additional targeting sequences were made based on this construct. To utilize the NcoI sites that flank the Lyn sequence, the Lyn Sapphire insert was subcloned from pcDNA3 into pBluescriptII (Stratagene) using the restriction sites HindIII and EcoRI. Oligonucleotides coding for the additional targeting sequences Lyn D10, D15 and RRR (see Table 4) with their complimentary strands were synthesized, using standard techniques.

TABLE 4

| Construct Name | Sequence | SEQ. ID. NO: | Orientation |
| --- | --- | --- | --- |
| Lyn Sapphire | MGCIKSKRKDNLNDDGVDMKT | SEQ. ID. NO: 15 | N-terminal |
| Lyn D15 Sapphire | MGCIKSKRKDNLNDDT | SEQ. ID. NO: 17 | N-terminal |
| Lyn D10 Sapphire | MGCIKSKRK | SEQ. ID. NO: 18 | N-terminal |
| Lyn RRR Sapphire | MGCIKSKRKDNLNDDRRRT | SEQ. ID. NO: 19 | N-terminal |
| Ras Sapphire | KKKKKKKSKTKCVIM | SEQ. ID. NO: 16 | C-terminal |
| LynRas Sapphire | MGCIKSKRKDNLNDDGVDMKT + KKKKKKKSKTKCVIM | SEQ. ID. NO: 15 + SEQ. ID. NO: 16 | N-terminal + terminal |

These oligomers were phosphorylated using T4 polynucleotide kinase, hybridized by heating the complimentary strands to 95° C. and then slowly cooling the samples to room temperature. Double stranded oligomers, containing the required targeting sequence, were inserted 5' of the sapphire GFP coding region after removal of the original Lyn sequence by digestion of the lyn Sapphire DNA with NcoI. The orientation and sequence of the inserts was confirmed by DNA sequencing.

To generate fluorescent proteins with C-terminal localization motifs and C and N-terminal localization motifs, oligonucleotides was synthesized and used as an antisense primer in PCR. The ras oligonucleotide contained the antisense sequence of the C-terminal CAAX-box and polybasic region of K-Ras followed by 16 nucleotide bases that overlap into the C-terminus of Sapphire GFP. The T3 primer was used as the sense primer. Either Lyn Sapphire or Sapphire alone plasmids were used as template DNA, depending on the constructs required. All inserts were subcloned into the mammalian expression construct pcDNA3 prior to transfection into cells.

The first requirement for using GFP as a voltage-sensitive FRET donor is to selectively target it to the desired membrane, in this example the plasma membrane. While many proteins bind to the cell membrane, a large number of these candidate proteins also have high expression levels in other cellular locations. Often fusion of a naturally fluorescent protein to a protein that is expressed at the plasma membrane will result in fluorescence throughout the secretory pathway. Non specific expression patterns are not amenable for use as a FRET donor because a large percentage of the emitted light originates from irrelevant cellular locations and results in a high background, which precludes large signal changes and may even be a source of artifactual fluorescence changes. We have found that N-terminal fusion of a ~20 amino acid plasma membrane targeting sequence from Lyn tyrosine protein kinase (Resh. (1994) Cell 76 (3) 411–3), a member of the Src family of tyrosine protein kinases, and C-terminal fusion of CAAX motifs (Magee and Marshall (1999) Cell 98 9–12) to GFP results in specific fluorescence at the plasma membrane of transfected mammalian cells.

Example XI

Transient Transfections and Generation of Stable Cell Lines

The targeted naturally fluorescent protein constructs were transiently transfected into CHO cells using the lipid-mediated transfection reagent Lipofectamine (GibcoBRL) at a 1:12 DNA to lipid ratio. Expression of the membrane targeted sapphire GFP in rat basophilic leukemia (RBL-1) cells was achieved by transfecting wild-type RBL cells with the GFP constructs by electroporation. Cells lines stably expressing the GFP constructs were generated for both RBL-1 and CHO host cells by selecting for geneticin (G418) resistance. Targeted GFP-expressing clones were sorted using a Becton Dickinson FACS Vantage SE cell sorter equipped with a Coherent Innova Krypton 302 laser. Sapphire GFP was excited using the 407 nm line of the krypton laser. Individual cells were sorted into microtiter plates based on fluorescence through a 530/30 nm emission filter.

Example XII

Measurement of Membrane Potentials Using Targeted Naturally Fluorescent Proteins Trimethine Oxonol Loading. (bis-(1,3-dialkyl-2-thiobarbiturate)(DiSBAC$_x$(3)) acceptors, where x refers to the number of carbons in alkyl substituents, were loaded into washed cells by incubation at room temperature for 30 minutes with gentle shaking. RBL cells were harvested from confluent flasks using non-enzymatic cell dissociation buffer (GibcoBRL), pelleted, washed in BathI buffer (160 mM NaCl, 4.5 mM KCl, 2 mM CaCl$_2$, 1 mM MgCl$_2$, 10 mM D-glucose, 10 mM HEPES pH 7.4), resuspended to 2×10$^6$ cells/mL in Bath1 containing oxonol, and incubated at room temperature for 30 minutes with gentle shaking. Oxonol was washed out and cells were plated at 1×10$^5$ cells per well in poly-L-lysine coated black-wall microtiter plates (Costar). Cells were allowed to attach to the poly-L-lysing by settling for 30 minutes or centrifugation in the plate at 170×g for 5 min. The butyl oxonols were loaded using 0.2 mg/mL pluronic 127 and the hexyl with pluronic and 1.5 mM β-cyclodextrin. Both butyl and hexyl oxonols were washed out before assaying cells. The ethyl oxonols were loaded without pluronic and left in the buffer during the assays.

Addition of trimethine oxonols to CHO or RBL-1 cells expressing Lyn-Sapphire GFP caused an approximately 10–50% quenching of the GFP fluorescence and a concomitant increase in the oxonol emission. The spectral changes are indicative of FRET between the plasma membrane targeted GFP and the membrane-bound oxonol. At normal negative cellular resting membrane potentials the majority of oxonol acceptors are localized in the outer plasma membrane leaflet and only partial quenching of the GFP donor is expected. Direct excitation of the FRET acceptor is a common problem in FRET applications. For this reason, we decided to implement Sapphire GFP since it has a single excitation peak at 395 nm, the excitation minimum for trimethine oxonols. Even though S65T mutants have ~2-fold greater extinction coefficients, the ~490 nm excitation light necessary to optimally excite these mutants results in substantial direct excitation of oxonol, which causes non FRET emission. The oxonol excitation spectrum has a minimum at ~400 nm which is ideal for Sapphire excitation; At 490 nm, the excitation maximum of S65T mutants, the oxonol is ~15% excited compared its maximum. Since the oxonol has a maximal extinction of ~200,000 M$^{-1}$cm$^{-1}$ this corresponds to an effective extinction of 30,000 M$^{-1}$cm$^{-1}$ which is comparable to GFPs. Oxonol molecules not located at the plasma membrane are not efficiently excited with 405 nm light, which is ~130 nm shorter than the oxonol absorbance maximum. Furthermore, oxonols not in membranes are essentially non fluorescent. Taken together, the light emitted from the stained cells is primarily from the plasma membrane where the Sapphire donors are located. Measurement of fluorescence emission from stained cells on coverslips, in cuvettes, and in microtiter plates indicated that the 5–40% of the detected oxonol emission originates from direct excitation. The percentage depends on which oxonol is used, since binding to different cellular membrane varies with dye physiochemical properties. The more hydrophilic and water-soluble oxonols easily partition into most intracellular membranes and compartments.

Calibration of Voltage Sensitivity

We evaluated the voltage-sensitivity of the GFP/trimethine oxonol FRET pairs using whole-cell voltage clamp techniques to control the voltage across the plasma membrane while simultaneously recording the intensities of the GFP and oxonol emissions.

Simultaneous electrical and optical measurements were performed on a Zeiss 100 inverted epifluorescence microscope adapted for simultaneous emission ratioing. Experiments were conducted with either a 40× 1.4 NA or 63× 1.25 NA Zeiss Fluar objective. The excitation source was a 75W xenon arc lamp. Excitation light was passed through a 405 nm±10 nm filter (Omega Optical) and was used to excite cells expressing the naturally fluorescent proteins after passage through a 425 nm mirror. The fluorescence emission was passed through a 435 nm long pass filter before being split with a 550 nm DRLP second dichroic. GFP emission measurements were made after being filtered through 510±30 nm filter. The transmitted oxonol emission was measured after passage through a 740 nm dichroic and a 580±35 nm band pass filter. The emitted light was simultaneously detected using two PMTs (Hamamatsu). Infrared light 1000±150 nm was used to image the cell for patch clamping. Cells were stained with 6 uM DiSBAC$_2$ for a minimum of 20 minutes unless otherwise noted.

Patch Clamping

All patch clamp experiments were performed at room temperature using an AxoPatch 1C amplifier and the pClamp software suite (Axon Instruments, Inc. Foster City, Calif.). A ground was created by placing an Ag/AgCl pellet placed directly in the bath. Patch pipettes were made on a Flaming/Brown micropipette puller (Model P-97, Sutter Instruments, Inc. Novato, Calif.) from borosilicate glass with resistances when filled with pipette solution of 3–6 MΩ. The pipette solution was composed of 140 mM K-gluconate, 2 mM MgCl$_2$, 1 mM CaCl$_2$, 10 mM EGTA, 10 mM HEPES and pH 7.2.

Figure 24B:
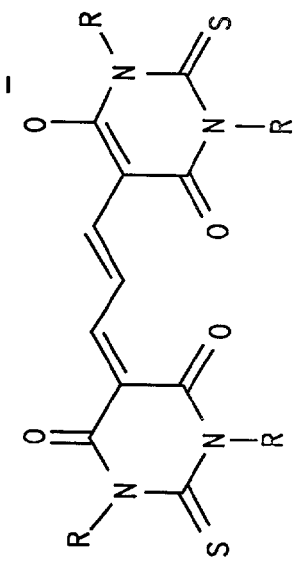
FIG. 24 A shows a schematic representation of exogenous fluorescent lipid donors bound to the outer membrane of a bimolecular leaflet. B shows the structure of bis-(1,3-dialkyl-2-thiobarbiturate), one of the trimethine oxonol acceptors of the present invention. C shows a schematic view of a possible arrangement of the GFP/oxonol sensor with a GFP donor located on one surface of the biological membrane. Upon depolarization, the oxonol acceptors move to the lower membrane surface resulting in enhanced FRET due to the decrease in mean distance between the donor and acceptor.
Figure 24A:
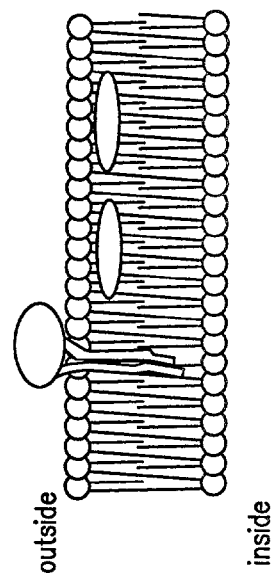
Figure 24C:
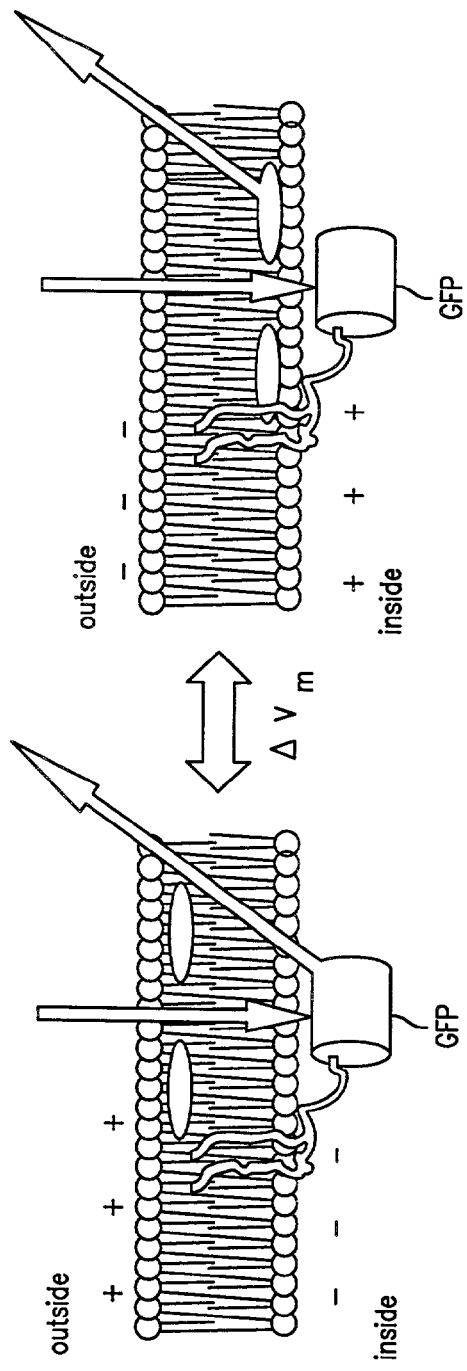
Figure 25:
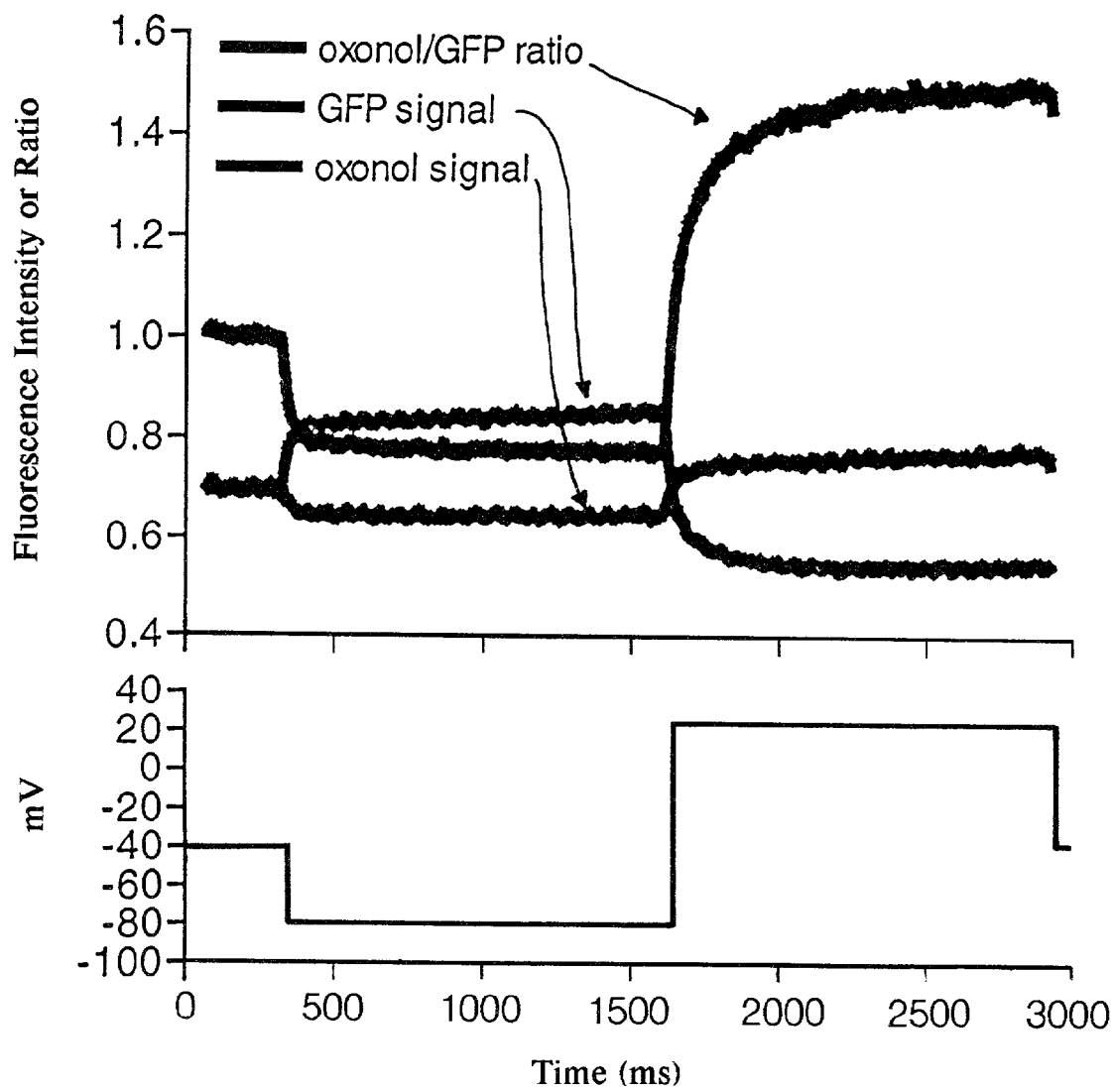
FIG. 25. Shows an example ratiometric voltage-sensitive FRET signal in a voltage clamped single cell. In this example the cell was held at −40 mV and hyperpolarized to −80 mV at approximately 300 ms per time point. At approximately 1600 ms, the cell was depolarized 100 mV to +20 mV. The oxonol and GFP fluorescence intensities synchronously change in opposite directions. In this case, the direction of the fluorescence changes indicate that the GFP donor resides on the inner plasma membrane leaflet. Note how the calculation of the emission ratio eliminates the noise in the GFP and oxonol signals. The voltage clamp stimulus protocol is shown below.

An example of a large voltage-sensitive FRET response from a single cell is shown in FIG. 25. Upon depolarization, the green donor emission decreases and the oxonol emission increases as predicted for a net oxonol translocation from the outer plasma membrane leaflet to the inner, as depicted in FIG. 24. These fluorescence changes are in opposite directions to those observed using a coumarin-lipid donor, which binds to the extracellular plasma membrane leaflet (Gonzalez and Tsien, (1997) Chem. Biol. 4 (4) 269–77). These data confirm the targeting of the naturally fluorescent protein to the inner leaflet of the plasma. For the coumarin-lipid/oxonol pairs the majority of the signal can be manipulated by changing the relative dye staining concentrations. In the GFP/oxonol case the majority of the signal change is almost always from GFP, probably because of the spill over of the GFP emission into the oxonol signal.

Example XIII

Comparison of Different Membrane Targeting Sequences

We systematically characterized and compared the voltage-sensitivity of 6 Sapphire GFP constructs based on the N-terminal fused Lyn domain and the C-terminal fused-CAAX motifs. From these experiments we wanted to determine the generality of voltage-sensitive FRET with different GFP donors and also to find a probe with intrinsically greater voltage-sensitivity. The six constructs are listed in Table 4. The rationale for choosing these constructs was that by modifying the targeting sequence length, attachment point, and charge, we had a good chance of modulating FRET, since it is typically sensitive to the distance and orientation between donor and acceptor chromophores. Truncations of the Lyn domain were prepared to test whether shortening the targeting sequence would retain membrane binding and if so whether the shorter linker placed the GFP closer to the membrane and resulted in greater FRET, and possibly voltage-sensitive FRET. Two truncations of the targeting sequence were made at aspartic acid residue 10 (D10 Sapphire) and aspartic acid residue 15 (D15 Sapphire). Also, a triple arginine patch present in the N-terminal region of Src tyrosine protein kinase was substituted for the corresponding Lyn residues in the Lyn Sapphire construct (Lyn RRR Sapphire). Two other constructs were made by adding a C-terminal plasma membrane targeting sequence from K-Ras; one with the C-terminal anchor fused to the Sapphire GFP and the other also consisting of the Lyn sequence fused to the N-terminus, a construct with two membrane anchors. The C-terminal constructs were prepared to test if membrane anchoring via the C-terminal would cause a different FRET interaction with the oxonol. In the case of the double-anchored probe, it was speculated that such a major modification might lead to an orientation change that could modulate FRET. A third factor that was varied was the number of positive charges on the peptide linker. This issue was addressed, in part, by the triple arginine and the K-RAS constructs that contain a large number of positively charged amino acids. Since the oxonols are negatively charged, the possibility of a weak electrostatic attraction between donor and acceptor was tantalizing. Finally, the number of positive charges on the inner leaflet could shift the voltage dependence of the oxonol displacement currents to more negative voltages, which would move the voltage-sensitivity maximum into a more physiologically relevant range, more negative of –5 mV, which was previously observed in LmTK⁻ cells (Gonzalez and Tsien, (1995) Biophys. J. 69 (4) 1272–80).

The constructs were transiently transfected into CHO cells and voltage-sensitivity was determined according to the procedure described above, using a minimum of 5 cells for each construct. Data from 3 separate runs were averaged for the hyperpolarization and depolarization protocol shown in the inset. The measured sensitivities were similar for the two different voltage pulses. Cells with above average brightness and apparent membrane targeting were selected for patch-clamping. Cell capacitance values were typically between 10 and 15 pF. The results are summarized in Table 5.

TABLE 5

| Construct Name | Ratio Change per 100 mV |
| --- | --- |
| Lyn Sapphire | 34+/–5 |
| Lyn D15 Sapphire | 21+/–8 |
| Lyn D10 Sapphire | 29.5+/–7 |
| Lyn RRR Sapphire | 26+/–7 |
| Ras Sapphire | 59+/–8 |
| LynRas Sapphire | 15+/–10 |

The first major observation was that all the constructs resulted in voltage-sensitive FRET. This is important because it demonstrates that voltage-sensitive FRET is generally applicable as long as the GFP is specifically targeted and close enough to the membrane to undergo FRET with the oxonol.

Secondly, it is clear from the results that the RAS targeted Sapphire GFP was nearly 2-fold more sensitive than the other constructs under these transient conditions. No fluorescence changes were observed in the absence of added oxonol. The 60% ratio change per 100 mV seen for the RAS Sapphire GFP donor is comparable to the high sensitivity seen with purely exogenous probes that use coumarin phospholipid donors. The results demonstrate that the nature of the targeting sequence can influence the magnitude and sensitivity of the fluorescence measurements, even among very similar localization sequences.

Example XIV

Temporal Analysis of Different Fluorescent Protein Oxonol Pairs

The temporal response of the GFP/oxonol FRET change is dependent on the oxonol translocation rate and follows the previously observed trend with oxonol acceptors, faster responses with more hydrophobic acceptors. The measured time constants for the ethyl and butyl oxonol acceptors are ~50 and ~5 ms respectively in the targeted GFP expressing cells. The FRET response and the electrophysiologically measured displacement currents have identical time constants. The measured response times are 2–4 fold faster than previously reported and may be a property of the cells used or from a slight difference in temperature. The temporal responses of DiSBAC$_4$ displacement currents in cells expressing GFP and those of the host cells did not show any significant differences.

Example XV

Measurement of Voltage Changes in High Throughput Screening Format

Fluorescence measurements from 96 well mircoplates were made with the VIPR™ microtiter plate reader (U.S. application Ser. No. 09/122,544, filed Jul. 24, 1998 entitled "Detector and Screening Device for Ion Channels.")

Cells were illuminated with light from a 300 W xenon arc lamp passed through a 400±7 nm band pass excitation filter and fluorescence emission intensities were recorded via two PMTs using a 535±18 nm band pass emission filter to collect sapphire GFP emission and a 580±30 nm band pass filter to collect trimethine oxonol emission A typical VIPR™ run involved recording fluorescence intensities at the donor and acceptor wavelengths simultaneously for 35 seconds at 1 Hz with liquid addition occurring between 12 and 15 seconds. Data were analyzed by first subtracting background, (intensities from wells without cells) from the sample wells. The fluorescence ratio (oxonol/GFP emission) was then calculated and normalized to the starting ratio of each well before liquid addition. The final ratio was determined using data between 17 and 24 seconds. The fraction of GFP emission that emitted in the wavelength range used for oxonol detection (580 nm±30) was determined using cells prior to the addition of the oxonol. The leakage of the GFP emission into the oxonol signal was subtracted prior to data analysis, for oxonol stained cells assuming the same GFP emission profile in the presence of oxonol.

Figure 26:
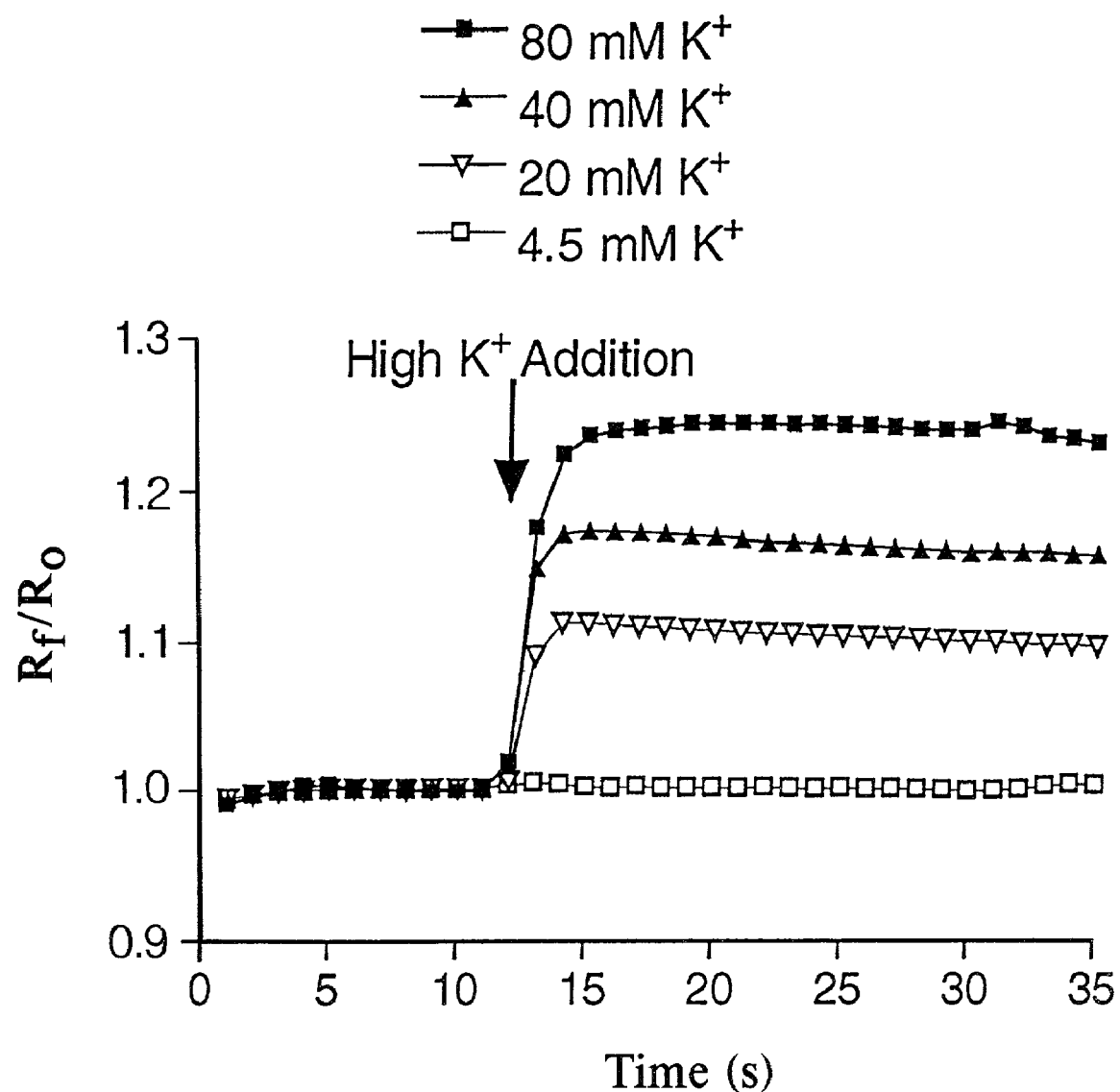
FIG. 26. Shows membrane potential assays using GFP/oxonol FRET voltage sensors performed in a 96 well plate. The additions of buffer containing various potassium concentrations were added using the VIPR™ plate reader between 12 and 15 seconds, as indicated by the arrow to RBL cells expressing the lyn-sapphire GFP fusion protein. (add patent citation). The cells were loaded with 4 uM DiSBAC$_6$. The traces show the oxonol to GFP ratio normalized to the starting ratio prior to high K+ stimulus at various extracellular K concentrations.

The homogeneity of the stable lines enabled us to perform membrane potential assays using an integrated liquid handling and fluorescence plate reader capable of fast simultaneous emission ratioing. Cellular assays that test for compounds that block high $K^+$ induced depolarizations have been successfully performed in microtiter plates using all the stable Sapphire GFP cell lines with trimethine oxonols FRET acceptors. The RBL-1 cells have an endogenous inward rectifying $K^+$ channel, IRK, that sets the membrane potential to the $K^+$ equilibrium potential. Addition of a high $K^+$ solution (164.5 mM KCl, 2 mM $CaCl_2$, 1 mM $MgCl_2$, 10 mM D-glucose, 10 mM HEPES pH 7.4) causes a rapid depolarization that is detected with the FRET membrane potential probes. Data for the hexyl trimethine oxonol in the Lyn RBL line is shown in FIG. 26.

Figure 27:
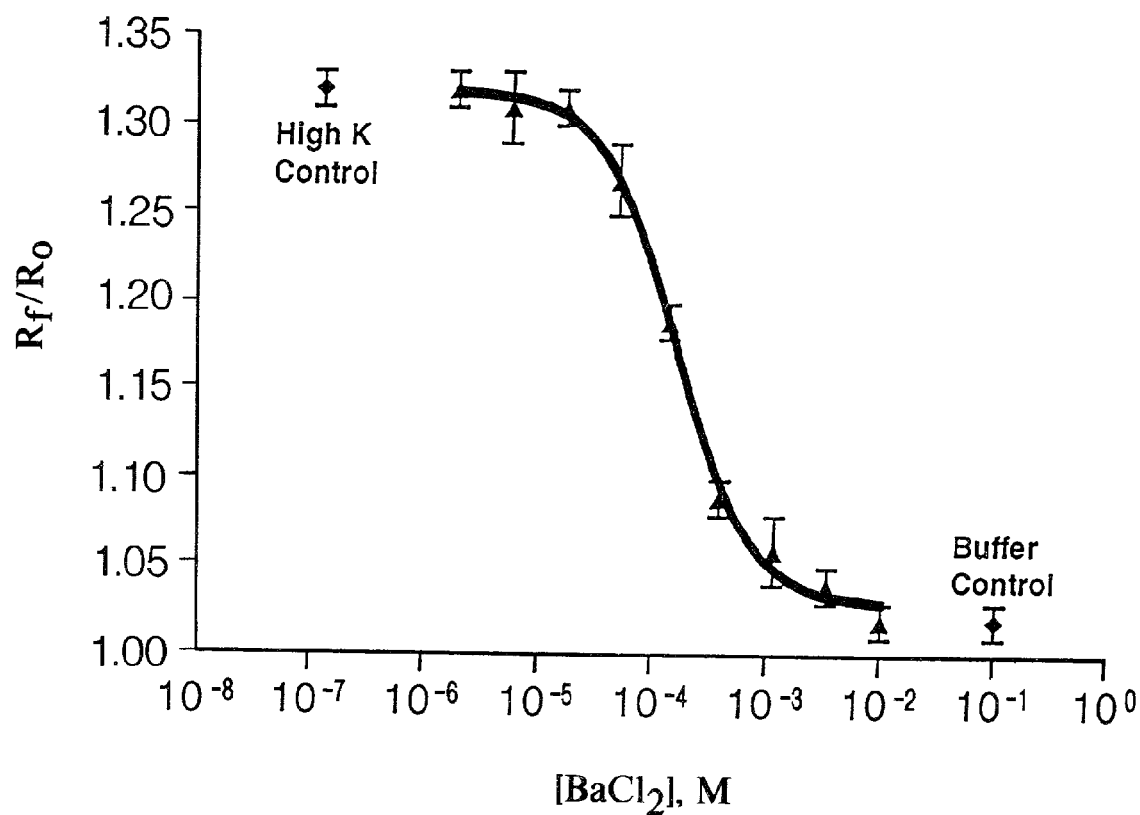
FIG. 27. Shows a dose response of barium on endogenously expressed IRKI and the high K+ response as determined using RBL cells expressing the lyn-sapphire GFP fusion, and loaded with 10 uM DiSBAC$_4$. The high potassium and normal sodium containing buffer controls in the absence of antagonist are shown to the left and right of the curve, respectively. The error bars are +/− standard deviation of wells at each concentration.

The data shows very reproducible well-to-well responses, with the time response limited by the liquid addition. The ability to use microtiter plates makes the targetable voltage probes compatible with high-throughput drug screening and allows facile optimization of acceptor concentration for the best ratio response. The utility for compound screening is further demonstrated by incubating the cells with $Ba^{2+}$ which blocks IRK and depolarizes the cells. This causes the high $K^+$ signal to be blocked since the cells are already depolarized when the high $K^+$ solution is added. The $Ba^{2+}$ dose-response in the Lyn Sapphire GFP/butyl trimethine oxonol is shown in FIG. 27. Microtiter wells treated with the IRK antagonists can be clearly identified.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

---

What is claimed is:

1. A compound having the formula

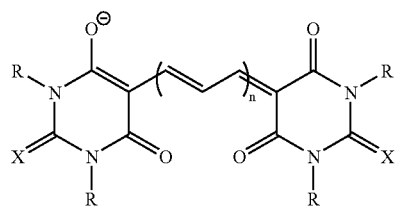

wherein

X is oxygen or sulfur;

R is independently selected from H, aryl, aralkyl, heteroalkyl, cycloalkyl, cycloalkyl lower-alkyl, and $C_7$–$C_{12}$ alkyl n is an integer from 1 to 3;

and salts thereof.

2. The compound of claim 1, wherein X is sulfur.

3. The compound of claim 1, wherein the aryl group is substituted with a substituent selected from a hydrocarbyl, an alkyl, a heteroalkyl, and a halogen group.

4. The composition of claim 1, wherein R is heteroalkyl.

5. The composition of claim 4 wherein the heteroalkyl has the formula:

—$(CH_2)_xA(CH_2)_zCH_3$, wherein:

A is oxygen or sulfur;

x is independently an integer from 1 to about 20;

z is independently an integer from 1 to about 20; and x+1+z is less than about 40.

6. A compound having the formula

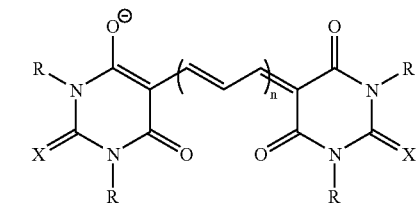

wherein

X is oxygen or sulfur;

R is independently selected from H and heteroalkyl, n is an integer from 1 to 3;

and salts thereof.

7. The compound of claim 6, wherein X is sulfur.

8. The compound of claim 6, wherein the heteroalkyl group has a formula:

—$(CH_2)_xA(CH_2)_zCH_3$, wherein:

A is oxygen or sulfur;

x is independently an integer from 1 to about 20;

z is independently an integer from 1 to about 20; and x+1+z is less than about 40.

* * * * *